US007527943B2

(12) United States Patent
Anderson et al.

(10) Patent No.: US 7,527,943 B2

(45) Date of Patent: May 5, 2009

(54) COMPOSITIONS OF ORTHOGONAL GLUTAMYL-TRNA AND AMINOACYL-TRNA SYNTHETASE PAIRS AND USES THEREOF

(75) Inventors: J. Christopher Anderson, San Francisco, CA (US); Peter G. Schultz, La Jolla, CA (US); Stephen Santoro, Cambridge, MA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 10/563,656

(22) PCT Filed: Jul. 7, 2004

(86) PCT No.: PCT/US2004/021813

§ 371 (c)(1), (2), (4) Date: Jun. 22, 2006

(87) PCT Pub. No.: WO2005/007624

PCT Pub. Date: Jan. 27, 2005

(65) Prior Publication Data

US 2007/0020634 A1 Jan. 25, 2007

Related U.S. Application Data

(60) Provisional application No. 60/485,451, filed on Jul. 7, 2003, provisional application No. 60/513,109, filed on Oct. 20, 2003.

(51) Int. Cl.

| | |
|---|---|
| *C12P 21/02* | (2006.01) |
| *C12N 9/22* | (2006.01) |
| *C12N 15/87* | (2006.01) |

(52) U.S. Cl. ..................... 435/69.1; 435/91.2; 435/183; 435/440; 435/419; 435/455; 435/199; 530/350

(58) Field of Classification Search ....................... None
See application file for complete search history.

(56) References Cited

U.S. PATENT DOCUMENTS

| | | | |
|---|---|---|---|
| 6,927,042 | B2 | 8/2005 | Schultz et al. |
| 7,045,337 | B2 | 5/2006 | Schultz et al. |
| 7,083,970 | B2 | 8/2006 | Schultz et al. |

FOREIGN PATENT DOCUMENTS

| | | | |
|---|---|---|---|
| WO | WO 02/085923 | A2 | 10/2002 |
| WO | WO 02/086075 | A2 | 10/2002 |
| WO | WO 2004/035605 | A2 | 4/2004 |
| WO | WO 2004/035743 | A2 | 4/2004 |
| WO | WO 2004/094593 | A2 | 11/2004 |
| WO | WO 2005/003294 | A2 | 1/2005 |

OTHER PUBLICATIONS

Anderson (Aug. 2003) "Pathway engineering of the expanding genetic code." Thesis presented for the degree of Doctor of Philosophy in Chemistry, The Scripps Research Institute, La Jolla, Ca. Call No. QD1000. A63 (2003);UMI Publication No. 3111397.

Anderson and Schultz (2003) "Adaptation of an Orthogonal Archaeal Leucyl-tRNA and Synthetase Pair for Four-base, Amber, and Opal Suppression." *Biochemistry*, 42(32): 9598-9608.

Anderson et al. (2002) "Exploring the limits of codon and anitcodon size." *Chemistry & Biology*, 9: 237-244.

Anderson et al. (May 18, 2004) "An expanded genetic code with a functional quadruplet codon." *Proceedings of the National Academy of Sciences, USA*, 101(20): 7566-7571.

Bossi and Roth (1981) "Four-base codons ACCA, ACCU and ACCC are recognized by frameshift suppressor sufJ." *Cell*, 25(2): 489-496.

Chen et al. (1994) "Properties of the lysyl-tRNA synthetase gene and product from the extreme thermophile Thermus thermophilus." *Journal of Bacteriology*, 176(9): 2699-2705.

Chin et al. (2003) "An expanded eukaryotic genetic code." *Science*. 301: 964-967.

Chin et al. (2002) "Addition of a photocrosslinking amino acid to the genetic code of *Escherichia coli," Proc. Natl. Acad. Sci. U. S. A.* 99(17):11020-11024.

Chin et al. (2002) "Addition of p-azido-L-pheylalanine to the genetic code of *Escherichia coli," J. Am. Chem. Soc.* 124(31):9026-9027.

Curran and Yarus (1987) "Reading frame selection and transfer RNA anticodon loop stacking." *Science*, 238: 1545-1550.

Edwards and Schimmel. (1990) "A bacterial amber suppressor in *Saccharomyces cerevisiae* is selectively recognized by a bacterial aminoacyl-tRNA synthetase," *Mol. Cell. Biol.* 10(4):1633-1641.

Feng et al. (2003) "Expanding tRNA recognition of a tRNA synthetase by a single amino acid change." *Proceedings of the National Academy of Sciences USA*, 100(10): 5676-5681.

Forster et al. (2003) "Programming peptidomimetic synthetases by translating genetic codes designed de novo." *Proceedings of the National Academy of Sciences USA*, 100(11): 6353-6357.

Hirao et al. (2002) "An unnatural base pair for incoproating amino acid analogues into protein," *Nature Biotechnology*, 20:177-182.

Hohsaka and Sisido (2002) "Incorporation of non-natural amino acids into proteins." *Current Opinion in Chemical Biology*, 6: 809-815.

Hohsaka et al. (2001) "Five-base codons for incorporation of non-natural amino acids into proteins." *Nucleic Acids Research*, 29(17): 3646-3651.

(Continued)

*Primary Examiner*—Andrew D Kosar
*Assistant Examiner*—Kagnew H Gebreyesus
(74) *Attorney, Agent, or Firm*—Quine Intellectual Property Law Group; Gary Baker

(57) ABSTRACT

Compositions and methods of producing components of protein biosynthetic machinery that include glutamyl orthogonal tRNAs, glutamyl orthogonal aminoacyl-tRNA synthetases, and orthogonal pairs of glutamyl tRNAs/synthetases are provided. Methods for identifying these orthogonal pairs are also provided along with methods of producing proteins using these orthogonal pairs.

14 Claims, 6 Drawing Sheets

OTHER PUBLICATIONS

Hohsaka et al. (1999) "Incorporation of Two Different Nonnatural Amino Acids Independently into a Single Protein through Extension of the Genetic Code," *J. Am. Chem. Soc.*, 121(51):12194-12195.

Hohsaka et al. (1999) "Efficient Incorporation of Nonnatural Amino Acids with Large Aromatic Groups into Streptavidin in In Vitro Protein Synthesizing Systems," *J. Am. Chem. Soc.*, 121(1):34-40.

Hou et al. (1992) "Novel transfer RNAs that are active in *Escherichia coli." Biochemistry*, 31(17): 4157-4160.

Kobayayashi et al. (2003) "Structural basis for orthogonal tRNA specific of tyrosyl-tRNA synthetases for genetic code expansion." *Nature Structural Biology*, 10(6): 425-432.

Kowal and Oliver (1997) "Exploiting unassigned codons in *Micrococcus luteus* for tRNA-based amino acid mutagenesis," *Nucl. Acid Res.*, 25(22):4685-4689.

Kwok and Wong (1980) "Evolutionary relationship between Halobacterium cutirubrum and eukaryotes determined by use of aminoacyl-tRNA sythetases as phylogenetic probes," *Can. J. Biochem*. 58(3):213-218.

Liu and Schultz (1999) "Progress toward the evolution of an organism with an expanded genetic code." *Proceedings of the National Academy of Sciences USA*, 96: 4780-4758.

Ma et al. (1993) "In vitro protein engineering using synthetic tRNA(Ala) with different anticodons" *Biochemistry*, 32(31):7939-7945.

Magliery et al. (2001) "Expanding the genetic code: selection of efficient suppressors of four-base codons and identification of "shifty" four-base codons with a library approach in *Escherichia coli." Journal of Molecular Biology*, 307: 755-769.

Moore et al. (2000) "Quadruplet codons: implications for code expansion and the specification of translation step size," *J. Mol. Biol.*, 298(2):195-209.

Nureki et al. (1995) "Architectures of class-defining and specific domains of glutamyl-tRNA synthetase," *Science* 267: 1958-1965.

O'Connor (2002) "Insertions in the anticodon loop of tRNA(1)(Gin)(sufG) and tRNA(Lys) promote quadruplet decoding of CAAA." *Nucleic Acids Research*, 30(9): 1985-1990.

Ohno et al. (1998) "Co-Expression of Yeast Amber Suppressor $tRNA^{tyr}$ and Synthetase in *Escherichia coli*: Possibility to Expand the Genetic Code." *J. Biochem* 124(6):1065-1068.

Pastrnak et al. (2000) "A New Orthogonal Suppressor tRNA/Aminoacyl-tRNA Synthetase Pair for Evolving an Organism with an Expanded Genetic Code," *Helv. Chim. Acta* 83:2277-2286.

Rath et al. (1998) "How glutaminyl-tRNA synthetase selects glutamine," *Structure*, 6(4):439-449.

Sakamoto et al. (2002) "Site-specific incorporation of an unnatural amino acid into proteins in mammalian cells," *Nucleic Acids Res*. 30(21):4692-4699.

Santoro et al. (2002) "An efficient system for the evolution of aminoacyl-tRNA synthetase specificity," *Nature Biotechnology*, 20:1044-1048.

Sekine et al. (2001) "Structural basis for anticodon recognition by discriminating glutamyl-tRNA synthetase," *Nat. Struct. Biol.*, 8(3):203-206.

Tumbula et al. (2000) "Domain-specific recruitment of amide amino acids for protein synthesis," *Nature*, 407(6800):106-110.

Wang et al. (2000) "A New Functional Suppressor tRNA/Aminoacyl-tRNA Synthetase Pair for the in Vivo Incorporation of Unnatural Amino Acids into Proteins." *Journal of the American Chemistry Society*, 122: 5010-5011.

Wang et al. (2001) "Expanding the Genetic Code of *Escherichia coli." Science*, 292: 498-500.

Wang et al. (2003) "Addition of the Keto Functional Group to the Genetic Code of *Escherichia coli," PNAS*, 100(1):56-61.

Wu et al. (2002) "Enzymatic phosphorylation of unnatural nucleosides," *J. Am. Chem. Soc.*, 124(49):14626-14630.

Yarus et al. (1986) "Actions of the anticodnon arm in translation on the phenotypes of RNA mutants." *Journal of Molecular Biology*,192(2): 235-255.

Kowal et al. (2001) "Twenty-first amino-acyl tRNA synthetase-suppressor tRNA pairs for possible use in site-specific incorporation of amino acid analogues into proteins in eukaryotes and in eubacteria," *Proc. Natl. Acad. Sci., U.S.A.*, vol. 98, No. 5, pp. 2268-2273.

Liu et al. (1997) "Characterization of an 'orthogonal' suppressor tRNA derived from *E. coli* $tRNA_2^{Gln}$" Chemistry and Biology vol. 4, No. 9, pp. 685-691.

Santoro et al. (Oct. 12, 2003) "An archaebacteria-derived glutamyl-tRNA synthetase and tRNA pair for unnatural amino acid mutagenesis of proteins in *Escherichia coli*", vol. 31, No. 23, pp. 6700-6709.

Wang and Schultz (2001) "A general approach for the generation of orthogonal tRNAs", Chemistry and Biology, Current Biology London, GB, vol. 8, pp. 883-890.

International Search Report and Written Opinion for corresponding International Application No. PCT/US2004/21813, Jan. 27, 2005.

EPO Supplementary Search Report from corresponding European Patent Application No. 04777719.8.

Glu consensus tRNA

Glu consensus tRNA

AE(GU) tRNA

AQ(GU) tRNA

AQ(GC) tRNA

Fig. 4A
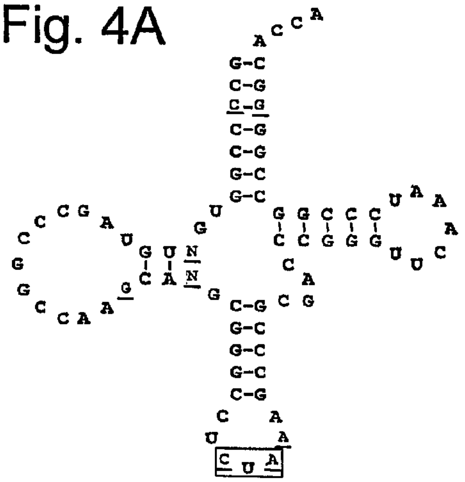
AE(NN) tRNA library
Fig. 4B
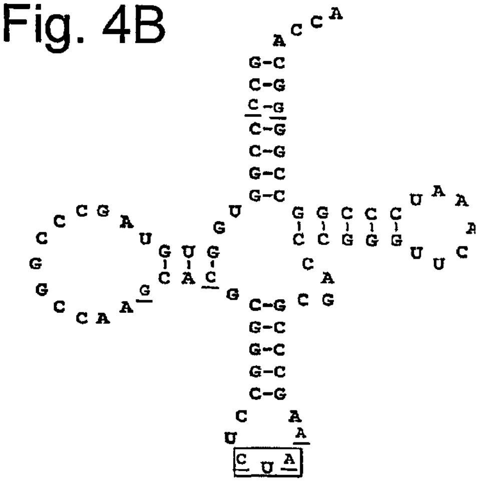
AE(GC) tRNA
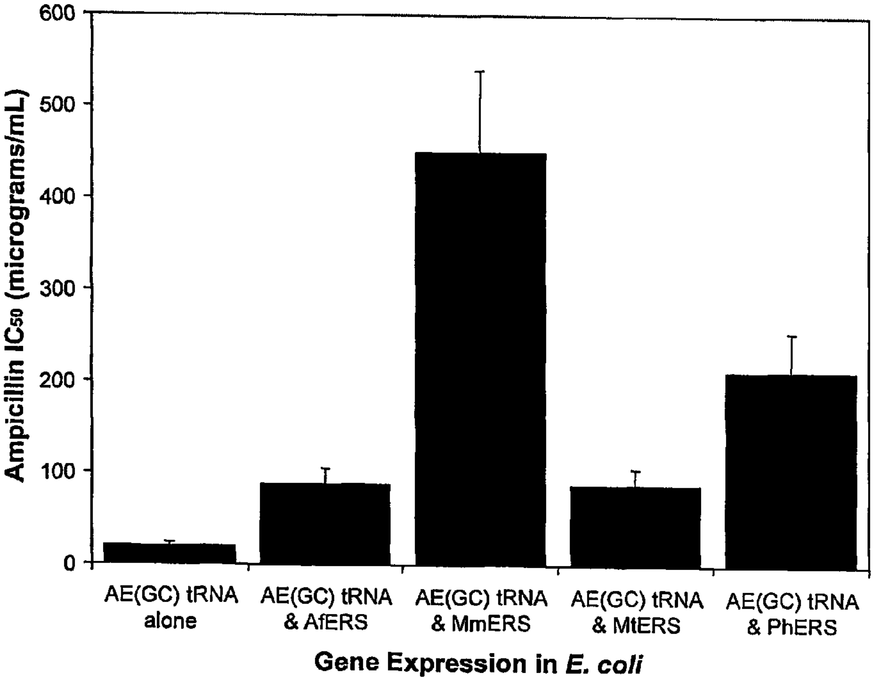
Fig. 4C

SEQUENCE LISTING

<160> NUMBER OF SEQ ID NOS: 111

<210> SEQ ID NO 1
<211> LENGTH: 78
<212> TYPE: RNA
<213> ORGANISM: Aeropyrum pernix

<400> SEQUENCE: 1
gccgcgguag uauagcccgg cccaguaugc gggccucucg agcccgugac ccggguucaa 60
aucccggccg cggcacca 78

<210> SEQ ID NO 2
<211> LENGTH: 78
<212> TYPE: RNA
<213> ORGANISM: Aeropyrum pernix

<400> SEQUENCE: 2
gccgcgguag uauagcccgg cccaguaugc gggccuuucg agcccgugac ccggguucaa 60
aucccggccg cggcacca 78

<210> SEQ ID NO 3
<211> LENGTH: 78
<212> TYPE: RNA
<213> ORGANISM: Archaeoglobus fulgidus

<400> SEQUENCE: 3
gcuccggugg uguagcccgg ccaaucauac gggacucucg aucccgugac ccggguucaa 60
aucccggccg gagcacca 78

<210> SEQ ID NO 4

```
<211> LENGTH: 78
<212> TYPE: RNA
<213> ORGANISM: Archaeoglobus fulgidus

<400> SEQUENCE: 4

gcuccggugg uguagcccgg ccaaucauuc cggccuuucg agccggcgac ccggguucaa    60

aucccggccg gagcacca                                                  78

<210> SEQ ID NO 5
<211> LENGTH: 78
<212> TYPE: RNA
<213> ORGANISM: Halobacterium sp.

<400> SEQUENCE: 5

gcuccguugg uguaguccgg ccaaucaucu ugcccucuca cggcaaggac uaggguucaa    60

aucccugacg gagcacca                                                  78

<210> SEQ ID NO 6
<211> LENGTH: 78
<212> TYPE: RNA
<213> ORGANISM: Halobacterium sp.

<400> SEQUENCE: 6

gcucgguugg uguaguccgg ccaaucaugu uggccuuucg agccgacgac caggguucaa    60

aucccugacc gagcacca                                                  78

<210> SEQ ID NO 7
<211> LENGTH: 78
<212> TYPE: RNA
<213> ORGANISM: Methanobacterium thermautotrophicus

<400> SEQUENCE: 7

gcuccgguag uguaguccgg ccaaucauuu cggccuuucg agccgaagac ucggguucaa    60

aucccggccg gagcacca                                                  78

<210> SEQ ID NO 8
<211> LENGTH: 78
<212> TYPE: RNA
<213> ORGANISM: Methanococcus jannaschii

<400> SEQUENCE: 8

gcuccggugg uguaguccgg ccaaucaugc gggccuuucg agcccgcgac ccggguucaa    60

aucccggccg gagcacca                                                  78

<210> SEQ ID NO 9
<211> LENGTH: 78
<212> TYPE: RNA
<213> ORGANISM: Methanococcus maripaludis

<400> SEQUENCE: 9

gcuccagugg uguaguccgg ccaaucaucc ggcccuuucg aggccgggac ucggguucaa    60

aucccggcug gagcacca                                                  78

<210> SEQ ID NO 10
<211> LENGTH: 78
<212> TYPE: RNA
<213> ORGANISM: Methanosarcina mazei

<400> SEQUENCE: 10

gcuccgauag uguagcucgg ccaaucauuc aggacucuca cuccugcgac uggguucaa     60
```

auccccaucg gagcacca 78

<210> SEQ ID NO 11
<211> LENGTH: 78
<212> TYPE: RNA
<213> ORGANISM: Methanosarcina mazei

<400> SEQUENCE: 11
gcuccgguag uguaguccgg ccaaucauuc cggccuuucg agccgaagac ucggguucga   60
aucccggccg gagcacca                                                78

<210> SEQ ID NO 12
<211> LENGTH: 78
<212> TYPE: RNA
<213> ORGANISM: Pyrobaculum aerophilum

<400> SEQUENCE: 12
cagccgguag ucuagcccgg acaaggaugc gggccucucg agcccgugac ccggguucaa   60
aucccggccg gggcacca                                                78

<210> SEQ ID NO 13
<211> LENGTH: 78
<212> TYPE: RNA
<213> ORGANISM: Pyrococcus abyssi

<400> SEQUENCE: 13
gccccggugg uguagcccgg ucaaucaugc gggacucucg aucccgcgac ccggguucaa   60
aucccggccg gggcacca                                                78

<210> SEQ ID NO 14
<211> LENGTH: 78
<212> TYPE: RNA
<213> ORGANISM: Pyrococcus abyssi

<400> SEQUENCE: 14
gccccggugg uguagcccgg ucaaacaugc gggccuuucg agcccgcgcc ccggguucaa   60
aucccggccg gggcacca                                                78

<210> SEQ ID NO 15
<211> LENGTH: 78
<212> TYPE: RNA
<213> ORGANISM: Pyrococcus furiosus

<400> SEQUENCE: 15
gccccggugg uguagcccgg ucaaucaugc gggacucucg aucccgcgac ccggguucaa   60
aucccggccg gggcacca                                                78

<210> SEQ ID NO 16
<211> LENGTH: 78
<212> TYPE: RNA
<213> ORGANISM: Pyrococcus furiosus

<400> SEQUENCE: 16
gccccggugg uguagcccgg ucaaacaugc gggccuuucg agcccgcgcc ccggguucaa   60
aucccggccg gggcacca                                                78

<210> SEQ ID NO 17
<211> LENGTH: 78
<212> TYPE: RNA

-continued

<213> ORGANISM: Pyrococcus horikoshii

<400> SEQUENCE: 17
gccccggugg uguagcccgg ucaaucaugc gggacucucg aucccgcgac ccgguucaa 60 aucccggccg gggcacca 78

<210> SEQ ID NO 18
<211> LENGTH: 78
<212> TYPE: RNA
<213> ORGANISM: Pyrococcus horikoshii

<400> SEQUENCE: 18
gccccggugg uguagcccgg ccaaacaugc gggccuuucg agcccgcgcc ccgguucaa 60 aucccggccg gggcacca 78

<210> SEQ ID NO 19
<211> LENGTH: 77
<212> TYPE: RNA
<213> ORGANISM: Sulfolobus solfataricus

<400> SEQUENCE: 19
gccgcggugg uuuagcccgg ucagaaugcg ggccucucga gcccgugacc cggguucaaa 60
ucccggccgc ggcacca 77

<210> SEQ ID NO 20
<211> LENGTH: 77
<212> TYPE: RNA
<213> ORGANISM: Sulfolobus solfataricus

<400> SEQUENCE: 20
gccgcggugg uuuagcccgg ucagaaugcg ggccuuucga gcccgugacc cggguucaaa 60
ucccggccgc ggcacca 77

<210> SEQ ID NO 21
<211> LENGTH: 77
<212> TYPE: RNA
<213> ORGANISM: Sulfolobus tokodaii

<400> SEQUENCE: 21
gccgcgguag uauagcccgg ucaguaugcg ggccucucaa gcccguggcc cggguucaaa 60
ucccggccgc ggcacca 77

<210> SEQ ID NO 22
<211> LENGTH: 78
<212> TYPE: RNA
<213> ORGANISM: Sulfolobus tokodaii

<400> SEQUENCE: 22
gccgcgguag uauagcccgg ucaagcacgc gggccuuucg agcccgugac ccgguucaa 60 aucccggccg cggcacca 78

<210> SEQ ID NO 23
<211> LENGTH: 78
<212> TYPE: RNA
<213> ORGANISM: Thermoplasma acidophilum

<400> SEQUENCE: 23
gcuccggugg uguaguccgg ccaagcauua gggacucuca aucccccgac ucggguccaa 60
aucccgaccg gagcacca 78

-continued

<210> SEQ ID NO 24
<211> LENGTH: 78
<212> TYPE: RNA
<213> ORGANISM: Thermoplasma acidophilum

<400> SEQUENCE: 24
gcuccggugg uguaguccgg acaagcauau cggccuuucg agccgacgac cuggguccaa 60
aucccggccg gagcacca 78

<210> SEQ ID NO 25
<211> LENGTH: 78
<212> TYPE: RNA
<213> ORGANISM: Thermoplasma volcanium

<400> SEQUENCE: 25
gcuccggugg uguaguccgg ccaagcauua gggacucuca aucccccgac ucggguccaa 60
aucccgaccg gagcacca 78

<210> SEQ ID NO 26
<211> LENGTH: 78
<212> TYPE: RNA
<213> ORGANISM: Thermoplasma volcanium

<400> SEQUENCE: 26
gcuccggugg uguaguccgg acaagcauau cggccuuucg agccgacgac cuggguccaa 60
aucccggccg gagcacca 78

<210> SEQ ID NO 27
<211> LENGTH: 78
<212> TYPE: RNA
<213> ORGANISM: artificial
<220> FEATURE:
<223> OTHER INFORMATION: consensus tRNA

<400> SEQUENCE: 27
gcyccggugg uguagcccgg ccaakcaugc gggccuyucg agcccgcgac ccggguucaa 60
aucccggccg grgcacca 78

<210> SEQ ID NO 28
<211> LENGTH: 78
<212> TYPE: RNA
<213> ORGANISM: artificial
<220> FEATURE:
<223> OTHER INFORMATION: mutant tRNA

<400> SEQUENCE: 28
gccccggugg uguagcccgg ccaagcaugc gggccucuaa agcccgcgac ccggguucaa 60
aucccggccg gggcacca 78

<210> SEQ ID NO 29
<211> LENGTH: 76
<212> TYPE: RNA
<213> ORGANISM: Aeropyrum pernix

<400> SEQUENCE: 29
agccgggucg ucuagcggcc caggaugcgg ggcucuggcc cccgugaccg ggguucgaau 60
ccccgcccgg cuacca 76

<210> SEQ ID NO 30

-continued

<211> LENGTH: 76
<212> TYPE: RNA
<213> ORGANISM: Aeropyrum pernix

<400> SEQUENCE: 30
agccgggucg ucuagcggcc caggaugcgg gguuuuggcc cccgugaccc ggguucgaau 60
cccggcccgg cuacca 76

<210> SEQ ID NO 31
<211> LENGTH: 76
<212> TYPE: RNA
<213> ORGANISM: Archaeoglobus fulgidus

<400> SEQUENCE: 31
agccccgugg gguagcgguc aauccugccg gacucuggau ccggcgacgc cgguucgaau 60
ccggccgggg cuacca 76

<210> SEQ ID NO 32
<211> LENGTH: 76
<212> TYPE: RNA
<213> ORGANISM: Archaeoglobus fulgidus

<400> SEQUENCE: 32
agccccgugg uguagcgguc aaucaugcgg gccuuuggag cccgcgaccg ggguucgaau 60
ccccgcgggg cuacca 76

<210> SEQ ID NO 33
<211> LENGTH: 76
<212> TYPE: RNA
<213> ORGANISM: Halobacterium sp.

<400> SEQUENCE: 33
agucccguag gguaguggcc aauccugaag ccuucugggg gcuucgacgg aaguucgaau 60
cuucccggga cuacca 76

<210> SEQ ID NO 34
<211> LENGTH: 76
<212> TYPE: RNA
<213> ORGANISM: Halobacterium sp.

<400> SEQUENCE: 34
agucccgugg uguaguggcc aaucauaugg gccuuuggag cccacgacgg cgguucgaau 60
ccgcccggga cuacca 76

<210> SEQ ID NO 35
<211> LENGTH: 75
<212> TYPE: RNA
<213> ORGANISM: Methanobacterium thermautotrophicus

<400> SEQUENCE: 35
agucccgugg gguaauggca auccugaugg acucuggauc caucgauagc gguucgacuc 60
cgcucgggac uacca 75

<210> SEQ ID NO 36
<211> LENGTH: 75
<212> TYPE: RNA
<213> ORGANISM: Methanobacterium thermautotrophicus

<400> SEQUENCE: 36
agucccgugg gguaguggua auccugcugg gcuuuggacc cggcgacagc gguucgacuc 60

-continued cgcucgggac uacca 75

<210> SEQ ID NO 37
<211> LENGTH: 76
<212> TYPE: RNA
<213> ORGANISM: Methanococcus jannaschii

<400> SEQUENCE: 37
agcccggugg uguaguggcc uaucauccgg ggcuuuggac cccgggaccg cgguucgaau 60
ccgcgccggg cuacca 76

<210> SEQ ID NO 38
<211> LENGTH: 76
<212> TYPE: RNA
<213> ORGANISM: Methanococcus maripaludis

<400> SEQUENCE: 38
agcccaguag uguaguggcc aaucauccgu gccuuuggag caugggaccg cgguucgaau 60
ccgcgcuggg cuacca 76

<210> SEQ ID NO 39
<211> LENGTH: 76
<212> TYPE: RNA
<213> ORGANISM: Methanopyrus kandleri

<400> SEQUENCE: 39
agggccgugg gguagcgguc uauccugcgg ggcuuuggac cccgcgaccc cgguucaaau 60
ccgggcggcc cuacca 76

<210> SEQ ID NO 40
<211> LENGTH: 76
<212> TYPE: RNA
<213> ORGANISM: Methanosarcina mazei

<400> SEQUENCE: 40
agcccgguag uguagugguc aaucaugcgg gacucuggau ccugcaaccu cgguucgaau 60
ccgugccggg cuacca 76

<210> SEQ ID NO 41
<211> LENGTH: 76
<212> TYPE: RNA
<213> ORGANISM: Methanosarcina mazei

<400> SEQUENCE: 41
aguccuguag gguagugguc aauccuucgg gccuuuggag cccgggacag cgguucgaau 60
ccgcucagga cuacca 76

<210> SEQ ID NO 42
<211> LENGTH: 75
<212> TYPE: RNA
<213> ORGANISM: Pyrobaculum aerophilum

<400> SEQUENCE: 42
agcccggucg ucuagcggcc aggaugcggg gcucuggacc ccguggcccg gguucgaauc 60
ccggccgggc uacca 75

<210> SEQ ID NO 43
<211> LENGTH: 76
<212> TYPE: RNA

-continued

<213> ORGANISM: Pyrobaculum aerophilum

<400> SEQUENCE: 43
agcccggucg ucuagcggcc aaggaugcgg ggcuuuggac cccguggccc ggguucgaau 60
cccggccggg cuacca 76

<210> SEQ ID NO 44
<211> LENGTH: 76
<212> TYPE: RNA
<213> ORGANISM: Pyrococcus abyssi

<400> SEQUENCE: 44
agccccgugg uguagcggcc aagcaugcgg gacucuggau cccgcgaccg ggguucgaau 60
ccccgcgggg cuacca 76

<210> SEQ ID NO 45
<211> LENGTH: 76
<212> TYPE: RNA
<213> ORGANISM: Pyrococcus abyssi

<400> SEQUENCE: 45
agccccgugg uguagcggcc aagcaugcgg gacuuuggau cccgcgaccc ggguucgaau 60
cccggcgggg cuacca 76

<210> SEQ ID NO 46
<211> LENGTH: 76
<212> TYPE: RNA
<213> ORGANISM: Pyrococcus furiosus

<400> SEQUENCE: 46
agccccgugg uguagcggcc aagcaugcgg gacucuggau cccgcgaccg ggguucgaau 60
ccccgcgggg cuacca 76

<210> SEQ ID NO 47
<211> LENGTH: 76
<212> TYPE: RNA
<213> ORGANISM: Pyrococcus furiosus

<400> SEQUENCE: 47
agccccgugg uguagcggcc aagcaugcgg gacuuuggau cccgcgaccc ggguucgaau 60
cccggcgggg cuacca 76

<210> SEQ ID NO 48
<211> LENGTH: 76
<212> TYPE: RNA
<213> ORGANISM: Pyrococcus horikoshii

<400> SEQUENCE: 48
agccccgugg uguagcggcc aagcaugcgg gacucuggau cccgcgaccg ggguucgaau 60
ccccgcgggg cuacca 76

<210> SEQ ID NO 49
<211> LENGTH: 76
<212> TYPE: RNA
<213> ORGANISM: Pyrococcus horikoshii

<400> SEQUENCE: 49
agccccgugg uguagcggcc aagcaugcgg gacuuuggau cccgcgaccc ggguucgaau 60
cccggcgggg cuacca 76

-continued

<210> SEQ ID NO 50
<211> LENGTH: 76
<212> TYPE: RNA
<213> ORGANISM: Sulfolobus solfataricus

<400> SEQUENCE: 50
agccggguag ucuagugguc aaggauccag ggcucuggcc ccugggacca ggguucgaau 60
cccugcccgg cuacca 76

<210> SEQ ID NO 51
<211> LENGTH: 76
<212> TYPE: RNA
<213> ORGANISM: Sulfolobus solfataricus

<400> SEQUENCE: 51
agccggguag ucuagugguc aaggauccag ggcuuuggcc ccugggacca ggguucgaau 60
cccugcccgg cuacca 76

<210> SEQ ID NO 52
<211> LENGTH: 76
<212> TYPE: RNA
<213> ORGANISM: Sulfolobus tokodaii

<400> SEQUENCE: 52
agccgggucg ucuagugguc aaggaucgag ggcucuggcc ccucggaccu ggguucaaau 60
cccagcccgg cuacca 76

<210> SEQ ID NO 53
<211> LENGTH: 76
<212> TYPE: RNA
<213> ORGANISM: Sulfolobus tokodaii

<400> SEQUENCE: 53
agccgggucg ucuagugguc aaggaucgag ggcuuuggcc ccucggaccu ggguucaaau 60
cccagcccgg cuacca 76

<210> SEQ ID NO 54
<211> LENGTH: 76
<212> TYPE: RNA
<213> ORGANISM: Thermoplasma acidophilum

<400> SEQUENCE: 54
agcccugugg uguaguggcc aagcauuaug ggcucuggac ccaucgacgg caguucgaau 60
cugcccaggg cuacca 76

<210> SEQ ID NO 55
<211> LENGTH: 76
<212> TYPE: RNA
<213> ORGANISM: Thermoplasma acidophilum

<400> SEQUENCE: 55
agcccugugg uguaguggac aagcauuuug gacuuuggau ccaaagacgg caguucgaau 60
cugcccaggg cuacca 76

<210> SEQ ID NO 56
<211> LENGTH: 76
<212> TYPE: RNA
<213> ORGANISM: Thermoplasma volcanium -continued

<400> SEQUENCE: 56
agcccugugg uguagcggcc aagcauuaug ggcucuggac ccaucgacgg caguucgaau 60
cugcccaggg cuacca 76

<210> SEQ ID NO 57
<211> LENGTH: 76
<212> TYPE: RNA
<213> ORGANISM: Thermoplasma volcanium

<400> SEQUENCE: 57
agcccugugg uguaguggac aagcauuuug gacuuuggau ccaacgacgg caguucgaau 60
cugcccaggg cuacca 76

<210> SEQ ID NO 58
<211> LENGTH: 76
<212> TYPE: RNA
<213> ORGANISM: artificial
<220> FEATURE:
<223> OTHER INFORMATION: consensus tRNA

<400> SEQUENCE: 58
agccccgugg uguagyggcc aagcaugcgg grcuyuggay cccgcgaccg sgguucgaau 60
ccscgcgggg cuacca 76

<210> SEQ ID NO 59
<211> LENGTH: 76
<212> TYPE: RNA
<213> ORGANISM: artificial
<220> FEATURE:
<223> OTHER INFORMATION: mutant tRNA

<400> SEQUENCE: 59
agccccgugg uguagcggcc aagcaugcgg ggcucuaaac cccgcgaccg ggguucgaau 60
ccccgcgggg cuacca 76

<210> SEQ ID NO 60
<211> LENGTH: 76
<212> TYPE: RNA
<213> ORGANISM: artificial
<220> FEATURE:
<223> OTHER INFORMATION: mutant tRNA

<400> SEQUENCE: 60
agccccgugg uguagcggcc aagcacgcgg ggcucuaaac cccgcgaccg ggguucgaau 60
ccccgcgggg cuacca 76

<210> SEQ ID NO 61
<211> LENGTH: 78
<212> TYPE: RNA
<213> ORGANISM: artificial
<220> FEATURE:
<223> OTHER INFORMATION: consensus tRNA

<400> SEQUENCE: 61
gcyccggugg uguagcccgg ccaakcaugc gggccuyucg agcccgcgac ccggguucaa 60
aucccggccg grgcacca 78

<210> SEQ ID NO 62
<211> LENGTH: 76
<212> TYPE: RNA
<213> ORGANISM: artificial

-continued

<220> FEATURE:
<223> OTHER INFORMATION: consensus tRNA

<400> SEQUENCE: 62
agccccgugg uguagyggcc aagcaugcgg grcuyuggay cccgcgaccg sgguucgaau 60
ccscgcgggg cuacca 76

<210> SEQ ID NO 63
<211> LENGTH: 78
<212> TYPE: RNA
<213> ORGANISM: artificial
<220> FEATURE:
<223> OTHER INFORMATION: mutant tRNA

<400> SEQUENCE: 63
gccccggugg uguagcccgg ccaagcaugc gggccucuaa agcccgcgac ccggguucaa 60
aucccggccg gggcacca 78

<210> SEQ ID NO 64
<211> LENGTH: 76
<212> TYPE: RNA
<213> ORGANISM: artificial
<220> FEATURE:
<223> OTHER INFORMATION: mutant tRNA

<400> SEQUENCE: 64
agccccgugg uguagcggcc aagcaugcgg ggcucuaaac cccgcgaccg ggguucgaau 60
ccccgcgggg cuacca 76

<210> SEQ ID NO 65
<211> LENGTH: 76
<212> TYPE: RNA
<213> ORGANISM: artificial
<220> FEATURE:
<223> OTHER INFORMATION: mutant tRNA

<400> SEQUENCE: 65
agccccgugg uguagcggcc aagcacgcgg ggcucuaaac cccgcgaccg ggguucgaau 60
ccccgcgggg cuacca 76

<210> SEQ ID NO 66
<211> LENGTH: 78
<212> TYPE: RNA
<213> ORGANISM: artificial
<220> FEATURE:
<223> OTHER INFORMATION: mutant tRNA
<220> FEATURE:
<221> NAME/KEY: misc_feature
<222> LOCATION: (10)..(10)
<223> OTHER INFORMATION: n is a, c, g, or u
<220> FEATURE:
<221> NAME/KEY: misc_feature
<222> LOCATION: (28)..(28)
<223> OTHER INFORMATION: n is a, c, g, or u

<400> SEQUENCE: 66
gccccggugn uguagcccgg ccaagcangc gggccucuaa agcccgcgac ccggguucaa 60
aucccggccg gggcacca 78

<210> SEQ ID NO 67
<211> LENGTH: 78
<212> TYPE: RNA
<213> ORGANISM: artificial
<220> FEATURE:

-continued

<223> OTHER INFORMATION: mutant tRNA

<400> SEQUENCE: 67
gccccggugg uguagcccgg ccaagcacgc gggccucuaa agcccgcgac ccggguucaa 60
aucccggccg gggcacca 78

<210> SEQ ID NO 68
<211> LENGTH: 1656
<212> TYPE: DNA
<213> ORGANISM: Archaeoglobus fulgidus

<400> SEQUENCE: 68
gtgaaagaag tcataatgaa atacgtagtt cagaacgccg caaagtacgg aaaagccagt 60
gaaaaggctg taatggggaa ggtgatggca gaaaatccag aactcagaaa aaaagctaaa 120
gaggtccttg aactcgtaaa ggagtgcatt accgagttcg aagcgctttc tgaagaagta 180
aggaaggagc taatcaaaaa atacagcatg gatagcgaag ctaaaaggga gttggagacg 240
aagaagcttc cagagcttga gggggctgag aaagggaaag ttgtgatgag attcgctcct 300
aatccaaacg gtccacctac actcggttct gctaggggga taatcgtcaa cggtgaatac 360
gcgaagatgt acgaagggaa gtacattatc aggtttgacg atacagaccc cagaaccaag 420
agaccgatga ttgaggccta cgagtggtac ctagaggaca ttgaatggct cggttacaag 480
cctgacgagg ttatttacgc ctcaagaagg attcccatct actacgatta tgcaagaaag 540
cttatagaaa tgggcaaagc ctacacctgc ttctgcagtc aggaggagtt caagaagttc 600
agggacagtg gtgaggagtg cccacacaga aacatcagcg tcgaggatac acttgaagtc 660
tgggagagaa tgcttgaagg agactatgag gaaggagaag tcgttcttag aattaagacg 720
gatatgcgcc acaaggatcc ggcaataagg gactgggtgg ctttcaggat aataaaggaa 780
tcacatcctc tcgttgggga taaatatgtt gtctatccca cactcgattt tgaatctgct 840
atagaggatc accttttagg cataacgcac attatcaggg gtaaggactt aattgattct 900
gagaggaggc agagatacat ctacgagtat tttggctgga tttaccccat tacaaagcac 960
tggggcaggg ttaaaatctt cgaattcggg aagctatcga cttcttcaat taagaaggat 1020
attgaaaggg gtaagtatga gggctgggat gacccaaggc tgccaacctt gagagccttc 1080
aggaggagag gatttgagcc tgaagccata aagagcttct tcctttcgct gggagttggc 1140
gagaacgacg tttccgtcag tctcaagaat ctttacgctg agaacaggaa aatcatcgat 1200
cgcaaggcaa accgttactt tttcatttgg gggcccgtga agattgaaat cgttaacctg 1260
ccggagaaga aagaggtcga gctcccgctg aatccgcaca cgggcgagaa gagaaggctg 1320
aaaggtgaaa gaactatata tgttacaaaa gacgacttcg agaggttgaa agggcaggtt 1380
gtaaggctga aggacttctg caacgttctg cttgacgaga aggcagagtt catgggtttt 1440
gagcttgagg gggtcaagaa ggggaagaac ataatccact ggcttcctga gagcgaggct 1500
atcaagggca aggttatcgg cgaaagggaa gcggaagggc ttgtggagag aaacgcagtt 1560
agagatgtcg ggaaagtcgt gcagttcgag agatttgctt tctgtaaagt agagtctgct 1620
gacgaggaac tggtcgcggt gtacacgcac ccgtga 1656

<210> SEQ ID NO 69
<211> LENGTH: 551
<212> TYPE: PRT
<213> ORGANISM: Archaeoglobus fulgidus

<400> SEQUENCE: 69

-continued

```
Val Lys Glu Val Ile Met Lys Tyr Val Val Gln Asn Ala Ala Lys Tyr
1               5                   10                  15

Gly Lys Ala Ser Glu Lys Ala Val Met Gly Lys Val Met Ala Glu Asn
            20                  25                  30

Pro Glu Leu Arg Lys Lys Ala Lys Glu Val Leu Glu Leu Val Lys Glu
        35                  40                  45

Cys Ile Thr Glu Phe Glu Ala Leu Ser Glu Glu Val Arg Lys Glu Leu
    50                  55                  60

Ile Lys Lys Tyr Ser Met Asp Ser Glu Ala Lys Arg Glu Leu Glu Thr
65                  70                  75                  80

Lys Lys Leu Pro Glu Leu Glu Gly Ala Glu Lys Gly Lys Val Val Met
                85                  90                  95

Arg Phe Ala Pro Asn Pro Asn Gly Pro Pro Thr Leu Gly Ser Ala Arg
            100                 105                 110

Gly Ile Ile Val Asn Gly Glu Tyr Ala Lys Met Tyr Glu Gly Lys Tyr
        115                 120                 125

Ile Ile Arg Phe Asp Asp Thr Asp Pro Arg Thr Lys Arg Pro Met Ile
    130                 135                 140

Glu Ala Tyr Glu Trp Tyr Leu Glu Asp Ile Glu Trp Leu Gly Tyr Lys
145                 150                 155                 160

Pro Asp Glu Val Ile Tyr Ala Ser Arg Arg Ile Pro Ile Tyr Tyr Asp
                165                 170                 175

Tyr Ala Arg Lys Leu Ile Glu Met Gly Lys Ala Tyr Thr Cys Phe Cys
            180                 185                 190

Ser Gln Glu Glu Phe Lys Lys Phe Arg Asp Ser Gly Glu Glu Cys Pro
        195                 200                 205

His Arg Asn Ile Ser Val Glu Asp Thr Leu Glu Val Trp Glu Arg Met
    210                 215                 220

Leu Glu Gly Asp Tyr Glu Glu Gly Glu Val Val Leu Arg Ile Lys Thr
225                 230                 235                 240

Asp Met Arg His Lys Asp Pro Ala Ile Arg Asp Trp Val Ala Phe Arg
                245                 250                 255

Ile Ile Lys Glu Ser His Pro Leu Val Gly Asp Lys Tyr Val Val Tyr
            260                 265                 270

Pro Thr Leu Asp Phe Glu Ser Ala Ile Glu Asp His Leu Leu Gly Ile
        275                 280                 285

Thr His Ile Ile Arg Gly Lys Asp Leu Ile Asp Ser Glu Arg Arg Gln
    290                 295                 300

Arg Tyr Ile Tyr Glu Tyr Phe Gly Trp Ile Tyr Pro Ile Thr Lys His
305                 310                 315                 320

Trp Gly Arg Val Lys Ile Phe Glu Phe Gly Lys Leu Ser Thr Ser Ser
                325                 330                 335

Ile Lys Lys Asp Ile Glu Arg Gly Lys Tyr Glu Gly Trp Asp Asp Pro
            340                 345                 350

Arg Leu Pro Thr Leu Arg Ala Phe Arg Arg Arg Gly Phe Glu Pro Glu
        355                 360                 365

Ala Ile Lys Ser Phe Phe Leu Ser Leu Gly Val Gly Glu Asn Asp Val
    370                 375                 380

Ser Val Ser Leu Lys Asn Leu Tyr Ala Glu Asn Arg Lys Ile Ile Asp
385                 390                 395                 400

Arg Lys Ala Asn Arg Tyr Phe Phe Ile Trp Gly Pro Val Lys Ile Glu
                405                 410                 415
```

-continued

```
Ile Val Asn Leu Pro Glu Lys Lys Glu Val Glu Leu Pro Leu Asn Pro
            420                 425                 430

His Thr Gly Glu Lys Arg Arg Leu Lys Gly Glu Arg Thr Ile Tyr Val
        435                 440                 445

Thr Lys Asp Asp Phe Glu Arg Leu Lys Gly Gln Val Val Arg Leu Lys
    450                 455                 460

Asp Phe Cys Asn Val Leu Leu Asp Glu Lys Ala Glu Phe Met Gly Phe
465                 470                 475                 480

Glu Leu Glu Gly Val Lys Lys Gly Lys Asn Ile Ile His Trp Leu Pro
                485                 490                 495

Glu Ser Glu Ala Ile Lys Gly Lys Val Ile Gly Glu Arg Glu Ala Glu
            500                 505                 510

Gly Leu Val Glu Arg Asn Ala Val Arg Asp Val Gly Lys Val Val Gln
        515                 520                 525

Phe Glu Arg Phe Ala Phe Cys Lys Val Glu Ser Ala Asp Glu Glu Leu
    530                 535                 540

Val Ala Val Tyr Thr His Pro
545                 550


<210> SEQ ID NO 70
<211> LENGTH: 1635
<212> TYPE: DNA
<213> ORGANISM: Aeuropyrum pernix

<400> SEQUENCE: 70

atgtcaatgc tcctagggga ccatcctgag cttaggagta gggcgaggga gatagcctcc     60

ctggctgcaa gggtcgtgga gcaggtgaac agcatgcctg ctggcgagca gaagaggctc    120

ctctcagaac agtatccgga gctagcgagg tttgaagagc agcgcgagaa aggcgataaa    180

ggcctacccc cgctgcccgg ggccgtggaa ggcagggtca agctgaggtt cgccccccaac    240

ccagactttg tgatacacat gggcaacgct aggccggcca tagtgaacca cgagtacgcc    300

aggatgtata aggggaggat ggtgctgcgg ttcgaagaca cagaccctag gacaaagact    360

cccctacggg aggcgtacga cctcatccgc caggacctca agtggcttgg cgtttcctgg    420

gacgaggagt acatccagag cctcaggatg gaggtcttct acagcgtagc cagaagggct    480

atagagcggg ggtgcgccta cgtcgacaac tgtgggagag agggtaagga gctgctctcg    540

cgtggagagt attgtccgac cagggatctt ggccccgagg ataatctgga gctgtttgag    600

aagatgcttg aaggagagtt ttacgagggg gaggctgttg tgaggatgaa gacggacccg    660

cgccacccca accccagcct gagggactgg gtggccatga ggattataga cacggagaaa    720

cacccccacc ccctcgtggg gagcaggtac ctggtgtggc cgacctataa cttcgccgtc    780

agcgtcgacg accacatgat ggagataacc cacgtgctca ggggtaagga gcaccagctg    840

aacaccgaga agcagcttgc cgtctacagg tgtatgggct ggaggccgcc gtacttcatc    900

cacttcggca ggctaaagct ggaggggttt atactgagca agagcaagat aagaaagctc    960

ctcgaagaga ggccaggaga gttcatgggc tacgacgacc cccgcttcgg cacgatagcc   1020

gggctgagga ggaggggtgt gctggcggag gccataagac agataatact cgaggtgggg   1080

gtcaagccca cggacgctac aataagctgg gcaaacctgg cggccgctaa taggaagctg   1140

ctggacgagc gggcggacag gataatgtat gtcgaagacc ccgttgagat ggaggtcgag   1200

ctggcccagg tggagtgcag agccgcggag ataccgttcc acccgagccg cccccagagg   1260

aagaggagga taaccttgtg cacgggggac aaggttctcc tcacaaggga ggacgcagta   1320
```

-continued

```
gagggtaggc aactgaggct catgggccta tcaaacttca ccgtcagcca aggcatattg   1380

agggaggtgg atcccagcct cgagtatgcg aggagaatga agctacctat agtacaatgg   1440

gtgaagaagg gcggagaagc tagcgtagag gtactcgagc ccgtcgagct ggagctcagg   1500

aggcaccagg gctacgctga ggacgctatt aggggctatg ggttgacag ccgcctacag    1560

tttgtaaggt acggttttgt gagggtggac agcgtggaag acggggtcta cagggtgata   1620

tacacacaca agtag                                                    1635
```

<210> SEQ ID NO 71
<211> LENGTH: 544
<212> TYPE: PRT
<213> ORGANISM: Aeuropyrum pernix

<400> SEQUENCE: 71

```
Met Ser Met Leu Leu Gly Asp His Pro Glu Leu Arg Ser Arg Ala Arg
1               5                   10                  15

Glu Ile Ala Ser Leu Ala Ala Arg Val Val Glu Gln Val Asn Ser Met
            20                  25                  30

Pro Ala Gly Glu Gln Lys Arg Leu Leu Ser Glu Gln Tyr Pro Glu Leu
        35                  40                  45

Ala Arg Phe Glu Glu Gln Arg Glu Lys Gly Asp Lys Gly Leu Pro Pro
    50                  55                  60

Leu Pro Gly Ala Val Glu Gly Arg Val Lys Leu Arg Phe Ala Pro Asn
65                  70                  75                  80

Pro Asp Phe Val Ile His Met Gly Asn Ala Arg Pro Ala Ile Val Asn
                85                  90                  95

His Glu Tyr Ala Arg Met Tyr Lys Gly Arg Met Val Leu Arg Phe Glu
            100                 105                 110

Asp Thr Asp Pro Arg Thr Lys Thr Pro Leu Arg Glu Ala Tyr Asp Leu
        115                 120                 125

Ile Arg Gln Asp Leu Lys Trp Leu Gly Val Ser Trp Asp Glu Glu Tyr
    130                 135                 140

Ile Gln Ser Leu Arg Met Glu Val Phe Tyr Ser Val Ala Arg Arg Ala
145                 150                 155                 160

Ile Glu Arg Gly Cys Ala Tyr Val Asp Asn Cys Gly Arg Glu Gly Lys
                165                 170                 175

Glu Leu Leu Ser Arg Gly Glu Tyr Cys Pro Thr Arg Asp Leu Gly Pro
            180                 185                 190

Glu Asp Asn Leu Glu Leu Phe Glu Lys Met Leu Glu Gly Glu Phe Tyr
        195                 200                 205

Glu Gly Glu Ala Val Val Arg Met Lys Thr Asp Pro Arg His Pro Asn
    210                 215                 220

Pro Ser Leu Arg Asp Trp Val Ala Met Arg Ile Ile Asp Thr Glu Lys
225                 230                 235                 240

His Pro His Pro Leu Val Gly Ser Arg Tyr Leu Val Trp Pro Thr Tyr
                245                 250                 255

Asn Phe Ala Val Ser Val Asp Asp His Met Met Glu Ile Thr His Val
            260                 265                 270

Leu Arg Gly Lys Glu His Gln Leu Asn Thr Glu Lys Gln Leu Ala Val
        275                 280                 285

Tyr Arg Cys Met Gly Trp Arg Pro Pro Tyr Phe Ile His Phe Gly Arg
    290                 295                 300

Leu Lys Leu Glu Gly Phe Ile Leu Ser Lys Ser Lys Ile Arg Lys Leu
305                 310                 315                 320
```

-continued

```
Leu Glu Glu Arg Pro Gly Glu Phe Met Gly Tyr Asp Asp Pro Arg Phe
                325                 330                 335

Gly Thr Ile Ala Gly Leu Arg Arg Arg Gly Val Leu Ala Glu Ala Ile
            340                 345                 350

Arg Gln Ile Ile Leu Glu Val Gly Val Lys Pro Thr Asp Ala Thr Ile
        355                 360                 365

Ser Trp Ala Asn Leu Ala Ala Ala Asn Arg Lys Leu Leu Asp Glu Arg
    370                 375                 380

Ala Asp Arg Ile Met Tyr Val Glu Asp Pro Val Glu Met Glu Val Glu
385                 390                 395                 400

Leu Ala Gln Val Glu Cys Arg Ala Ala Glu Ile Pro Phe His Pro Ser
                405                 410                 415

Arg Pro Gln Arg Lys Arg Arg Ile Thr Leu Cys Thr Gly Asp Lys Val
            420                 425                 430

Leu Leu Thr Arg Glu Asp Ala Val Glu Gly Arg Gln Leu Arg Leu Met
        435                 440                 445

Gly Leu Ser Asn Phe Thr Val Ser Gln Gly Ile Leu Arg Glu Val Asp
    450                 455                 460

Pro Ser Leu Glu Tyr Ala Arg Arg Met Lys Leu Pro Ile Val Gln Trp
465                 470                 475                 480

Val Lys Lys Gly Gly Glu Ala Ser Val Glu Val Leu Glu Pro Val Glu
                485                 490                 495

Leu Glu Leu Arg Arg His Gln Gly Tyr Ala Glu Asp Ala Ile Arg Gly
            500                 505                 510

Tyr Gly Val Asp Ser Arg Leu Gln Phe Val Arg Tyr Gly Phe Val Arg
        515                 520                 525

Val Asp Ser Val Glu Asp Gly Val Tyr Arg Val Ile Tyr Thr His Lys
    530                 535                 540
```

<210> SEQ ID NO 72
<211> LENGTH: 1716
<212> TYPE: DNA
<213> ORGANISM: Methanosarcina mazeii

<400> SEQUENCE: 72

```
atgaccttaa gtcctgaaga tattaaaata attgaaaaat acgctcttca aaatgctgta      60

aaatacggaa aagccccaca gcccaaagct gttatgggta aagttatggg ggaatgtccc     120

cagttgaggg ctgaccccag cggggtatct gctgcccttg aaaatatagt ttcagaaatt     180

gctaaaggaa accctgaagc ctgggaagcc cgcctgtcgg aaatcgctcc cgagcttata     240

gaggctctga gtgtaaagaa agagcctgac aaaggcttaa aacctcttga gggagccgaa     300

accggtaagg ttgtaatgcg ctttgcccca aatcccaacg gacccgcaac cctgggaagt     360

tcaaggggaa tggttgtcaa ttccgagtat gtaaaagtgt ataaaggaaa gtttatcctg     420

cgctttgatg acactgaccc tgatataaag cgtcccatgc tcgaagccta tgactggtac     480

atggacgact ttaaatggct cggggttgtg cctgaccagg ttgtacgtgc ctctgaccgt     540

ttcccgattt attacgatta tgcaagaaaa ctgattgaga tgggaaaagc ctatgtctgt     600

ttctgtaaag gagaagactt caaaaggtta aaagactcca aaaaggcctg ccctcacagg     660

gacacagacc ctgaagaaaa ccttatgcac tgggaaaaga tgcttgccgg agaatatgaa     720

gaccagcagg ctgttctgcg cataaagacc gatatagagc acaaagaccc tgcacttcgg     780

gactggggag cattcaggat tagaaaaatg tcccacccac gccctgagat tggaaataaa     840
```

-continued

```
tacatcgtct ggccccttct ggactttgca ggtgctatcg aagaccacga gctcggtatg    900

acccacatca tccggggtaa agaccttatc gacagtgaaa aacggcagac atacatttac    960

aaatacttcg gctggacata cccgaaaaca actcactggg gcagggtaaa gatccatgag   1020

ttcggaaagt tcagcacaag taccctgcgt aaagctatcg aatccggaga atacagcggc   1080

tgggacgacc cccgcctgcc gacaataagg gcaatcaggc gccgtggaat tagggctgaa   1140

gctctcaaaa agttcatgat agaaatggga gtcgggatga ccgatgtgag catcagcatg   1200

gaatctcttt atgccgagaa ccgcaaaatc gtggacccgg ttgcaaaccg ctatttcttt   1260

gtctggaacc ctgtggagct tgaaattgaa ggtatgaaac ctgtggtcgc aaaggtcccc   1320

cgtcacccaa cagaccatgc aagaggaatg agggaaatct ctatcgaaaa taaggttctt   1380

gtctgtgccg aggacattga aaagctcaat gtaggttctg tcctccgctt aaaagatctc   1440

tgcaacgttg aaattacttc cctttccccg ctgcgggtta agcgctccga aacctctctc   1500

gaagacctca aaaaagcaaa aggaaaaatc atccactggg tgccggttga tggaattcct   1560

gtgaaagtct gcgggccaga gggcgatatc gaagggacag gagaacgcgg gatcgagacc   1620

gagcttgata atattgtcca gtttgaacgc ttcggtttct gcaggatcga cgccgtagac   1680

ggagaaaatg tcgtggcgta ctttgctcac aaatga                             1716
```

<210> SEQ ID NO 73
<211> LENGTH: 571
<212> TYPE: PRT
<213> ORGANISM: Methanosarcina mazeii

<400> SEQUENCE: 73

```
Met Thr Leu Ser Pro Glu Asp Ile Lys Ile Ile Glu Lys Tyr Ala Leu
1               5                   10                  15

Gln Asn Ala Val Lys Tyr Gly Lys Ala Pro Gln Pro Lys Ala Val Met
            20                  25                  30

Gly Lys Val Met Gly Glu Cys Pro Gln Leu Arg Ala Asp Pro Ser Gly
        35                  40                  45

Val Ser Ala Ala Leu Glu Asn Ile Val Ser Glu Ile Ala Lys Gly Asn
    50                  55                  60

Pro Glu Ala Trp Glu Ala Arg Leu Ser Glu Ile Ala Pro Glu Leu Ile
65                  70                  75                  80

Glu Ala Leu Ser Val Lys Lys Glu Pro Asp Lys Gly Leu Lys Pro Leu
                85                  90                  95

Glu Gly Ala Glu Thr Gly Lys Val Val Met Arg Phe Ala Pro Asn Pro
            100                 105                 110

Asn Gly Pro Ala Thr Leu Gly Ser Ser Arg Gly Met Val Val Asn Ser
        115                 120                 125

Glu Tyr Val Lys Val Tyr Lys Gly Lys Phe Ile Leu Arg Phe Asp Asp
    130                 135                 140

Thr Asp Pro Asp Ile Lys Arg Pro Met Leu Glu Ala Tyr Asp Trp Tyr
145                 150                 155                 160

Met Asp Asp Phe Lys Trp Leu Gly Val Val Pro Asp Gln Val Val Arg
                165                 170                 175

Ala Ser Asp Arg Phe Pro Ile Tyr Tyr Asp Tyr Ala Arg Lys Leu Ile
            180                 185                 190

Glu Met Gly Lys Ala Tyr Val Cys Phe Cys Lys Gly Glu Asp Phe Lys
        195                 200                 205

Arg Leu Lys Asp Ser Lys Lys Ala Cys Pro His Arg Asp Thr Asp Pro
    210                 215                 220
```

-continued

```
Glu Glu Asn Leu Met His Trp Glu Lys Met Leu Ala Gly Glu Tyr Glu
225                 230                 235                 240

Asp Gln Gln Ala Val Leu Arg Ile Lys Thr Asp Ile Glu His Lys Asp
                245                 250                 255

Pro Ala Leu Arg Asp Trp Gly Ala Phe Arg Ile Arg Lys Met Ser His
            260                 265                 270

Pro Arg Pro Glu Ile Gly Asn Lys Tyr Ile Val Trp Pro Leu Leu Asp
        275                 280                 285

Phe Ala Gly Ala Ile Glu Asp His Glu Leu Gly Met Thr His Ile Ile
    290                 295                 300

Arg Gly Lys Asp Leu Ile Asp Ser Glu Lys Arg Gln Thr Tyr Ile Tyr
305                 310                 315                 320

Lys Tyr Phe Gly Trp Thr Tyr Pro Lys Thr Thr His Trp Gly Arg Val
                325                 330                 335

Lys Ile His Glu Phe Gly Lys Phe Ser Thr Ser Thr Leu Arg Lys Ala
            340                 345                 350

Ile Glu Ser Gly Glu Tyr Ser Gly Trp Asp Asp Pro Arg Leu Pro Thr
        355                 360                 365

Ile Arg Ala Ile Arg Arg Arg Gly Ile Arg Ala Glu Ala Leu Lys Lys
    370                 375                 380

Phe Met Ile Glu Met Gly Val Gly Met Thr Asp Val Ser Ile Ser Met
385                 390                 395                 400

Glu Ser Leu Tyr Ala Glu Asn Arg Lys Ile Val Asp Pro Val Ala Asn
                405                 410                 415

Arg Tyr Phe Phe Val Trp Asn Pro Val Glu Leu Glu Ile Glu Gly Met
            420                 425                 430

Lys Pro Val Val Ala Lys Val Pro Arg His Pro Thr Asp His Ala Arg
        435                 440                 445

Gly Met Arg Glu Ile Ser Ile Glu Asn Lys Val Leu Val Cys Ala Glu
    450                 455                 460

Asp Ile Glu Lys Leu Asn Val Gly Ser Val Leu Arg Leu Lys Asp Leu
465                 470                 475                 480

Cys Asn Val Glu Ile Thr Ser Leu Ser Pro Leu Arg Val Lys Arg Ser
                485                 490                 495

Glu Thr Ser Leu Glu Asp Leu Lys Lys Ala Lys Gly Lys Ile Ile His
            500                 505                 510

Trp Val Pro Val Asp Gly Ile Pro Val Lys Val Cys Gly Pro Glu Gly
        515                 520                 525

Asp Ile Glu Gly Thr Gly Glu Arg Gly Ile Glu Thr Glu Leu Asp Asn
    530                 535                 540

Ile Val Gln Phe Glu Arg Phe Gly Phe Cys Arg Ile Asp Ala Val Asp
545                 550                 555                 560

Gly Glu Asn Val Val Ala Tyr Phe Ala His Lys
                565                 570
```

<210> SEQ ID NO 74
<211> LENGTH: 1662
<212> TYPE: DNA
<213> ORGANISM: Methanobacterium thermoautotrophicum

<400> SEQUENCE: 74

```
gtggtgccag tggaggacct tgtctacagg tacgcactcc tgaacgctgt gaaacacagg      60

ggaagggcaa acccgggggc cgtcatgggg gccgtcatga gcaacgaacc tgaactcagg     120
```

-continued

```
aagatggcgc cccaggttaa ggaagcagtt gaggccgctg ttgagagggt taacagttta    180

agccccgagg agcagcagca ggagatggag aggctgggcc ttgagatcac cgagaggaaa    240

cagaagaagc ggaagggtct aagggaactg gccggggtga agggtgaggt ggtcctcagg    300

ttcgcccccca accccagcgg acccctccac ataggccatg caagggccgc gatcctcaac    360

catgaatatg caaggaaata tgacggcagg ctcatcctca ggatagagga cacggacccc    420

cgcagggttg acccggaggc ctacgatatg attccagccg accttgagtg gctgggcgtt    480

gaatgggatg agacagttat ccagagcgac cgcatggaaa cctactatga gtacacagag    540

aaactcatag agaggggtgg tgcgtatgta tgcacatgca ggccggagga gttcagggaa    600

ctcaagaaca ggggagaggc ctgtcactgc aggtcccttg gtttcaggga gaacctccag    660

cgatggaggg aaatgttcga gatgaaggag ggctcagccg ttgtgagggt taaaacggac    720

ctgaaccacc caaaccctgc cataagagac tgggtctcaa tgaggatcgt tgaggcagag    780

cacccacgca ccggtacacg ctacagggtc taccccatga tgaacttctc agtggcggtt    840

gatgaccacc tccttggcgt gacacacgtc ctgaggggta aggaccacct ggcaaacaga    900

gagaagcagg agtacctcta caggcacctt ggctgggagc cccccgaatt catacactac    960

gggcgcctga agatggacga cgttgcactc agcacctcgg gggcccgtga gggcatcctc   1020

aggggtgagt attctggatg ggacgaccca cgcctcggaa ccctgagggc cattgcaagg   1080

aggggtatac gaccggaggc cataagaaag ttaatggttg aaatcggcgt aaagatagca   1140

gattccacaa tgagctggaa gaagatctac ggcctcaaca ggagcatcct cgaagaggag   1200

gccaggaggt acttctttgc tgcagatcct gttaaacttg aagtggtggg tttacccgga   1260

cctgtcaggg ttgaaaggcc cctacacccg gaccaccctg aaatcgggaa cagggtactt   1320

gaactgaggg gtgaggtgta cctgccgggc gatgaccttg ggaaggacc gctgcgcctc   1380

atagacgcgg ttaacgtgat ctactctggg ggtgaactga ggtaccacag tgagggcatc   1440

gaggaggccc gtgaactcgg cgcttcaatg atacactggg tccctgcaga gtccgccctt   1500

gaggccgagg tcatcatgcc ggacgcctcc agggtgaggg gagtcatcga ggctgacgca   1560

tcagaactgg aggttgatga tgttgtgcag cttgagaggt tcggcttcgc ccgcctggat   1620

tctgcaggcc caggaatggt cttctactat gcccacaaat ga                      1662
```

```
<210> SEQ ID NO 75
<211> LENGTH: 553
<212> TYPE: PRT
<213> ORGANISM: Methanobacterium thermoautotrophicum

<400> SEQUENCE: 75

Val Val Pro Val Glu Asp Leu Val Tyr Arg Tyr Ala Leu Leu Asn Ala
1               5                   10                  15

Val Lys His Arg Gly Arg Ala Asn Pro Gly Ala Val Met Gly Ala Val
            20                  25                  30

Met Ser Asn Glu Pro Glu Leu Arg Lys Met Ala Pro Gln Val Lys Glu
        35                  40                  45

Ala Val Glu Ala Ala Val Glu Arg Val Asn Ser Leu Ser Pro Glu Glu
    50                  55                  60

Gln Gln Gln Glu Met Glu Arg Leu Gly Leu Glu Ile Thr Glu Arg Lys
65                  70                  75                  80

Gln Lys Lys Arg Lys Gly Leu Arg Glu Leu Ala Gly Val Lys Gly Glu
                85                  90                  95

Val Val Leu Arg Phe Ala Pro Asn Pro Ser Gly Pro Leu His Ile Gly
```

-continued

```
            100                 105                 110

His Ala Arg Ala Ala Ile Leu Asn His Glu Tyr Ala Arg Lys Tyr Asp
        115                 120                 125

Gly Arg Leu Ile Leu Arg Ile Glu Asp Thr Asp Pro Arg Arg Val Asp
    130                 135                 140

Pro Glu Ala Tyr Asp Met Ile Pro Ala Asp Leu Glu Trp Leu Gly Val
145                 150                 155                 160

Glu Trp Asp Glu Thr Val Ile Gln Ser Asp Arg Met Glu Thr Tyr Tyr
                165                 170                 175

Glu Tyr Thr Glu Lys Leu Ile Glu Arg Gly Gly Ala Tyr Val Cys Thr
            180                 185                 190

Cys Arg Pro Glu Glu Phe Arg Glu Leu Lys Asn Arg Gly Glu Ala Cys
        195                 200                 205

His Cys Arg Ser Leu Gly Phe Arg Glu Asn Leu Gln Arg Trp Arg Glu
    210                 215                 220

Met Phe Glu Met Lys Glu Gly Ser Ala Val Val Arg Val Lys Thr Asp
225                 230                 235                 240

Leu Asn His Pro Asn Pro Ala Ile Arg Asp Trp Val Ser Met Arg Ile
                245                 250                 255

Val Glu Ala Glu His Pro Arg Thr Gly Thr Arg Tyr Arg Val Tyr Pro
            260                 265                 270

Met Met Asn Phe Ser Val Ala Val Asp Asp His Leu Leu Gly Val Thr
        275                 280                 285

His Val Leu Arg Gly Lys Asp His Leu Ala Asn Arg Glu Lys Gln Glu
    290                 295                 300

Tyr Leu Tyr Arg His Leu Gly Trp Glu Pro Pro Glu Phe Ile His Tyr
305                 310                 315                 320

Gly Arg Leu Lys Met Asp Asp Val Ala Leu Ser Thr Ser Gly Ala Arg
                325                 330                 335

Glu Gly Ile Leu Arg Gly Glu Tyr Ser Gly Trp Asp Asp Pro Arg Leu
            340                 345                 350

Gly Thr Leu Arg Ala Ile Ala Arg Arg Gly Ile Arg Pro Glu Ala Ile
        355                 360                 365

Arg Lys Leu Met Val Glu Ile Gly Val Lys Ile Ala Asp Ser Thr Met
    370                 375                 380

Ser Trp Lys Lys Ile Tyr Gly Leu Asn Arg Ser Ile Leu Glu Glu Glu
385                 390                 395                 400

Ala Arg Arg Tyr Phe Phe Ala Ala Asp Pro Val Lys Leu Glu Val Val
                405                 410                 415

Gly Leu Pro Gly Pro Val Arg Val Glu Arg Pro Leu His Pro Asp His
            420                 425                 430

Pro Glu Ile Gly Asn Arg Val Leu Glu Leu Arg Gly Glu Val Tyr Leu
        435                 440                 445

Pro Gly Asp Asp Leu Gly Glu Gly Pro Leu Arg Leu Ile Asp Ala Val
    450                 455                 460

Asn Val Ile Tyr Ser Gly Gly Glu Leu Arg Tyr His Ser Glu Gly Ile
465                 470                 475                 480

Glu Glu Ala Arg Glu Leu Gly Ala Ser Met Ile His Trp Val Pro Ala
                485                 490                 495

Glu Ser Ala Leu Glu Ala Glu Val Ile Met Pro Asp Ala Ser Arg Val
            500                 505                 510

Arg Gly Val Ile Glu Ala Asp Ala Ser Glu Leu Glu Val Asp Asp Val
        515                 520                 525
```

-continued

```
Val Gln Leu Glu Arg Phe Gly Phe Ala Arg Leu Asp Ser Ala Gly Pro
    530                 535                 540

Gly Met Val Phe Tyr Tyr Ala His Lys
545                 550
```

<210> SEQ ID NO 76
<211> LENGTH: 1713
<212> TYPE: DNA
<213> ORGANISM: Pyrococcus horikoshii

<400> SEQUENCE: 76

```
atggatgtgg aaaagatagc tctcaaacat gcccttatta atgcaattga gcatggaggt     60

aaggctaatc ttaaggccgt catcggtaaa gtgctcggcg agaaccctga gcttaggccc    120

agggccaagg agataattcc cataattaat aaggtagtgg aagaggtcaa ctcactagca    180

agggatgagc agctggaaaa gcttaaggat atatatccag agtactttga aaagaaggaa    240

gagaagaagg aaaagaaggg actacctctt cttcctaaag cagagaaagg caaggtcgtt    300

actcgctttg ctccaaatcc agatggtgct tttcacctgg gtaatgcaag ggccgcaata    360

cttagttatg aatacgccaa gatgtacggt gggaagttta tactccgctt tgatgatacc    420

gatccaaaag tcaagaggcc tgaacccata ttctacaaga tgataattga agatctagag    480

tggcttggaa taaagccaga tgaaatagtg tacgctagtg atagactcga aatttactac    540

aagtacgctg aggaactaat aaaaatgggt aaagcatatg tctgcacttg tcctccagag    600

aagttcagag agcttagaga taagggaatt ccatgtccgc atagagatga gcctgtggaa    660

gttcagctcg agcgctggaa gaagatgtta aacggcgaat ataaagaagg agaagctgtt    720

gtaaggataa agactgactt aaatcaccca aatcctgcgg ttagggattg gcccgcactt    780

agaataattg ataacccaaa ccatccgaga accggaaata agtacagggt atggcctctc    840

tacaattttg cctcagcgat tgatgatcac gagcttggag ttacccatat cttccgtgga    900

caggagcacg ccgagaacga gactagacag aggtatatct acgagtactt tggttgggag    960

tatcccgtca cgatccatca cgggaggctt agcatagagg gagttgtttt aagcaaatcc   1020

aagacaagga aggaatagaa agaaggtaag tatctcggtt gggatgatcc taggcttgga   1080

acgataagag ctttgaggag gaggggaatt cttcctgaag ccataaaaga attgatcata   1140

gaagttggat tgaagaaaag tgacgcgacg atcagttggg agaatctggc agcgataaac   1200

agaaaacttg ttgatccaat tgccaataga tatttctttg ttgcagatcc aattccgatg   1260

gaagtcgaag gggctcctga atttatagca gagataccgc ttcatcctga ccatcctgaa   1320

aggggcgtta gaaggcttaa gttcactcca gaaagacctg tttacgtttc gaaagacgat   1380

ttgaatctct taaaaccagg caattttgtg aggttaaagg atctcttcaa tgttgaaata   1440

cttgaagttg gagacaaaat aagagctagg ttctacagct ttgaatatga aattgcaaag   1500

aagaacaggt ggaagatggt tcactgggtt accgaaggta gaccctgtga ggttataatt   1560

cctgaaggag acgagcttgt agtgaggaag ggattgctcg agaaggatgc caaagttcaa   1620

gttaacgaaa tagtccagtt tgaacgtttc ggttttgtaa ggatagacag aattgagggg   1680

gataaagtta tcgcaatata tgctcacaag taa                                1713
```

<210> SEQ ID NO 77
<211> LENGTH: 570
<212> TYPE: PRT
<213> ORGANISM: Pyrococcus horikoshii -continued

<400> SEQUENCE: 77

```
Met Asp Val Glu Lys Ile Ala Leu Lys His Ala Leu Ile Asn Ala Ile
1               5                   10                  15

Glu His Gly Gly Lys Ala Asn Leu Lys Ala Val Ile Gly Lys Val Leu
            20                  25                  30

Gly Glu Asn Pro Glu Leu Arg Pro Arg Ala Lys Glu Ile Ile Pro Ile
        35                  40                  45

Ile Asn Lys Val Val Glu Glu Val Asn Ser Leu Ala Arg Asp Glu Gln
    50                  55                  60

Leu Glu Lys Leu Lys Asp Ile Tyr Pro Glu Tyr Phe Glu Lys Lys Glu
65                  70                  75                  80

Glu Lys Lys Glu Lys Lys Gly Leu Pro Leu Leu Pro Lys Ala Glu Lys
                85                  90                  95

Gly Lys Val Val Thr Arg Phe Ala Pro Asn Pro Asp Gly Ala Phe His
            100                 105                 110

Leu Gly Asn Ala Arg Ala Ala Ile Leu Ser Tyr Glu Tyr Ala Lys Met
        115                 120                 125

Tyr Gly Gly Lys Phe Ile Leu Arg Phe Asp Asp Thr Asp Pro Lys Val
    130                 135                 140

Lys Arg Pro Glu Pro Ile Phe Tyr Lys Met Ile Ile Glu Asp Leu Glu
145                 150                 155                 160

Trp Leu Gly Ile Lys Pro Asp Glu Ile Val Tyr Ala Ser Asp Arg Leu
                165                 170                 175

Glu Ile Tyr Tyr Lys Tyr Ala Glu Glu Leu Ile Lys Met Gly Lys Ala
            180                 185                 190

Tyr Val Cys Thr Cys Pro Pro Glu Lys Phe Arg Glu Leu Arg Asp Lys
        195                 200                 205

Gly Ile Pro Cys Pro His Arg Asp Glu Pro Val Glu Val Gln Leu Glu
    210                 215                 220

Arg Trp Lys Lys Met Leu Asn Gly Glu Tyr Lys Glu Gly Glu Ala Val
225                 230                 235                 240

Val Arg Ile Lys Thr Asp Leu Asn His Pro Asn Pro Ala Val Arg Asp
                245                 250                 255

Trp Pro Ala Leu Arg Ile Ile Asp Asn Pro Asn His Pro Arg Thr Gly
            260                 265                 270

Asn Lys Tyr Arg Val Trp Pro Leu Tyr Asn Phe Ala Ser Ala Ile Asp
        275                 280                 285

Asp His Glu Leu Gly Val Thr His Ile Phe Arg Gly Gln Glu His Ala
    290                 295                 300

Glu Asn Glu Thr Arg Gln Arg Tyr Ile Tyr Glu Tyr Phe Gly Trp Glu
305                 310                 315                 320

Tyr Pro Val Thr Ile His His Gly Arg Leu Ser Ile Glu Gly Val Val
                325                 330                 335

Leu Ser Lys Ser Lys Thr Arg Lys Gly Ile Glu Glu Gly Lys Tyr Leu
            340                 345                 350

Gly Trp Asp Asp Pro Arg Leu Gly Thr Ile Arg Ala Leu Arg Arg Arg
        355                 360                 365

Gly Ile Leu Pro Glu Ala Ile Lys Glu Leu Ile Ile Glu Val Gly Leu
    370                 375                 380

Lys Lys Ser Asp Ala Thr Ile Ser Trp Glu Asn Leu Ala Ala Ile Asn
385                 390                 395                 400

Arg Lys Leu Val Asp Pro Ile Ala Asn Arg Tyr Phe Phe Val Ala Asp
                405                 410                 415
```

-continued

```
Pro Ile Pro Met Glu Val Glu Gly Ala Pro Glu Phe Ile Ala Glu Ile
            420                 425                 430

Pro Leu His Pro Asp His Pro Glu Arg Gly Val Arg Arg Leu Lys Phe
        435                 440                 445

Thr Pro Glu Arg Pro Val Tyr Val Ser Lys Asp Asp Leu Asn Leu Leu
    450                 455                 460

Lys Pro Gly Asn Phe Val Arg Leu Lys Asp Leu Phe Asn Val Glu Ile
465                 470                 475                 480

Leu Glu Val Gly Asp Lys Ile Arg Ala Arg Phe Tyr Ser Phe Glu Tyr
                485                 490                 495

Glu Ile Ala Lys Lys Asn Arg Trp Lys Met Val His Trp Val Thr Glu
            500                 505                 510

Gly Arg Pro Cys Glu Val Ile Ile Pro Glu Gly Asp Glu Leu Val Val
        515                 520                 525

Arg Lys Gly Leu Leu Glu Lys Asp Ala Lys Val Gln Val Asn Glu Ile
    530                 535                 540

Val Gln Phe Glu Arg Phe Gly Phe Val Arg Ile Asp Arg Ile Glu Gly
545                 550                 555                 560

Asp Lys Val Ile Ala Ile Tyr Ala His Lys
                565                 570
```

<210> SEQ ID NO 78
<211> LENGTH: 1728
<212> TYPE: DNA
<213> ORGANISM: Sulfolobus solfataricus

<400> SEQUENCE: 78

```
ttgatggaat taaatgaatt acgagaaact atttataaat atgctcttca aaatgcggta     60

aagcataatg ggaaagccga aacgggtcca gtgatgagta agattatagc ggagaggccg    120

gaattaagat caaatgctag agaaattgta aagattatca aggagatcat agaacaagtt    180

aactcattaa ctttagagca gcagttaact gaaattaaag caaagtatcc agagttatta    240

gaagagaaga agcatgaaga aaaaagaaaa gtgttgccac ctcttcctaa tgttaaagga    300

caagtagtaa ctagatttgc ccctaatccg gatggtcctc ttcatttagg taacgcaagg    360

tctgcgattc tatcttacga atacgctaaa atgtataacg gtaagttcat actgaggttt    420

gatgatacag atcctaaggt taaaaggcca attctagatg catatgattg gattaaggag    480

gatctaaaat ggctgggaat taaatgggaa caagaacttt acgcttcgga aaggctcgag    540

ttatactata agtacgctcg gtatttgata gaaaaaggat atgcgtatgt tgatacatgt    600

gatagtagta ttttcaggaa gtttagggat agtagaggta aaatgaaaga gccagaatgt    660

ttacatagga gctcttcacc agagagtaat ctggagctgt ttgaaaaaat gctaggagga    720

aagtttaaag aaggagaagc tgtggttagg ttaaagaccg atctatcgga tccagatcca    780

tctcaaatag attgggtaat gcttagaata attgatactg ctaaaaatcc tcatccacga    840

gtagggagca agtattgggt atggcctacc tataactttg cttctataat agatgatcat    900

gaacttggaa ttactcatgt actgagagct aaggagcata tgtcaaatac agaaaagcag    960

agatacattt ctgagtacat gggatgggaa tttccagagg tcttacagtt tggaagacta   1020

agacttgaag gttttatgat gagtaagtcg aaaataagag gaatgttaga gaagggtacc   1080

aatagggatg atcctagatt gccaacttta gctggactca gaagaagagg aatcttacca   1140

gatacaatta aagacgtaat aattgatgtc ggagtaaagg taactgatgc tactataagt   1200
```

-continued

```
tttgagaaca ttgccgcaat taataggaaa aaactagatc cggtagctaa aagaataatg   1260

tttgtaaaag atgcagaaga atttagcgtc gagctacctg aatcactaaa tgctaaaata   1320

cctttaattc cctctaaaca agaaatgaat agaactatta ttgtcaatcc aggagataaa   1380

attttgatag aatctaacga tgcagaagat aatagtatac taaggttaat ggaattatgc   1440

aatgttaaag ttgataagca taatcgtaag ctcatatttc acagcaaaac gttagacgag   1500

gctaagaaag tcaatgcaaa gatagttcaa tgggtaaaat caaatgaaaa agtaccagta   1560

atggtagaga aagcggaaag agatgagata aaaatgataa atggttatgc tgaaaaaata   1620

gcagcagatt tggagataga cgaaattgta caattttacc gatttggatt tgtaagagta   1680

gataggaaag atgagaatat gctacgtgtt gtattctcac acgactga                1728
```

<210> SEQ ID NO 79
<211> LENGTH: 575
<212> TYPE: PRT
<213> ORGANISM: Sulfolobus solfataricus

<400> SEQUENCE: 79

```
Leu Met Glu Leu Asn Glu Leu Arg Glu Thr Ile Tyr Lys Tyr Ala Leu
1               5                   10                  15

Gln Asn Ala Val Lys His Asn Gly Lys Ala Glu Thr Gly Pro Val Met
            20                  25                  30

Ser Lys Ile Ile Ala Glu Arg Pro Glu Leu Arg Ser Asn Ala Arg Glu
        35                  40                  45

Ile Val Lys Ile Ile Lys Glu Ile Ile Glu Gln Val Asn Ser Leu Thr
    50                  55                  60

Leu Glu Gln Gln Leu Thr Glu Ile Lys Ala Lys Tyr Pro Glu Leu Leu
65                  70                  75                  80

Glu Glu Lys Lys His Glu Glu Lys Arg Lys Val Leu Pro Pro Leu Pro
                85                  90                  95

Asn Val Lys Gly Gln Val Val Thr Arg Phe Ala Pro Asn Pro Asp Gly
            100                 105                 110

Pro Leu His Leu Gly Asn Ala Arg Ser Ala Ile Leu Ser Tyr Glu Tyr
        115                 120                 125

Ala Lys Met Tyr Asn Gly Lys Phe Ile Leu Arg Phe Asp Asp Thr Asp
    130                 135                 140

Pro Lys Val Lys Arg Pro Ile Leu Asp Ala Tyr Asp Trp Ile Lys Glu
145                 150                 155                 160

Asp Leu Lys Trp Leu Gly Ile Lys Trp Glu Gln Glu Leu Tyr Ala Ser
                165                 170                 175

Glu Arg Leu Glu Leu Tyr Tyr Lys Tyr Ala Arg Tyr Leu Ile Glu Lys
            180                 185                 190

Gly Tyr Ala Tyr Val Asp Thr Cys Asp Ser Ser Ile Phe Arg Lys Phe
        195                 200                 205

Arg Asp Ser Arg Gly Lys Met Lys Glu Pro Glu Cys Leu His Arg Ser
    210                 215                 220

Ser Ser Pro Glu Ser Asn Leu Glu Leu Phe Glu Lys Met Leu Gly Gly
225                 230                 235                 240

Lys Phe Lys Glu Gly Glu Ala Val Val Arg Leu Lys Thr Asp Leu Ser
                245                 250                 255

Asp Pro Asp Pro Ser Gln Ile Asp Trp Val Met Leu Arg Ile Ile Asp
            260                 265                 270

Thr Ala Lys Asn Pro His Pro Arg Val Gly Ser Lys Tyr Trp Val Trp
        275                 280                 285
```

-continued

```
Pro Thr Tyr Asn Phe Ala Ser Ile Ile Asp Asp His Glu Leu Gly Ile
    290                 295                 300

Thr His Val Leu Arg Ala Lys Glu His Met Ser Asn Thr Glu Lys Gln
305                 310                 315                 320

Arg Tyr Ile Ser Glu Tyr Met Gly Trp Glu Phe Pro Glu Val Leu Gln
                325                 330                 335

Phe Gly Arg Leu Arg Leu Glu Gly Phe Met Met Ser Lys Ser Lys Ile
            340                 345                 350

Arg Gly Met Leu Glu Lys Gly Thr Asn Arg Asp Asp Pro Arg Leu Pro
        355                 360                 365

Thr Leu Ala Gly Leu Arg Arg Arg Gly Ile Leu Pro Asp Thr Ile Lys
    370                 375                 380

Asp Val Ile Ile Asp Val Gly Val Lys Val Thr Asp Ala Thr Ile Ser
385                 390                 395                 400

Phe Glu Asn Ile Ala Ala Ile Asn Arg Lys Lys Leu Asp Pro Val Ala
                405                 410                 415

Lys Arg Ile Met Phe Val Lys Asp Ala Glu Glu Phe Ser Val Glu Leu
            420                 425                 430

Pro Glu Ser Leu Asn Ala Lys Ile Pro Leu Ile Pro Ser Lys Gln Glu
        435                 440                 445

Met Asn Arg Thr Ile Ile Val Asn Pro Gly Asp Lys Ile Leu Ile Glu
    450                 455                 460

Ser Asn Asp Ala Glu Asp Asn Ser Ile Leu Arg Leu Met Glu Leu Cys
465                 470                 475                 480

Asn Val Lys Val Asp Lys His Asn Arg Lys Leu Ile Phe His Ser Lys
                485                 490                 495

Thr Leu Asp Glu Ala Lys Lys Val Asn Ala Lys Ile Val Gln Trp Val
            500                 505                 510

Lys Ser Asn Glu Lys Val Pro Val Met Val Glu Lys Ala Glu Arg Asp
        515                 520                 525

Glu Ile Lys Met Ile Asn Gly Tyr Ala Glu Lys Ile Ala Ala Asp Leu
    530                 535                 540

Glu Ile Asp Glu Ile Val Gln Phe Tyr Arg Phe Gly Phe Val Arg Val
545                 550                 555                 560

Asp Arg Lys Asp Glu Asn Met Leu Arg Val Val Phe Ser His Asp
                565                 570                 575
```

<210> SEQ ID NO 80
<211> LENGTH: 4813
<212> TYPE: DNA
<213> ORGANISM: artificial
<220> FEATURE:
<223> OTHER INFORMATION: pACKO-A184TAG
<220> FEATURE:
<221> NAME/KEY: misc_feature
<222> LOCATION: (3749)..(3749)
<223> OTHER INFORMATION: n is a, c, g, or t
<220> FEATURE:
<221> NAME/KEY: misc_feature
<222> LOCATION: (3769)..(3769)
<223> OTHER INFORMATION: n is a, c, g, or t

<400> SEQUENCE: 80

```
gaactccgga tgagcattca tcaggcgggc aagaatgtga ataaaggccg gataaaactt      60

gtgcttattt ttctttacgg tctttaaaaa ggccgtaata tccagctgaa cggtctggtt     120

ataggtacat tgagcaactg actgaaatgc ctcaaaatgt tctttacgat gccattggga     180
```

-continued

```
tatatcaacg gtggtatatc cagtgatttt tttctccatt ttagcttcct tagctcctga    240
aaatctcgat aactcaaaaa atacgcccgg tagtgatctt atttcattat ggtgaaagtt    300
ggaacctctt acgtgccgat caacgtctca ttttcgccaa aagttggccc agggcttccc    360
ggtatcaaca gggacaccag gatttattta ttctgcgaag tgatcttccg tcacaggtat    420
ttattcggcg caaagtgcgt cgggtgatgc tgccaactta ctgatttagt gtatgatggt    480
gtttttgagg tgctccagtg gcttctgttt ctatcagctg tccctcctgt tcagctactg    540
acggggtggt gcgtaacggc aaaagcaccg ccggacatca gcgctagcgg agtgtatact    600
ggcttactat gttggcactg atgagggtgt cagtgaagtg cttcatgtgg caggagaaaa    660
aaggctgcac cggtgcgtca gcagaatatg tgatacagga tatattccgc ttcctcgctc    720
actgactcgc tacgctcggt cgttcgactg cggcgagcgg aaatggctta cgaacggggc    780
ggagatttcc tggaagatgc caggaagata cttaacaggg aagtgagagg gccgcggcaa    840
agccgttttt ccataggctc cgcccccctg acaagcatca cgaaatctga cgctcaaatc    900
agtggtggcg aaacccgaca ggactataaa gataccaggc gtttccccct ggcggctccc    960
tcgtgcgctc tcctgttcct gcctttcggt ttaccggtgt cattccgctg ttatggccgc   1020
gtttgtctca ttccacgcct gacactcagt tccgggtagg cagttcgctc caagctggac   1080
tgtatgcacg aaccccccgt tcagtccgac cgctgcgcct tatccggtaa ctatcgtctt   1140
gagtccaacc cggaaagaca tgcaaaagca ccactggcag cagccactgg taattgattt   1200
agaggagtta gtcttgaagt catgcgccgg ttaaggctaa actgaaagga caagttttgg   1260
tgactgcgct cctccaagcc agttacctcg gttcaaagag ttggtagctc agagaacctt   1320
cgaaaaaccg ccctgcaagg cggttttttc gttttcagag caagagatta cgcgcagacc   1380
aaaacgatct caagaagatc atcttattaa tcagataaaa tatttctaga tttcagtgca   1440
atttatctct tcaaatgtag cacctgaagt cagccccata cgatataagt tgtaattctc   1500
atgtttgaca gcttatcatc gataagcttt aatgcggtag tttatcacag ttaaattgct   1560
aacgcagtca ggcaccgtgt atgaaatcta acaatgcgct catcgtcatc ctcggcaccg   1620
tcaccctgga tgctgtaggc ataggcttgg ttatgccggt actgccgggc ctcttgcggg   1680
atatcggttt cttagacgtc aggtggcact tttcggggaa atgtgcgcgg aacccctatt   1740
tgtttatttt tctaaataca ttcaaatatg tatccgctca tgagacaata accctgataa   1800
atgcttcaat aatattgaaa aaggaagagt atgagtattc aacatttccg tgtcgccctt   1860
attccctttt ttgcggcatt ttgccttcct gtttttgctc acccagaaac gctggtgaaa   1920
gtaaaagatg ctgaagatca gttgggtgca cgagtgggtt acatcgaact ggatctcaac   1980
agcggtaaga tccttgagag ttttcgcccc gaagaacgtt ttccaatgat gagcactttt   2040
aaagttctgc tatgtggcgc ggtattatcc cgtgttgacg ccgggcaaga gcaactcggt   2100
cgccgcatac actattctca gaatgacttg gttgagtact caccagtcac agaaaagcat   2160
cttacggatg gcatgacagt aagagaatta tgcagtgctg ccataaccat gagtgataac   2220
actgcggcca acttacttct gacaacgatc ggaggaccga aggagctaac cgcttttttg   2280
cacaacatgg gggatcatgt aactcgcctt gatcgttggg aaccggagct gaatgaagcc   2340
ataccaaacg acgagcgtga caccacgatg ccttaggcaa tggcaacaac gttgcgcaaa   2400
ctattaactg gcgaactact tactctagct tcccggcaac aattaataga ctggatggag   2460
gcggataaag ttgcaggacc acttctgcgc tcggcccttc cggctggctg gtttattgct   2520
gataaatctg gagccggtga gcgtgggtct cgcggtatca ttgcagcact ggggccagat   2580
```

-continued

```
ggtaagccct cccgtatcgt agttatctac acgacgggga gtcaggcaac tatggatgaa   2640
cgaaatagac agatcgctga gataggtgcc tcactgatta agcattggca ccaccaccac   2700
caccactaac ccgggaccaa gtttactcat atatacttta gattgattta aaacttcatt   2760
tttaatttaa aaggatctag gtgaagatcc tttttgataa tctcatgacc aaaatccctt   2820
aacggcatgc accattcctt gcggcggcgg tgctcaacgg cctcaaccta ctactgggct   2880
gcttcctaat gcaggagtcg cataagggag agcgtctggc gaaaggggga tgtgctgcaa   2940
ggcgattaag ttgggtaacg ccagggtttt cccagtcacg acgttgtaaa acgacggcca   3000
gtgccaagct taaaaaaaat ccttagcttt cgctaaggat ctgcagttat aatctctttc   3060
taattggctc taaaatcttt ataagttctt cagctacagc atttttaaa tccattggat   3120
gcaattcctt atttttaaat aaactctcta actcctcata gctattaact gtcaaatctc   3180
caccaaattt ttctggcctt tttatggtta aaggatattc aaggaagtat ttagctatct   3240
ccattattgg atttccttca acaactccag ctgggcagta tgctttcttt atcttagccc   3300
taatctcttc tggagagtca tcaacagcta taaaattccc ttttgaagaa ctcatctttc   3360
cttctccatc caaacccgtt aagacagggt tgtgaataca aacaaccttt tttggtaaaa   3420
gctcccttgc taacatgtgt atttttctct gctccatccc tccaactgca acatcaacgc   3480
ctaaataatg aatatcatta acctgcatta ttggatagat aacttcagca acctttggat   3540
tttcatcctc tcttgctata agttccatac tccttcttgc tctttttaag gtagttttta   3600
aagccaatct atagacattc agtgtataat ccttatcaag ctggaattca gcgttacaag   3660
tattacacaa agttttttat gttgagaata tttttttgat ggggcgccac ttatttttga   3720
tcgttcgctc aaagaagcgg cgccagggnt gtttttcttt tcaccagtna gacgggcaac   3780
agaacgccat gagcggcctc atttcttatt ctgagttaca acagtccgca ccgctgtccg   3840
gtagctcctt ccggtgggcg cggggcatga ctatcgtcgc cgcacttatg actgtcttct   3900
ttatcatgca actcgtagga caggtgccgg cagcgcccaa cagtccccg gccacggggc   3960
ctgccaccat acccacgccg aaacaagcgc cctgcaccat tatgttccgg atctgcatcg   4020
caggatgctg ctggctaccc tgtggaacac ctacatctgt attaacgaag cgctaaccgt   4080
ttttatcagg ctctgggagg cagaataaat gatcatatcg tcaattatta cctccacggg   4140
gagagcctga gcaaactggc ctcaggcatt tgagaagcac acggtcacac tgcttccggt   4200
agtcaataaa ccggtaaacc agcaatagac ataagcggct atttaacgac cctgccctga   4260
accgacgacc gggtcgaatt tgctttcgaa tttctgccat tcatccgctt attatcactt   4320
attcaggcgt agcaccaggc gtttaagggc accaataact gccttaaaaa aattacgccc   4380
cgccctgcca ctcatcgcag tactgttgta attcattaag cattctgccg acatggaagc   4440
catcacagac ggcatgatga acctgaatcg ccagcggcat cagcaccttg tcgccttgcg   4500
tataatattt gcccatggtg aaaacggggg cgaagaagtt gtccatattg gccacgttta   4560
aatcaaaact ggtgaaactc acccagggat tggctgagac gaaaaacata ttctcaataa   4620
accctttagg gaaataggcc aggttttcac cgtaacacgc cacatcttgc gaatatatgt   4680
gtagaaactg ccggaaatcg tcgtggtatt cactccagag cgatgaaaac gtttcagttt   4740
gctcatggaa aacggtgtaa caagggtgaa cactatccca tatcaccagc tcaccgtctt   4800
tcattgccat acg                                                       4813
```

<210> SEQ ID NO 81

-continued

<211> LENGTH: 4338
<212> TYPE: DNA
<213> ORGANISM: artificial
<220> FEATURE:
<223> OTHER INFORMATION: pACKO-Bla
<220> FEATURE:
<221> NAME/KEY: misc_feature
<222> LOCATION: (3274)..(3274)
<223> OTHER INFORMATION: n is a, c, g, or t
<220> FEATURE:
<221> NAME/KEY: misc_feature
<222> LOCATION: (3294)..(3294)
<223> OTHER INFORMATION: n is a, c, g, or t

<400> SEQUENCE: 81
gaactccgga tgagcattca tcaggcgggc aagaatgtga ataaaggccg gataaaactt 60
gtgcttattt ttctttacgg tctttaaaaa ggccgtaata tccagctgaa cggtctggtt 120
ataggtacat tgagcaactg actgaaatgc ctcaaaatgt tctttacgat gccattggga 180
tatatcaacg gtggtatatc cagtgatttt tttctccatt ttagcttcct tagctcctga 240
aaatctcgat aactcaaaaa atacgcccgg tagtgatctt atttcattat ggtgaaagtt 300
ggaacctctt acgtgccgat caacgtctca ttttcgccaa aagttggccc agggcttccc 360
ggtatcaaca gggacaccag gatttattta ttctgcgaag tgatcttccg tcacaggtat 420
ttattcggcg caaagtgcgt cgggtgatgc tgccaactta ctgatttagt gtatgatggt 480
gtttttgagg tgctccagtg gcttctgttt ctatcagctg tccctcctgt tcagctactg 540
acggggtggt gcgtaacggc aaaagcaccg ccggacatca gcgctagcgg agtgtatact 600
ggcttactat gttggcactg atgagggtgt cagtgaagtg cttcatgtgg caggagaaaa 660
aaggctgcac cggtgcgtca gcagaatatg tgatacagga tatattccgc ttcctcgctc 720
actgactcgc tacgctcggt cgttcgactg cggcgagcgg aaatggctta cgaacggggc 780
ggagatttcc tggaagatgc caggaagata cttaacaggg aagtgagagg gccgcggcaa 840
agccgttttt ccataggctc cgcccccctg acaagcatca cgaaatctga cgctcaaatc 900
agtggtggcg aaacccgaca ggactataaa gataccaggc gtttccccct ggcggctccc 960
tcgtgcgctc tcctgttcct gcctttcggt ttaccggtgt cattccgctg ttatggccgc 1020
gtttgtctca ttccacgcct gacactcagt tccgggtagg cagttcgctc caagctggac 1080
tgtatgcacg aaccccccgt tcagtccgac cgctgcgcct tatccggtaa ctatcgtctt 1140
gagtccaacc cggaaagaca tgcaaaagca ccactggcag cagccactgg taattgattt 1200
agaggagtta gtcttgaagt catgcgccgg ttaaggctaa actgaaagga caagttttgg 1260
tgactgcgct cctccaagcc agttacctcg gttcaaagag ttggtagctc agagaacctt 1320
cgaaaaaccg ccctgcaagg cggttttttc gttttcagag caagagatta cgcgcagacc 1380
aaaacgatct caagaagatc atcttattaa tcagataaaa tatttctaga tttcagtgca 1440
atttatctct tcaaatgtag cacctgaagt cagccccata cgatataagt tgtaattctc 1500
atgtttgaca gcttatcatc gataagcttt aatgcggtag tttatcacag ttaaattgct 1560
aacgcagtca ggcaccgtgt atgaaatcta acaatgcgct catcgtcatc ctcggcaccg 1620
tcaccctgga tgctgtaggc ataggcttgg ttatgccggt actgccgggc ctcttgcggg 1680
atatcggttt cttagacgtc aggtggcact tttcggggaa atgtgcgcgg aacccctatt 1740
tgtttatttt tctaaataca ttcaaatatg tatccgctca tgagacaata accctgataa 1800
atgcttcaat aatattgaaa aaggaagagt atgagtattc aacatttccg tgtcgccctt 1860
attccctttt ttgcggcatt ttgccttcct gtttttgctc acccagaaac actagtgcag 1920

-continued

```
caatggcaac aacgttgcgc aaactattaa ctggcgaact acttactcta gcttcccggc   1980
aacaattaat agactggatg gaggcggata aagttgcagg accacttctg cgctcggccc   2040
ttccggctgg ctggtttatt gctgataaat ctggagccgg tgagcgtggg tctcgcggta   2100
tcattgcagc actggggcca gatggtaagc cctcccgtat cgtagttatc tacacgacgg   2160
ggagtcaggc aactatggat gaacgaaata gacagatcgc tgagataggt gcctcactga   2220
ttaagcattg gtaacccggg accaagttta ctcatatata ctttagattg atttaaaact   2280
tcatttttaa tttaaaagga tctaggtgaa gatccttttt gataatctca tgaccaaaat   2340
cccttaacgg catgcaccat tccttgcggc ggcggtgctc aacggcctca acctactact   2400
gggctgcttc ctaatgcagg agtcgcataa gggagagcgt ctggcgaaag gggatgtgc   2460
tgcaaggcga ttaagttggg taacgccagg gttttcccag tcacgacgtt gtaaaacgac   2520
ggccagtgcc aagcttaaaa aaaatcctta gctttcgcta aggatctgca gttataatct   2580
ctttctaatt ggctctaaaa tctttataag ttcttcagct acagcatttt ttaaatccat   2640
tggatgcaat tccttatttt taaataaact ctctaactcc tcatagctat taactgtcaa   2700
atctccacca aatttttctg gcctttttat ggttaaagga tattcaagga agtatttagc   2760
tatctccatt attggatttc cttcaacaac tccagctggg cagtatgctt tctttatctt   2820
agccctaatc tcttctggag agtcatcaac agctataaaa ttcccttttg aagaactcat   2880
ctttccttct ccatccaaac ccgttaagac agggttgtga atacaaacaa ccttttttgg   2940
taaaagctcc cttgctaaca tgtgtatttt tctctgctcc atccctccaa ctgcaacatc   3000
aacgcctaaa taatgaatat cattaacctg cattattgga tagataactt cagcaacctt   3060
tggattttca tcctctcttg ctataagttc catactcctt cttgctcttt ttaaggtagt   3120
ttttaaagcc aatctataga cattcagtgt ataatcctta tcaagctgga attcagcgtt   3180
acaagtatta cacaaagttt tttatgttga gaatattttt ttgatggggc gccacttatt   3240
tttgatcgtt cgctcaaaga agcggcgcca gggntgtttt tcttttcacc agtnagacgg   3300
gcaacagaac gccatgagcg gcctcatttc ttattctgag ttacaacagt ccgcaccgct   3360
gtccggtagc tccttccggt gggcgcgggg catgactatc gtcgccgcac ttatgactgt   3420
cttctttatc atgcaactcg taggacaggt gccggcagcg cccaacagtc ccccggccac   3480
ggggcctgcc accataccca cgccgaaaca agcgccctgc accattatgt tccggatctg   3540
catcgcagga tgctgctggc taccctgtgg aacacctaca tctgtattaa cgaagcgcta   3600
accgttttta tcaggctctg ggaggcagaa taaatgatca tatcgtcaat tattacctcc   3660
acggggagag cctgagcaaa ctggcctcag gcatttgaga agcacacggt cacactgctt   3720
ccggtagtca ataaaccggt aaaccagcaa tagacataag cggctattta acgaccctgc   3780
cctgaaccga cgaccgggtc gaatttgctt tcgaatttct gccattcatc cgcttattat   3840
cacttattca ggcgtagcac caggcgttta agggcaccaa taactgcctt aaaaaaatta   3900
cgccccgccc tgccactcat cgcagtactg ttgtaattca ttaagcattc tgccgacatg   3960
gaagccatca cagacggcat gatgaacctg aatcgccagc ggcatcagca ccttgtcgcc   4020
ttgcgtataa tatttgccca tggtgaaaac gggggcgaag aagttgtcca tattggccac   4080
gtttaaatca aaactggtga aactcaccca gggattggct gagacgaaaa acatattctc   4140
aataaaccct ttagggaaat aggccaggtt ttcaccgtaa cacgccacat cttgcgaata   4200
tatgtgtaga aactgccgga aatcgtcgtg gtattcactc cagagcgatg aaaacgtttc   4260
```

-continued agtttgctca tggaaaacgg tgtaacaagg gtgaacacta tcccatatca ccagctcacc 4320
gtctttcatt gccatacg 4338

<210> SEQ ID NO 82
<211> LENGTH: 2271
<212> TYPE: DNA
<213> ORGANISM: artificial
<220> FEATURE:
<223> OTHER INFORMATION: pKQ

<400> SEQUENCE: 82
atggatccga gctcgagatc tgcagctggt accatatggg aattcgaagc ttgggcccga 60
acaaaaactc atctcagaag aggatctgaa tagcgccgtc gaccatcatc atcatcatca 120
ttgagtttaa acggtctcca gcttggctgt tttggcggat gagagaagat tttcagcctg 180
atacagatta aatcagaacg cagaagcggt ctgataaaac agaatttgcc tggcggcagt 240
agcgcggtgg tcccacctga ccccatgccg aactcagaag tgaaacgccg tagcgccgat 300
ggtagtgtgg ggtctcccca tgcgagagta gggaactgcc aggcatcaaa taaaacgaaa 360
ggctcagtcg aaagactggg cctttcgttt tatctgttgt ttgtcggtga acgatatctg 420
cttttcttcg cgaattaatt ccgcttcgca acatgtgagc aaaaggccag caaaaggcca 480
ggaaccgtaa aaaggccgcg ttgctggcgt ttttccatag gctccgcccc cctgacgagc 540
atcacaaaaa tcgacgctca agtcagaggt ggcgaaaccc gacaggacta taaagatacc 600
aggcgtttcc ccctggaagc tccctcgtgc gctctcctgt tccgaccctg ccgcttaccg 660
gatacctgtc cgcctttctc ccttcgggaa gcgtggcgct ttctcatagc tcacgctgta 720
ggtatctcag ttcggtgtag gtcgttcgct ccaagctggg ctgtgtgcac gaaccccccg 780
ttcagcccga ccgctgcgcc ttatccggta actatcgtct tgagtccaac ccggtaagac 840
acgacttatc gccactggca gcagccactg gtaacaggat tagcagagcg aggtatgtag 900
gcggtgctac agagttcttg aagtggtggc ctaactacgg ctacactaga aggacagtat 960
ttggtatctg cgctctgctg aagccagtta ccttcggaaa aagagttggt agctcttgat 1020
ccggcaaaca aaccaccgct ggtagcggtg gtttttttgt ttgcaagcag cagattacgc 1080
gcagaaaaaa aggatctcaa gaagatcctt tgatcttttc tacggggtct gacgctcagt 1140
ggaacgaaaa ctcacgttaa gggattttgg tcatgagttg tgtctcaaaa tctctgatgt 1200
tacattgcac aagataaaaa tatatcatca tgaacaataa aactgtctgc ttacataaac 1260
agtaatacaa ggggtgttat gagccatatt caacgggaaa cgtcttgctc gaggccgcga 1320
ttaaattcca acatggatgc tgatttatat gggtataaat gggctcgcga taatgtcggg 1380
caatcaggtg cgacaatcta tcgattgtat gggaagcccg atgcgccaga gttgtttctg 1440
aaacatggca aaggtagcgt tgccaatgat gttacagatg agatggtcag actaaactgg 1500
ctgacggaat ttatgcctct tccgaccatc aagcatttta tccgtactcc tgatgatgca 1560
tggttactca ccactgcgat ccccgggaaa acagcattcc aggtattaga agaatatcct 1620
gattcaggtg aaaatattgt tgatgcgctg gcagtgttcc tgcgccggtt gcattcgatt 1680
cctgtttgta attgtccttt taacagcgat cgcgtatttc gtctcgctca ggcgcaatca 1740
cgaatgaata acggtttggt tgatgcgagt gattttgatg acgagcgtaa tggctggcct 1800
gttgaacaag tctggaaaga aatgcataag cttttgccat tctcaccgga ttcagtcgtc 1860
actcatggtg atttctcact tgataacctt atttttgacg aggggaaatt aataggttgt 1920
attgatgttg gacgagtcgg aatcgcagac cgataccagg atcttgccat cctatggaac 1980

-continued

```
tgcctcggtg agttttctcc ttcattacag aaacggcttt ttcaaaaata tggtattgat   2040

aatcctgata tgaataaatt gcagtttcat ttgatgctcg atgagttttt ctaatcagaa   2100

ttggttaatt ggttgtaaca ctggcagagc attacgctga cttgacggga cggcggcttt   2160

gttgaataaa tcgaactttt gctgagttga aggatcctcg ggagttgtca gcctgtcccg   2220

cttataagat catacgccgt tatacgttgt ttacgctttg aggaattaac c            2271


<210> SEQ ID NO 83
<211> LENGTH: 38
<212> TYPE: DNA
<213> ORGANISM: artificial
<220> FEATURE:
<223> OTHER INFORMATION: oligonucleotide primer

<400> SEQUENCE: 83

ggagagaaga ctacatgaaa gaagtcataa tgaaatac                             38


<210> SEQ ID NO 84
<211> LENGTH: 38
<212> TYPE: DNA
<213> ORGANISM: artificial
<220> FEATURE:
<223> OTHER INFORMATION: oligonucleotide primer

<400> SEQUENCE: 84

cgttagaaga ctgaattcgg attttggtca cgggtgcg                             38


<210> SEQ ID NO 85
<211> LENGTH: 36
<212> TYPE: DNA
<213> ORGANISM: artificial
<220> FEATURE:
<223> OTHER INFORMATION: oligonucleotide primer

<400> SEQUENCE: 85

gctatcacac catggcgatg ctcctagggg accatc                               36


<210> SEQ ID NO 86
<211> LENGTH: 40
<212> TYPE: DNA
<213> ORGANISM: artificial
<220> FEATURE:
<223> OTHER INFORMATION: oligonucleotide primer

<400> SEQUENCE: 86

gatcagtcag aattcttact tgtgtgtgta tatcaccctg                           40


<210> SEQ ID NO 87
<211> LENGTH: 33
<212> TYPE: DNA
<213> ORGANISM: artificial
<220> FEATURE:
<223> OTHER INFORMATION: oligonucleotide primer

<400> SEQUENCE: 87

ggagacgtct cacatggaag agaagatatt gcc                                  33


<210> SEQ ID NO 88
<211> LENGTH: 36
<212> TYPE: DNA
<213> ORGANISM: artificial
<220> FEATURE:
<223> OTHER INFORMATION: oligonucleotide primer
```

-continued

<400> SEQUENCE: 88
cgttacgtct cgaattttat ctatgtgcat agcaac 36

<210> SEQ ID NO 89
<211> LENGTH: 33
<212> TYPE: DNA
<213> ORGANISM: artificial
<220> FEATURE:
<223> OTHER INFORMATION: oligonucleotide primer

<400> SEQUENCE: 89
ggagacgtct cacatgacct taagtcctga aga 33

<210> SEQ ID NO 90
<211> LENGTH: 43
<212> TYPE: DNA
<213> ORGANISM: artificial
<220> FEATURE:
<223> OTHER INFORMATION: oligonucleotide primer

<400> SEQUENCE: 90
cgttacgtct cgaattttat ttatgagcaa agtacgccac gac 43

<210> SEQ ID NO 91
<211> LENGTH: 33
<212> TYPE: DNA
<213> ORGANISM: artificial
<220> FEATURE:
<223> OTHER INFORMATION: oligonucleotide primer

<400> SEQUENCE: 91
ggagacgtct ctcatggtgc cagtggagga cct 33

<210> SEQ ID NO 92
<211> LENGTH: 38
<212> TYPE: DNA
<213> ORGANISM: artificial
<220> FEATURE:
<223> OTHER INFORMATION: oligonucleotide primer

<400> SEQUENCE: 92
cgttacgtct ctaattttat ttgtgggcat agtagaag 38

<210> SEQ ID NO 93
<211> LENGTH: 33
<212> TYPE: DNA
<213> ORGANISM: artificial
<220> FEATURE:
<223> OTHER INFORMATION: oligonucleotide primer

<400> SEQUENCE: 93
ggaaaggtct ctcatggatg tggaaaagat agc 33

<210> SEQ ID NO 94
<211> LENGTH: 36
<212> TYPE: DNA
<213> ORGANISM: artificial
<220> FEATURE:
<223> OTHER INFORMATION: oligonucleotide primer

<400> SEQUENCE: 94
gagtaggtct ctaattttac ttgtgagcat atattg 36

<210> SEQ ID NO 95
<211> LENGTH: 36

-continued

<212> TYPE: DNA
<213> ORGANISM: artificial
<220> FEATURE:
<223> OTHER INFORMATION: oligonucleotide primer

<400> SEQUENCE: 95
gctactgcac catggaatta aatgaattac gagaac 36

<210> SEQ ID NO 96
<211> LENGTH: 38
<212> TYPE: DNA
<213> ORGANISM: artificial
<220> FEATURE:
<223> OTHER INFORMATION: oligonucleotide primer

<400> SEQUENCE: 96
gactcagtag aattcattag tcgtgtgaga atacaaca 38

<210> SEQ ID NO 97
<211> LENGTH: 48
<212> TYPE: DNA
<213> ORGANISM: artificial
<220> FEATURE:
<223> OTHER INFORMATION: oligonucleotide primer

<400> SEQUENCE: 97
cggaattcgc cccggtggtg tagcccggcc aagcatgcgg gcctctaa 48

<210> SEQ ID NO 98
<211> LENGTH: 67
<212> TYPE: DNA
<213> ORGANISM: artificial
<220> FEATURE:
<223> OTHER INFORMATION: oligonucleotide primer

<400> SEQUENCE: 98
aaactgcagt ggtgccccgg ccgggatttg aacccgggtc gcgggcttta gaggcccgca 60
tgcttgg 67

<210> SEQ ID NO 99
<211> LENGTH: 58
<212> TYPE: DNA
<213> ORGANISM: artificial
<220> FEATURE:
<223> OTHER INFORMATION: oligonucleotide primer

<400> SEQUENCE: 99
cggaattcag ccccgtggtg tagcggccaa gcatgcgggg ctctaaaccc cgcgaccg 58

<210> SEQ ID NO 100
<211> LENGTH: 55
<212> TYPE: DNA
<213> ORGANISM: artificial
<220> FEATURE:
<223> OTHER INFORMATION: oligonucleotide primer

<400> SEQUENCE: 100
aaactgcagt ggtagccccg cggggattcg aaccccggtc gcggggttta gagcc 55

<210> SEQ ID NO 101
<211> LENGTH: 58
<212> TYPE: DNA
<213> ORGANISM: artificial
<220> FEATURE:
<223> OTHER INFORMATION: oligonucleotide primer -continued

<400> SEQUENCE: 101
cggaattcag ccccgtggtg tagcggccaa gcacgcgggg ctctaaaccc cgcgaccg 58

<210> SEQ ID NO 102
<211> LENGTH: 55
<212> TYPE: DNA
<213> ORGANISM: artificial
<220> FEATURE:
<223> OTHER INFORMATION: oligonucleotide primer

<400> SEQUENCE: 102
aaactgcagt ggtagccccg cggggattcg aaccccggtc gcggggttta gagcc 55

<210> SEQ ID NO 103
<211> LENGTH: 48
<212> TYPE: DNA
<213> ORGANISM: artificial
<220> FEATURE:
<223> OTHER INFORMATION: oligonucleotide primer
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (36)..(36)
<223> OTHER INFORMATION: n is a, c, g, or t

<400> SEQUENCE: 103
cggaattcgc cccggtgntg tagcccggcc aagcangcgg gcctctaa 48

<210> SEQ ID NO 104
<211> LENGTH: 18
<212> TYPE: DNA
<213> ORGANISM: artificial
<220> FEATURE:
<223> OTHER INFORMATION: oligonucleotide primer

<400> SEQUENCE: 104
ggacagcggt gcggactg 18

<210> SEQ ID NO 105
<211> LENGTH: 18
<212> TYPE: DNA
<213> ORGANISM: artificial
<220> FEATURE:
<223> OTHER INFORMATION: oligonucleotide primer

<400> SEQUENCE: 105
gtgctcaacg gcctcaac 18

<210> SEQ ID NO 106
<211> LENGTH: 38
<212> TYPE: DNA
<213> ORGANISM: artificial
<220> FEATURE:
<223> OTHER INFORMATION: oligonucleotide primer

<400> SEQUENCE: 106
aggcttttaa ccatggcaaa aatcaaaact cgcttcgc 38

<210> SEQ ID NO 107
<211> LENGTH: 33
<212> TYPE: DNA
<213> ORGANISM: artificial
<220> FEATURE:
<223> OTHER INFORMATION: oligonucleotide primer -continued

```
<400> SEQUENCE: 107

acgtgagagg aattctgctg attttcgcgt tca                              33


<210> SEQ ID NO 108
<211> LENGTH: 48
<212> TYPE: DNA
<213> ORGANISM: artificial
<220> FEATURE:
<223> OTHER INFORMATION: oligonucleotide primer

<400> SEQUENCE: 108

cgttagaaga ctgaattggg gtgagtgtac accgcgacca gttcctcg              48


<210> SEQ ID NO 109
<211> LENGTH: 40
<212> TYPE: DNA
<213> ORGANISM: artificial
<220> FEATURE:
<223> OTHER INFORMATION: oligonucleotide primer

<400> SEQUENCE: 109

cgttacgtct cgaattctta tgagcaaagt acgccacgac                      40


<210> SEQ ID NO 110
<211> LENGTH: 38
<212> TYPE: DNA
<213> ORGANISM: artificial
<220> FEATURE:
<223> OTHER INFORMATION: oligonucleotide primer

<400> SEQUENCE: 110

cgttacgtct ctaatttttg tgggcatagt agaagacc                        38


<210> SEQ ID NO 111
<211> LENGTH: 39
<212> TYPE: DNA
<213> ORGANISM: artificial
<220> FEATURE:
<223> OTHER INFORMATION: oligonucleotide primer

<400> SEQUENCE: 111

gagtaggtct ctaattcttg tgagcatata ttgcgataa                       39
```

COMPOSITIONS OF ORTHOGONAL GLUTAMYL-TRNA AND AMINOACYL-TRNA SYNTHETASE PAIRS AND USES THEREOF

CROSS-REFERENCE TO RELATED APPLICATIONS

This application is a national phase entry in the United States under 35 U.S.C. § 371 from International Application Number PCT/US2004/021813, which has an international filing date of Jul. 7, 2004, and which designated the United States of America, which claims priority to and benefit of Provisional Patent Application U.S. Ser. No. 60/485,451, filed Jul. 7, 2003; and to Provisional Patent Application U.S. Ser. No. 60/513,109, filed Oct. 20, 2003, the disclosures of which are incorporated herein by reference in their entirety for all purposes.

This invention was made with U.S. Government support under Contract No. GM 62159 from the National Institutes of Health and Contract No. DE-FG03-00ER45812 from the Department of Energy. The U.S. Government has certain rights to the invention.

FIELD OF THE INVENTION

The invention is in the field of translation biochemistry. The invention relates to methods for producing and compositions of orthogonal glutamyl-tRNAs, orthogonal glutamyl aminoacyl-tRNA synthetases and pairs thereof. The invention also relates to methods of producing proteins in cells using such pairs and related compositions.

BACKGROUND OF THE INVENTION

The genetic code of every known organism, from bacteria to humans, encodes the same twenty common amino acids. Different combinations of the same twenty natural amino acids form proteins that carry out virtually all the complex processes of life, from photosynthesis to signal transduction and the immune response. In order to study and modify protein structure and function, scientists have attempted to manipulate both the genetic code and the amino acid sequence of proteins. However, it has been difficult to remove the constraints imposed by the genetic code that limit proteins to twenty genetically encoded standard building blocks (with the rare exception of selenocysteine (see, e.g., A. Bock et al., (1991), *Molecular Microbiology* 5:515-20) and pyrrolysine (see, e.g., G. Srinivasan, et al., (2002), *Science* 296:1459-62).

Some progress has been made to remove these constraints, although this progress has been limited, and the ability to rationally control protein structure and function is still in its infancy. For example, chemists have developed methods and strategies to synthesize and manipulate the structures of small molecules (see, e.g., E. J. Corey, & X.-M. Cheng, *The Logic of Chemical Synthesis* (Wiley-Interscience, New York, 1995)). Total synthesis (see, e.g., B. Merrifield, (1986), *Science* 232:341-7 (1986)), and semi-synthetic methodologies (see, e.g., D.Y. Jackson et al., (1994) *Science* 266:243-7; and, P. E. Dawson, & S. B. Kent, (2000), *Annual Review of Biochemistry* 69:923-60), have made it possible to synthesize peptides and small proteins, but these methodologies have limited utility with proteins over 10 kilo Daltons (kDa). Mutagenesis methods, though powerful, are restricted to a limited number of structural changes. In a number of cases, it has been possible to competitively incorporate close structural analogues of common amino acids throughout proteins. See, e.g., R. Furter, (1998), *Protein Science* 7:419-26; K. Kirshenbaum, et al., (2002), *Chem Bio Chem* 3:235-7; and, V. Doring et al., (2001), *Science* 292:501-4.

Early work demonstrated that the translational machinery of *E. coli* would accommodate amino acids similar in structure to the common twenty. See Hortin, G., and Boime, I. (1983) *Methods Enzymol.* 96:777-784. This work was further extended by relaxing the specificity of endogenous *E. coli* synthetases so that they activate unnatural amino acids as well as their cognate natural amino acid. Moreover, it was shown that mutations in editing domains could also be used to extend the substrate scope of the endogenous synthetase. See Doring, V., et al., (2001) *Science* 292:501-504. However, these strategies are limited to recoding the genetic code rather than expanding the genetic code and lead to varying degrees of substitution of one of the common twenty amino acids with an unnatural amino acid.

Later it was shown that unnatural amino acids could be site-specifically incorporated into proteins in vitro by the addition of chemically aminoacylated orthogonal amber suppressor tRNAs to an in vitro transcription/translation reaction. See, e.g., Noren, C. J., et al. (1989) *Science* 244:182-188; Bain, J. D., et al., (1989) *J. Am. Chem. Soc.* 111:8013-8014; Dougherty, D. A. (2000) *Curr. Opin. Chem. Biol.* 4, 645-652; Cornish, V. W., et al. (1995) *Angew. Chem. Int. Ed.* 34:621-633; J. A. Ellman, et al., (1992), *Science* 255:197-200; and, D. Mendel, et al., (1995), *Annual Review of Biophysics and Biomolecular Structure* 24:435-462. These studies show that the ribosome and translation factors are compatible with a large number of unnatural amino acids, even those with unusual structures. Unfortunately, the chemical aminoacylation of tRNAs is difficult, and the stoichiometric nature of this process severely limited the amount of protein that could be generated.

Unnatural amino acid tRNA complexes have been microinjected into cells. For example, unnatural amino acids were introduced into the nicotinic acetylcholine receptor in *Xenopus* oocytes (e.g., M. W. Nowak, et al. (1998), *In vivo incorporation of unnatural amino acids into ion channels in Xenopus oocyte expression system, Method Enzymol.* 293:504-529) by microinjection of a chemically misacylated *Tetrahymena thermophila* tRNA (e.g., M. E. Saks, et al. (1996), *An engineered Tetrahymena tRNAGln for in vivo incorporation of unnatural amino acids into proteins by nonsense suppression, J. Biol. Chem.* 271:23169-23175), and the relevant mRNA. See also D. A. Dougherty (2000), *Unnatural amino acids as probes of protein structure and function, Curr. Opin. Chem. Biol.* 4:645-652. Unfortunately, this methodology is limited to proteins in cells that can be microinjected, and because the relevant tRNA is chemically acylated in vitro, and cannot be re-acylated, the yields of protein are very low.

To overcome these limitations, new components, e.g., orthogonal tRNAs, orthogonal aminoacyl-tRNA synthetases and pairs thereof, were added to the protein biosynthetic machinery of the prokaryote *Escherichia coli* (*E. coli*) (see, e.g., L. Wang, et al., (2001), *Science* 292:498-500), which allowed genetic encoding of unnatural amino acids in vivo. A number of new amino acids with novel chemical, physical or biological properties, including photoaffinity labels and photoisomerizable amino acids, photocrosslinking amino acids (see, e.g., Chin, J. W., et al. (2002) *Proc. Natl. Acad. Sci. U.S.A.* 99:11020-11024; and, Chin, J. W., et al., (2002) *J. Am. Chem. Soc.* 124:9026-9027), keto amino acids (see, e.g., Wang, L., et al., (2003) *Proc. Natl. Acad. Sci. U.S.A.* 100:56-61), heavy atom containing amino acids, and glycosylated amino acids have been incorporated efficiently and with high fidelity into proteins in *E. coli* in response to, e.g., the amber codon (TAG), using this methodology.

Several other orthogonal pairs have been reported. Glutaminyl (see, e.g., Liu, D. R., and Schultz, P. G. (1999) *Proc. Natl. Acad. Sci. U.S.A.* 96:4780-4785), aspartyl (see, e.g., Pastrnak, M., et al., (2000) *Helv. Chim. Acta* 83:2277-2286), and tyrosyl (see, e.g., Ohno, S., et al., (1998) *J. Biochem.* (*Tokyo. Jpn.*) 124:1065-1068; and, Kowal, A. K., et al., (2001) *Proc. Natl. Acad. Sci. U.S.A.* 98:2268-2273) systems derived from *S. cerevisiae* tRNAs and synthetases have been described for the potential incorporation of unnatural amino acids in *E. coli*. In addition, a leucine system, which includes an archaeal derived tRNA and a synthetase derived from, e.g., *Methanobacterium thermoautotrophicum*, has also been described. See Anderson and Schultz, (2003), *Biochemistry,* 42(32):9598-608. Systems derived from the *E. coli* glutaminyl (see, e.g., Kowal, A. K., et al., (2001) *Proc. Natl. Acad. Sci. U.S.A.* 98:2268-2273) and tyrosyl (see, e.g., Edwards, H., and Schimmel, P. (1990) *Mol. Cell. Biol.* 10:1633-1641) synthetase have been described for use in *S. cerevisiae*. The *E. coli* tyrosyl system has been used for the incorporation of 3-iodo-L-tyrosine in vivo, in mammalian cells. See Sakamoto, K., et al., (2002) *Nucleic Acids Res.* 30:4692-4699.

Unnatural amino acids that have been incorporated into proteins, e.g., using variants of the tyrosyl-tRNA synthetase, are aryl derivatives, including p-azido- (see, e.g., Chin et al., (2002) *Addition of p-azido-L-phenylalamine to the genetic code of Escherichia coli, J. Am. Chem. Soc.,* 124:9026-9027), p-benzoyl- (see, e.g., Chin et al., (2002) *Addition of a photo-crosslinkiing amino acid to the genetic code of Escherchia coli, PNAS, USA,* 99:11020-11024), p-amino- (see, e.g., Santoro et al., (2002), *An efficient system for the evolution of aminoacyl-tRNA synthetase specificity, Nat. Biotechnology,* 20:1044-1048), p-isopropyl- (see, e.g., Santoro et al., (2002), *An efficient system for the evolution of aminoacyl-tRNA synthetase specificity, Nat. Biotechnology,* 20:1044-1048), m-acetyl- (see, e.g., Wang et al., (2003), *Addition of the keto functional group to the genetic code of Escherichia coli, PNAS, USA,* 100:56-61), and p-acetyl-phenylalanine (Wang et al., (2003), *Addition of the keto functional group to the genetic code of Escherichia coli, PNAS, USA,* 100:56-61); O-methyl- (see, e.g., Wang et al., (2001), *Expanding the genetic code of Escherichia coli, Science* 292:498-500) and O-allyl-tyrosine (see, e.g., Santoro et al., (2002), *An efficient system for the evolution of aminoacyl-tRNA synthetase specificity, Nat. Biotechnology,* 20:1044-1048; and Zhang et al., (2002) *The selective incorporation of alkenes into proteins in Escherichia coli, Angew Chem. Int. Ed. Engl.,* 41:2840-2842); 3-(2-naphthyl)alanine (see, e.g., Wang et al., (2002) *Adding L-3-(2-Naphthyl)alanine to the genetic code of E. coli, J. Am. Chem. Soc.,* 124:1836-1837); and a p-propargyloxy phenylalanine (see, e.g., Deiters et al., (2003) *Adding Amino Acids with Novel Reactivity to the Genetic Code of Saccharomyces Cerevisiae*, in press). To further expand the genetic code and increase the diversity of unnatural amino acid structures that can be incorporated into proteins in a cell, there is a need to develop improved and/or additional components of the biosynthetic machinery, e.g., orthogonal tRNAs, orthogonal aminoacyl-tRNA synthetases and/or unique codons. This invention fulfills these and other needs, as will be apparent upon review of the following disclosure.

SUMMARY OF THE INVENTION

The invention provides compositions and methods of producing orthogonal components for incorporating a selected amino acid into a growing polypeptide chain in response to a selector codon, e.g., a stop codon, a nonsense codon, a four or more base codon, etc., e.g., in vivo. For example, the invention provides orthogonal glutamyl-tRNAs (glutamyl O-tRNAs), orthogonal glutamyl aminoacyl-tRNA synthetases (glutamyl O-RSs) and pairs thereof. These pairs can be used to incorporate selected amino acids into growing polypeptide chains.

Typically, a glutamyl O-tRNA of the invention includes at least about, e.g., a 45%, a 50%, a 60%, a 75%, a 80%, or a 90% or more suppression efficiency in the presence of a cognate synthetase in response to a selector codon, as compared to the glutamyl O-tRNA corresponding to a polynucleotide sequence as set forth in SEQ ID NO.: 67 (AE(GC) tRNA). A composition that includes a glutamyl O-tRNA can optionally further include an orthogonal glutamyl aminoacyl-tRNA synthetase (glutamyl O-RS), where the glutamyl O-RS preferentially aminoacylates the glutamyl O-tRNA with a selected amino acid. In one embodiment, the suppression efficiency of the glutamyl O-RS and the glutamyl O-tRNA together is, e.g., 5 fold, 10 fold, 15 fold, 20 fold, 25 fold or more greater than the suppression efficiency of the glutamyl O-tRNA lacking the glutamyl O-RS.

A composition that includes a glutamyl O-tRNA can optionally include a cell (e.g., a non-eukaryotic cell, such as an *E. coli* cell and the like, or a eukaryotic cell), and/or a translation system.

A cell (e.g., a non-eukaryotic cell, or a eukaryotic cell) comprising a translation system is also provided by the invention, where the translation system includes an orthogonal glutamyl-tRNA (glutamyl O-tRNA); an orthogonal aminoacyl-glutamyl-tRNA synthetase (glutamyl O-RS); and, a first selected amino acid. Typically, the glutamyl O-tRNA comprises at least about, e.g., a 45%, a 50%, a 60%, a 75%, a 80%, or a 90% or more suppression efficiency in the presence of a cognate synthetase in response to a first selector codon as compared to a glutamyl O-tRNA comprising or encoded by a polynucleotide sequence as set forth in SEQ ID NO.: 67 (AE(GC) tRNA). The glutamyl O-tRNA recognizes the first selector codon, and the glutamyl O-RS preferentially aminoacylates the glutamyl O-tRNA with the first selected amino acid in response to the selector codon. In one embodiment, the glutamyl O-tRNA comprises or is encoded by a polynucleotide sequence as set forth in SEQ ID NO.: 67 (AE(GC)), or a complementary polynucleotide sequence thereof. In one aspect, the glutamyl O-tRNA comprises a G:C base pair at position 10:28. In one embodiment, the glutamyl O-RS comprises an amino acid sequence as set forth in any one of SEQ ID NO.: 69 (Af), 73 (Mm), 75 (Mt), or 77 (Ph), or a conservative variation thereof.

A cell of the invention can optionally further comprise an additional different O-tRNA/O-RS pair and a second selected amino acid, e.g., where this O-tRNA recognizes a second selector codon and this O-RS preferentially aminoacylates the O-tRNA with the second selected amino acid. Optionally, a cell of the invention includes a nucleic acid that comprises a polynucleotide that encodes a polypeptide of interest, where the polynucleotide comprises a selector codon that is recognized by the glutamyl O-tRNA.

In certain embodiments, a cell of the invention includes an *E. coli* cell that includes an orthogonal glutamyl tRNA (glutamyl O-tRNA), an orthogonal glutamyl aminoacyl-tRNA synthetase (glutamyl O-RS), a selected amino acid, and a nucleic acid that comprises a polynucleotide that encodes a polypeptide of interest, where the polynucleotide comprises the selector codon that is recognized by the glutamyl O-tRNA. Typically, the glutamyl O-tRNA comprises at least about, e.g., a 45%, a 50%, a 60%, a 75%, a 80%, or a 90% or more suppression efficiency in the presence of a cognate synthetase in response to a selector codon as compared to the glutamyl O-tRNA comprising or encoded by a polynucleotide sequence as set forth in SEQ ID NO.: 67 (AE(GC) tRNA), and the glutamyl O-RS preferentially aminoacylates the glutamyl O-tRNA with a selected amino acid in response to the selector codon.

In certain embodiments of the invention, a glutamyl O-tRNA of the invention comprises or is encoded by a polynucleotide sequence as set forth in SEQ ID NO.: 67, or a complementary polynucleotide sequence thereof. In one embodiment, the glutamyl O-tRNA comprises a G:C base pair at position 10:28. In certain embodiments of the invention, a glutamyl O-RS comprises an amino acid sequence comprising any one of SEQ ID NO.: 69, 73, 75 and/or 77, or a conservative variation thereof. In one embodiment, the glutamyl O-RS or a portion thereof is encoded by a polynucleotide sequence comprising any one of SEQ ID NO.: 68, 72, 74, or 76, or a complementary polynucleotide sequence thereof.

The glutamyl O-tRNA and/or the glutamyl O-RS of the invention can be derived from any of a variety of organisms (e.g., eukaryotic and/or non-eukaryotic organisms). For example, the glutamyl O-tRNA can be derived from one or more archaeal tRNAs and/or the glutamyl O-RS can be derived from, e.g., a non-eukaryotic organism (e.g., an *Archaeoglobus fulgidus* (Af), a *Methanosarcina mazei* (Mm), a *Methanobacterium thermoautotrophicum* (Mt), a *Pyrococcus horikoshii* (Ph), etc.).

Polynucleotides are also a feature of the invention. A polynucleotide of the invention includes an artificial (e.g., man-made, and not naturally occurring) polynucleotide comprising a nucleotide sequence as set forth in SEQ ID NO.: 67, and/or is complementary to or that encodes a polynucleotide sequence of the above. A polynucleotide of the invention also includes a nucleic acid that hybridizes to a polynucleotide described above, under highly stringent conditions over substantially the entire length of the nucleic acid. A polynucleotide of the invention also includes a polynucleotide that is, e.g., at least 75%, at least 80%, at least 90%, at least 95%, at least 98% or more identical to that of a naturally occurring glutamyl tRNA (but is other than a naturally occurring glutamyl tRNA) and comprises a G:C base pair at position 10:28. Artificial polynucleotides that are, e.g., at least 80%, at least 90%, at least 95%, at least 98% or more identical to any of the above and/or a polynucleotide comprising a conservative variation of any the above, are also included in polynucleotides of the invention.

Vectors comprising a polynucleotide of the invention are also a feature of the invention. For example, a vector of the invention can include a plasmid, a cosmid, a phage, a virus, an expression vector, and/or the like. A cell comprising a vector of the invention is also a feature of the invention.

Methods of producing components of a glutamyl O-tRNA/O-RS pair are also features of the invention. Components produced by these methods are also a feature of the invention. For example, methods of producing at least one glutamyl tRNA that are orthogonal to a cell (glutamyl O-tRNA) include aligning a plurality of glutamyl tRNA sequences (e.g., derived from a species other than the host cell, derived from an archaeal species, etc.); and, determining a consensus sequence (e.g., by using an alignment program, such as BLAST or pileup). A library of mutant glutamyl tRNAs is generated using the consensus sequence; and an anticodon loop of each member of the library of mutant glutamyl tRNAs is mutated to allow recognition of a selector codon, thereby providing a library of potential O-tRNAs. A first population of cells of a first species, where the cells comprise a member of the library of potential O-tRNAs, is subjected to negative selection. The negative selection eliminates cells that comprise a member of the library of potential O-tRNAs that is aminoacylated by an aminoacyl-tRNA synthetase (RS) that is endogenous to the cell. This provides a pool of tRNAs that are orthogonal to the cell of the first species, thereby providing at least one glutamyl O-tRNA. An O-tRNA produced by the methods of the invention is also provided.

In certain embodiments, the methods further comprise mutating G10:U28 base pair to a G10:C28 base pair. In certain embodiments, the methods further comprise subjecting to positive selection a second population of cells of the first species, where the cells comprise a member of the pool of tRNAs that are orthogonal to the cell of the first species, a cognate aminoacyl-tRNA synthetase, and a positive selection marker. Using the positive selection, cells are selected or screened for those cells that comprise a member of the pool of tRNAs that is aminoacylated by the cognate aminoacyl-tRNA synthetase and that shows a desired response in the presence of the positive selection marker, thereby providing an O-tRNA. In certain embodiments, the second population of cells comprises cells that were not eliminated by the negative selection.

Methods for identifying an orthogonal glutamyl-aminoacyl-tRNA synthetase for use with a glutamyl O-tRNA are also provided. For example, methods include subjecting to selection a population of cells of a first species, where the cells each comprise: 1) a member of a plurality of aminoacyl-tRNA synthetases (RSs), (e.g., the plurality of RSs can include mutant RSs, RSs derived from a species other than a first species or both mutant RSs and RSs derived from a species other than a first species); 2) the orthogonal glutamyl tRNA (O-tRNA) (e.g., from one or more species); and 3) a polynucleotide that encodes a positive selection marker and comprises at least one selector codon. In certain embodiments, the glutamyl O-tRNA displays at least about, e.g., a 45%, a 50%, a 60%, a 75%, a 80%, or a 90% or more suppression efficiency in the presence of a cognate synthetase in response to a selector codon as compared to the glutamyl O-tRNA comprising or encoded by a polynucleotide sequence as set forth in SEQ ID NO.: 67 (AE(GC) tRNA).

Cells (e.g., a host cell) are selected or screened for those that show an enhancement in suppression efficiency compared to cells lacking or having a reduced amount of the member of the plurality of RSs. These selected/screened cells comprise an active RS that aminoacylates the Q-tRNA. The level of aminoacylation (in vitro or in vivo) by the active RS of a first set of tRNAs from the first species is compared to the level of aminoacylation (in vitro or in vivo) by the active RS of a second set of tRNAs from a second species (e.g., where the second species is other than the first species); where the level of aminoacylation is determined by a detectable substance (e.g., a labeled amino acid). The active RS that more efficiently aminoacylates the second set of tRNAs compared to the first set of tRNAs is selected, thereby providing the glutamyl orthogonal aminoacyl-tRNA synthetase, e.g., glutamyl O-RS, for use with the glutamyl O-tRNA. An orthogonal aminoacyl-tRNA synthetase identified by the method is also a feature of the invention.

Methods of producing a protein in a cell (e.g., a non-eukaryotic cell, such as an *E. coli* cell or the like, or a eukaryotic cell) with a selected amino acid at a specified position are also a feature of the invention. For example, a method includes growing, in an appropriate medium, a cell, where the cell comprises a nucleic acid that comprises at least one selector codon and encodes a protein, providing the selected amino acid, incorporating the selected amino acid into the specified position in the protein during translation of the nucleic acid with the at least one selector codon, thereby producing the protein. The cell further comprises: a glutamyl-tRNA (glutamyl O-tRNA) that functions in the cell and recognizes the selector codon; and, an orthogonal glutamyl aminoacyl-tRNA synthetase (glutamyl O-RS) that preferentially aminoacylates the glutamyl-O-tRNA with the selected amino acid. Typically, the glutamyl O-tRNA comprises at least about, e.g., a 45%, a 50%, a 60%, a 75%, a 80%, or a 90% or more suppression efficiency in the presence of a cognate synthetase in response to the selector codon as compared to the glutamyl O-tRNA comprising or encoded by a polynucleotide sequence as set forth in SEQ ID NO.: 67 (AE(GC) tRNA). A protein produced by this method is also a feature of the invention.

DEFINITIONS

Before describing the invention in detail, it is to be understood that this invention is not limited to particular biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a cell" includes a combination of two or more cells; reference to "bacteria" includes mixtures of bacteria, and the like.

Unless defined herein and below in the reminder of the specification, all technical and scientific terms used herein have the same meaning as commonly understood by one of ordinary skill in the art to which the invention pertains.

Orthogonal glutamyl-tRNA: As used herein, an orthogonal glutamyl-tRNA (glutamyl-O-tRNA) is a tRNA that is orthogonal to a translation system of interest, where the tRNA is: (1) identical or substantially similar to a naturally occurring glutamyl tRNA, (2) derived from a naturally occurring glutamyl tRNA by natural or artificial mutagenesis, (3) derived by any process that takes a sequence of a wild-type or mutant glutamyl tRNA sequence of (1) or (2) into account, (4) homologous to a wild-type or mutant glutamyl tRNA; (5) homologous to any example tRNA that is designated as a substrate for a glutamyl tRNA synthetase in TABLE 3, or (6) a conservative variant of any example tRNA that is designated as a substrate for a glutamyl tRNA synthetase in TABLE 3. The glutamyl tRNA can exist charged with a amino acid, or in an uncharged state. It is also to be understood that a "glutamyl-O-tRNA" optionally is charged (aminoacylated) by a cognate synthetase with an amino acid other than glutamic acid. Indeed, it will be appreciated that a glutamyl-O-tRNA of the invention is advantageously used to insert essentially any amino acid, whether natural or artificial, into a growing polypeptide, during translation, in response to a selector codon, Orthogonal glutamyl amino acid synthetase: As used herein, an orthogonal glutamyl amino acid synthetase (glutamyl-O-RS) is an enzyme that preferentially aminoacylates the glutamyl-O-tRNA with an amino acid in a translation system of interest. The amino acid that the glutamyl-O-RS loads onto the glutamyl-O-tRNA can be any amino acid, whether natural or artificial, and is not limited herein. The synthetase is optionally the same as or homologous to a naturally occurring glutamyl amino acid synthetase, or the same as or homologous to a synthetase designated as a glutamyl-O-RS in TABLE 3. For example, the glutamyl-O-RS can be a conservative variant of a glutamyl-O-RS of TABLE 3, and/or can be at least 50%, 60%, 70%, 80%, 90%, 95%, 98%, 99% or more identical in sequence to a glutamyl-O-RS of TABLE 3.

Orthogonal: As used herein, the term "orthogonal" refers to a molecule (e.g., an orthogonal tRNA (O-tRNA) and/or an orthogonal aminoacyl tRNA synthetase (O-RS)) that functions with endogenous components of a cell with reduced efficiency as compared to a corresponding molecule that is endogenous to the cell or translation system, or that fails to function with endogenous components of the cell. In the context of tRNAs and aminoacyl-tRNA synthetases, orthogonal refers to an inability or reduced efficiency, e.g., less than 20% efficiency, less than 10% efficiency, less than 5% efficiency, or less than 1% efficiency, of an orthogonal tRNA to function with an endogenous tRNA synthetase compared to an endogenous tRNA to function with the endogenous tRNA synthetase, or of an orthogonal aminoacyl-tRNA synthetase to function with an endogenous tRNA compared to an endogenous tRNA synthetase to function with the endogenous tRNA. The orthogonal molecule lacks a functionally normal endogenous complementary molecule in the cell. For example, an orthogonal tRNA in a cell is aminoacylated by any endogenous RS of the cell with reduced or even zero efficiency, when compared to aminoacylation of an endogenous tRNA by the endogenous RS. In another example, an orthogonal RS aminoacylates any endogenous tRNA a cell of interest with reduced or even zero efficiency, as compared to aminoacylation of the endogenous tRNA by an endogenous RS. A second orthogonal molecule can be introduced into the cell that function with the first orthogonal molecule. For example, an orthogonal tRNA/RS pair includes introduced complementary components that function together in the cell with an efficiency (e.g., 45% efficiency, 50% efficiency, 60% efficiency, 70% efficiency, 75% efficiency, 80% efficiency, 90% efficiency, 95% efficiency, or 99% or more efficiency) as compared to that of a control, e.g., a corresponding tRNA/RS endogenous pair, or an active orthogonal pair (e.g., a tyrosyl orthogonal tRNA/RS pair).

Cognate: The term "cognate" refers to components that function together, e.g., a glutamyl tRNA and a glutamyl aminoacyl-tRNA synthetase. The components can also be referred to as being complementary.

Preferentially aminoacylates: The term "preferentially aminoacylates" refers to an efficiency, e.g., 70% efficiency, 75% efficiency, 85% efficiency, 90% efficiency, 95% efficiency, or 99% or more efficiency, at which an O-RS aminoacylates an O-tRNA with a selected amino acid, e.g., an unnatural amino acid, as compared to the O-RS aminoacylating a naturally occurring tRNA or a starting material used to generate the O-tRNA.

Selector codon: The term "selector codon" refers to codons recognized by the O-tRNA in the translation process and typically not recognized by an endogenous tRNA. The O-tRNA anticodon loop recognizes the selector codon on the mRNA and incorporates its amino acid, e.g., a selected amino acid, such as an unnatural amino acid, at this site in the polypeptide. Selector codons can include, e.g., nonsense codons, such as, stop codons, e.g., amber, ochre, and opal codons; four or more base codons; rare codons; codons derived from natural or unnatural base pairs and/or the like.

Suppressor tRNA: A suppressor tRNA is a tRNA that alters the reading of a messenger RNA (mRNA) in a given translation system, e.g., by providing a mechanism for incorporating an amino acid into a polypeptide chain in response to a selector codon. For example, a suppressor tRNA can read through, e.g., a stop codon, a four base codon, a rare codon, etc.

Suppression activity: As used herein, the term "suppression activity" refers, in general, to the ability of a tRNA (e.g., a suppressor tRNA) to allow translational read-through of a codon (e.g. a selector codon that is an amber codon or a 4-or-more base codon) that would otherwise result in the termination of translation or mistranslation (e.g., frame-shifting). Suppression activity of a suppressor tRNA can be expressed as a percentage of translational read-through observed compared to a second suppressor tRNA, or as compared to a control system, e.g., a control system lacking an O-RS.

The present invention provides various means by which suppression activity can be quantitated. Percent suppression of a particular O-tRNA and O-RS against a selector codon (e.g., an amber codon) of interest refers to the percentage of activity of a given expressed test marker (e.g., LacZ), that includes a selector codon, in a nucleic acid encoding the expressed test marker, in a translation system of interest, where the translation system of interest includes an O-RS and an O-tRNA, as compared to a positive control construct, where the positive control lacks the O-tRNA, the O-RS and the selector codon. Thus, for example, if an active positive control marker construct that lacks a selector codon has an observed activity of X in a given translation system, in units relevant to the marker assay at issue, then percent suppression of a test construct comprising the selector codon is the percentage of X that the test marker construct displays under essentially the same environmental conditions as the positive control marker was expressed under, except that the test marker construct is expressed in a translation system that also includes the O-tRNA and the O-RS. Typically, the translation system expressing the test marker also includes an amino acid that is recognized by the O-RS and O-tRNA. Optionally, the percent suppression measurement can be refined by comparison of the test marker to a "background" or "negative" control marker construct, which includes the same selector codon as the test marker, but in a system that does not include the O-tRNA, O-RS and/or relevant amino acid recognized by the O-tRNA and/or O-RS. This negative control is useful in normalizing percent suppression measurements to account for background signal effects from the marker in the translation system of interest.

Suppression efficiency can be determined by any of a number of assays known in the art. For example, a β-galactosidase reporter assay can be used, e.g., a derivatized lacZ plasmid (where the construct has a selector codon in the lacZ nucleic acid sequence) is introduced into cells from an appropriate organism (e.g., an organism where the orthogonal components can be used) along with plasmid comprising an O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and β-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatived lacZ construct, where the construct has a corresponding sense codon at desired position rather than a selector codon.

Translation system: The term "translation system" refers to the components that incorporate an amino acid into a growing polypeptide chain (protein). Components of a translation system can include, e.g., ribosomes, tRNAs, synthetases, mRNA and the like. The O-tRNA and/or the O-RSs of the invention can be added to or be part of an in vitro or in vivo translation system, e.g., in a non-eukaryotic cell, e.g., a bacterium (such as *E. coli*), or in a eukaryotic cell, e.g., a yeast cell, a mammalian cell, a plant cell, an algae cell, a fungus cell, an insect cell, and/or the like.

Selected amino acid: The term "selected amino acid" refers to any desired naturally occurring amino acid or unnatural amino acid. As used herein, the term "unnatural amino acid" refers to any amino acid, modified amino acid, and/or amino acid analogue that is not one of the 20 common naturally occurring amino acids or seleno cysteine or pyrrolysine.

Derived from: As used herein, the term "derived from" refers to a component that is isolated from or made using a specified molecule or organism, or information from the specified molecule or organism.

Positive selection or screening marker: As used herein, the term "positive selection or screening marker" refers to a marker that, when present, e.g., expressed, activated, or the like, results in identification of a cell, which comprise the trait, e.g., cells with the positive selection marker, from those without the trait.

Negative selection or screening marker: As used herein, the term "negative selection or screening marker" refers to a marker that when present, e.g., expressed, activated, or the like, allows identification of a cell that does not comprise a specified property or trait (e.g., as compared to a cell that does possess the property or trait).

Reporter: As used herein, the term "reporter" refers to a component that can be used to identify and/or select target components of a system of interest. For example, a reporter can include a protein, e.g., an enzyme, that confers antibiotic resistance or sensitivity (e.g., β-lactamase, chloramphenicol acetyltransferase (CAT), and the like), a fluorescent screening marker (e.g., green fluorescent protein (e.g., (GFP), YFP, EGPP, RFP, etc.), a luminescent marker (e.g., a firefly luciferase protein), an affinity based screening marker, or positive or negative selectable marker genes such as lacZ, β-gal/lacZ (β-galactosidase), Adh (alcohol dehydrogenase), his3, ura3, leu2, lys2, or the like.

Eukaryote: As used herein, the term "eukaryote" refers to organisms belonging to the phylogenetic domain Eucarya, such as animals (e.g., mammals, insects, reptiles, birds, etc.), ciliates, plants (e.g., monocots, dicots, algae, etc.), fungi, yeasts, flagellates, microsporidia, protists, etc.

Non-eukaryote: As used herein, the term "non-eukaryote" refers to non-eukaryotic organisms. For example, a non-eukaryotic organism can belong to the Eubacteria (e.g., *Escherichia coli, Thermus thermophilus, Bacillus stearothermophilus*, etc.) phylogenetic domain, or the Archaea (e.g., *Methanococcus jannaschii* (Mj), *Methanosarcina mazei* (Mm), *Methanobacterium thermoautotrophicum* (Mt), *Methanococcus maripaludis, Methanopyrus kandleri, Halobacterium* such as *Haloferax volcanii* and *Halobacterium* species NRC-1, *Archaeoglobus fulgidus* (Af), *Pyrococcus furiosus* (Pf), *Pyrococcus horikoshii* (Ph), *Pyrobaculum aerophilum, Pyrococcus abyssi, Sulfolobus solfataricus* (Ss), *Sulfolobus tokodaii, Aeuropyrum pernix* (Ap), *Thermoplasma acidophilum, Thermoplasma volcanium*, etc.) phylogenetic domains.

Conservative variant: As used herein, the term "conservative variant" refers to a translation component, e.g., a conservative variant O-tRNA or a conservative variant O-RS, that functionally performs similar to a base component from which the conservative variant is based, e.g., an O-tRNA or O-RS, but having variations in the sequence. For example, an O-RS will aminoacylate a complementary O-tRNA or a conservative variant O-tRNA with a selected amino acid, e.g., an unnatural amino acid, although the O-tRNA and the conservative variant O-tRNA do not have the same sequence. The conservative variant can have, e.g., one variation, two variations, three variations, four variations, or five or more variations in sequence, as long as the conservative variant is complementary to the corresponding O-tRNA or O-RS.

Selection or screening agent: As used herein, the term "selection or screening agent" refers to an agent that, when present, allows for a selection/screening of certain components from a population. For example, a selection or screening agent includes, but is not limited to, e.g., a nutrient, an antibiotic, a wavelength of light, an antibody, an expressed polynucleotide, or the like. The selection agent can be varied, e.g., by concentration, intensity, etc.

In response to: As used herein, in the context of translation with O-tRNA and O-RS components, the term "in response to" refers to the process in which a tRNA of the invention recognizes a selector codon and incorporates the selected amino acid, which is bound to tRNA, into the growing polypeptide chain.

Exogenous or heterologous: As used herein, the terms "exogenous" or "heterologous" as applied to polynucleotides or polypeptides refers to molecules that have been artificially supplied to a biological system (e.g., a cell) and are not native to that particular biological system. The terms indicate that the relevant material originated from a source other than the naturally occurring source, or refers to molecules having a non-natural configuration, genetic location or arrangement of parts. The terms "exogenous" and "heterologous" are sometimes used interchangeably with "recombinant."

In contrast, for example, a "native" or "endogenous" gene is a gene that does not contain nucleic acid elements encoded by sources other than the chromosome or other genetic element on which it is normally found in nature. An endogenous gene, transcript or polypeptide is encoded by its natural chromosomal locus, and not artificially supplied to the cell.

Encode: As used herein, the term "encode" refers to any process whereby the information in a polymeric macromolecule or sequence string is used to direct the production of a second molecule or sequence string that is different from the first molecule or sequence string. As used herein, the term is used broadly, and can have a variety of applications. In one aspect, the term "encode" describes the process of semi-conservative DNA replication, where one strand of a double-stranded DNA molecule is used as a template to encode a newly synthesized complementary sister strand by a DNA-dependent DNA polymerase.

In another aspect, the term "encode" refers to any process whereby the information in one molecule is used to direct the production of a second molecule that has a different chemical nature from the first molecule. For example, a DNA molecule can encode an RNA molecule (e.g., by the process of transcription incorporating a DNA-dependent RNA polymerase enzyme). Also, an RNA molecule can encode a polypeptide, as in the process of translation. When used to describe the process of translation, the term "encode" also extends to the triplet codon that encodes an amino acid. In some aspects, an RNA molecule can encode a DNA molecule, e.g., by the process of reverse transcription incorporating an RNA-dependent DNA polymerase. In another aspect, a DNA molecule can encode a polypeptide, where it is understood that "encode" as used in that case incorporates both the processes of transcription and translation.

BRIEF DESCRIPTION OF THE FIGURES

FIG. 4, Panels A, B and C illustrate optimization of the AE(GU) tRNA by selection. Panel A schematically illustrates sequence and secondary structure of the AE(NN) tRNA library, which differs from the AE(GU) tRNA only at positions 10 and 28, which are randomized. Underlined bases correspond to positions that vary from the consensus sequence; tRNA anticodons are boxed. Panel B schematically illustrates sequence and secondary structure of the AE(GC) tRNA, which is identified as the most active tRNA within the AE(NN) library. Panel C provides a histogram demonstrating aminoacylation of the AE(GC) tRNA in *E. coli*, e.g., using a β-lactamase assay to measure the ampicillin $IC_{50}$ values for *E. coli* expressing the indicated glutamyl-tRNA synthetases together with the AE(GC) tRNA or the AE(GC) tRNA with no synthetase.

DETAILED DESCRIPTION

Figure 1A:
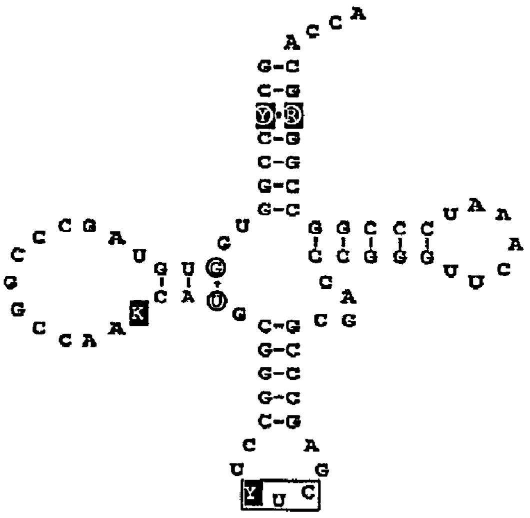
FIG. 1, Panels A and B schematically illustrate design of orthogonal tRNAs. Panel A schematically illustrates consensus archaeal $tRNA^{Glu}$ and $tRNA^{Gln}$ sequences. Non-canonical base pairs are circled; tRNA anticodons are boxed. Highlighted bases correspond to positions at which two different bases predominate approximately equally. K corresponds to bases G or U; Y corresponds to bases C or U; R corresponds to bases A or G; S corresponds to bases C or G. Panel B schematically illustrates initial candidate orthogonal tRNAs. Underlined bases correspond to positions that vary from the consensus sequence.
Figure 1A:
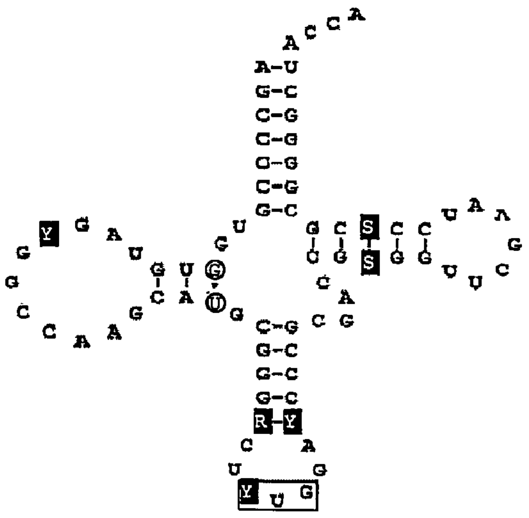
Figure 1B:
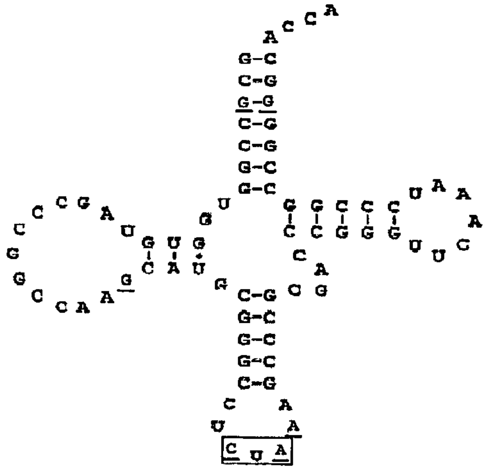
Figure 1B:
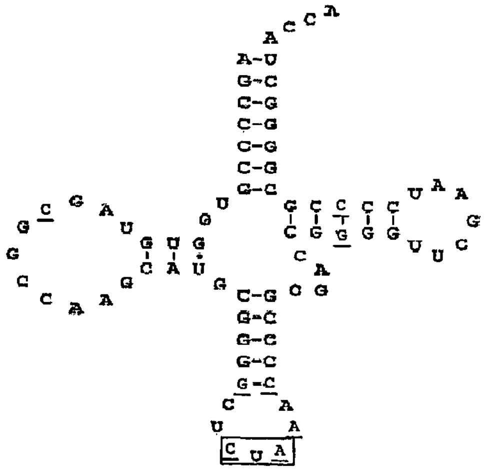
Figure 1B:
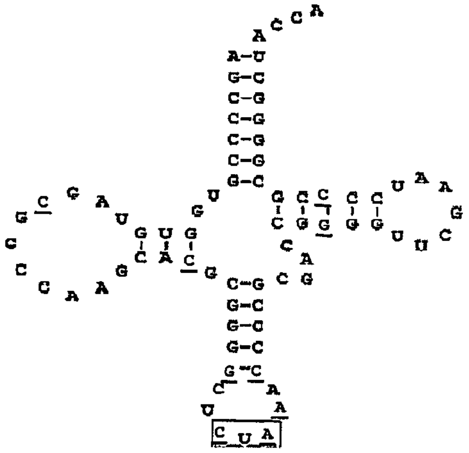

In order to add additional unnatural amino acids to the genetic code in vivo, "orthogonal pairs" of an aminoacyl-tRNA synthetase and a tRNA are needed that can function efficiently in the translational machinery. These pairs are orthogonal to a given translation system's other elements, e.g., the endogenous RS and tRNA of the system. Desired characteristics of the orthogonal pairs include tRNA that decode or recognize only a specific new codon, e.g., a selector codon, that is not decoded by any endogenous tRNA, and aminoacyl-tRNA synthetases that preferentially aminoacylate (or charge) its cognate tRNA with only a specific selected amino acid, e.g., an unnatural amino acid. The O-tRNA is also not typically aminoacylated by endogenous synthetases. For example, in *E. coli*, an orthogonal pair will include an aminoacyl-tRNA synthetase that does not significantly cross-react with any of the endogenous tRNA, which there are 40 in *E. coli*, and an orthogonal tRNA that is not significantly aminoacylated by any of the endogenous synthetases, e.g., of which there are 21 in *E. coli.*

This invention provides compositions of and methods for identifying and producing additional orthogonal tRNA-aminoacyl-tRNA synthetase pairs, e.g., glutamyl O-tRNA/glutamyl O-RS pairs. A glutamyl O-tRNA of the invention is capable of mediating incorporation of a selected amino acid into a protein that is encoded by a polynucleotide, which comprises a selector codon that is recognized by the glutamyl O-tRNA, e.g., in vivo. The anticodon loop of the glutamyl O-tRNA recognizes the selector codon on an mRNA and incorporates its amino acid, e.g., a selected amino acid, such as an unnatural amino acid, at this site in the polypeptide. An orthogonal glutamyl aminoacyl-tRNA synthetase of the invention preferentially aminoacylates (or "charges") its glutamyl O-tRNA with only a specific selected amino acid.

Orthogonal Glutamyl tRNA/Orthogonal Glutamyl Aminoacyl-tRNA Synthetases and Pairs Thereof Other features of translation systems that are suitable for making proteins that include one or more selected amino acids, e.g., an unnatural amino acid, are described in Published International Applications WO 2002/086075, entitled "METHODS AND COMPOSITION FOR THE PRODUCTION OF ORTHOGONAL tRNA-AMINOACYL-tRNA SYNTHETASE PAIRS" and WO 2002/085923, entitled "IN VIVO INCORPORATION OF UNNATURAL AMINO ACIDS." In addition, see International Application Number PCT/US2004/011786, filed Apr. 16, 2004. Each of these applications is incorporated herein by reference in its entirety. These translation systems can be adopted to the present invention by the inclusion of an O-RS/O-tRNA of the invention.

Translation systems on the invention generally comprise cells (e.g., non-eukaryotic cells, or eukaryotic cells) that include an orthogonal glutamyl tRNA (glutamyl O-tRNA), an orthogonal glutamyl aminoacyl tRNA synthetase (glutamyl O-RS), and a selected amino acid, where the glutamyl O-RS aminoacylates the glutamyl O-tRNA with the selected amino acid. An orthogonal pair of the invention includes of a glutamyl O-tRNA, e.g., a suppressor tRNA, a frameshift tRNA, or the like, and a glutamyl O-RS. Individual components are also provided in the invention.

The glutamyl O-tRNA herein recognizes a selector codon and includes at least about, e.g., a 45%, a 50%, a 60%, a 75%, a 80%, or a 90% or more suppression efficiency in the presence of a cognate synthetase in response to a selector codon as compared to the glutamyl O-tRNA comprising or encoded by a polynucleotide sequence as set forth in SEQ ID NO.: 67 (AE(GC) tRNA) in the presence of a cognate O-RS. The cognate glutamyl O-RS aminoacylates the O-tRNA with a selected amino acid. The cell or other translation system uses the components to incorporate the selected amino acid into a growing polypeptide chain, e.g., via a nucleic acid that comprises a polynucleotide that encodes a polypeptide of interest, where the polynucleotide comprises a selector codon that is recognized by the glutamyl O-tRNA. In certain embodiments of the invention, a cell includes an *E. coli* cell that includes an orthogonal glutamyl tRNA (glutamyl O-tRNA), an orthogonal glutamyl aminoacyl-tRNA synthetase (glutamyl O-RS), a selected amino acid; and, a nucleic acid that comprises a polynucleotide that encodes a polypeptide of interest, where the polynucleotide comprises the selector codon that is recognized by the glutamyl O-tRNA. The translation system can also be an in vitro system.

In one embodiment, the suppression efficiency of the glutamyl O-RS and the glutamyl O-tRNA together is about, e.g., 5 fold, 10 fold, 15 fold, 20 fold, or 25 fold or more greater than the suppression efficiency of the glutamyl O-tRNA lacking the glutamyl O-RS. In one aspect, the suppression efficiency of the glutamyl O-RS and the glutamyl O-tRNA together is at least about, e.g., 35%, 40%, 45%, 50%, 60%, 75%, 80%, or 90% or more of the suppression efficiency of an orthogonal tyrosyl-tRNA synthetase pair derived from *Methanococcus jannaschii*.

The invention also features multiple O-tRNA/O-RS pairs in a cell, which allows incorporation of more than one selected amino acid. For example, the cell can further include an additional different O-tRNA/O-RS pair and a second selected amino acid, where this additional O-tRNA recognizes a second selector codon and this additional O-RS preferentially aminoacylates the O-tRNA with the second selected amino acid. For example, a cell, which includes a glutamyl O-tRNA/O-RS pair (where the glutamyl O-tRNA recognizes, e.g., an amber selector codon), can further comprise a second orthogonal pair, e.g., leucyl, lysyl, tyrosyl, etc., (where the second O-tRNA recognizes a different selector codon, e.g., an opal, four-base, or the like).

The glutamyl O-tRNA and/or the glutamyl O-RS can be naturally occurring or can be derived by mutation of a naturally occurring or consensus or hypothetical tRNA and/or RS, e.g., by generating libraries of tRNAs and/or libraries of RSs, from a variety of organisms. For example, one strategy of producing an orthogonal glutamyl tRNA/glutamyl aminoacyl-tRNA synthetase pair involves importing a heterologous (to the host cell) tRNA/synthetase pair from, e.g., a source other than the host cell, or multiple sources, into the host cell. The properties of the heterologous synthetase candidate include, e.g., that it does not significantly charge any host cell tRNA, and the properties of the heterologous tRNA candidate include, e.g., that it is not aminoacylated by any host cell synthetase. In addition, the heterologous tRNA is orthogonal to all host cell synthetases.

A second strategy for generating an orthogonal pair involves generating mutant libraries from which to screen and/or select a glutamyl O-tRNA or glutamyl O-RS. These strategies can also be combined.

Archaea is a good source of orthogonal pairs for, e.g., *E. coli*. Previous studies revealed that several archaeal tRNAs are not recognized by *E. coli* aminoacyl-tRNA synthetases (see, e.g., Kwok and Wong, (1980) *Evolutionary relationship between Halobacterium cutirubrum and eukaryotes determined by use of aminoacyl-tRNA synthetases as phylogenetic probes, Can. J. Biochem.*, 58:213-218). Two such synthetase-tRNA pairs derived from archaea, for tyrosine (see, e.g., Wang et al., (2000) *A new functional suppressor tRNA/aminoacyl-tRNA synthetase pair for the in vivo incorporation of unnatural amino acids into proteins, J. Am. Chem. Soc.*, 122: 5010-5011) and leucine (see, e.g., Anderson J C, & Schultz P G, (2003), *Adaptation of an orthogonal archaeal leucyl-tRNA and synthetase pair for four-base, amber, and opal suppression, Biochemistry*, August 19; 42(32):9598-9608), were developed for use, e.g., in *E. coli*. Both exhibited high levels of orthogonality and amber suppression efficiency. Moreover, these archaeal synthetases and tRNAs are efficiently produced and processed in *E. coli*. Finally, the recent proliferation of genomic sequence data for archaeal species and the commercial availability of their genomic DNA have facilitated the cloning of synthetases from these organisms, as well as the design of compatible tRNAs.

In addition, archaeal glutamyl-tRNA synthetases and tRNAs are good sources for the production of additional orthogonal pairs for several reasons. Archaeal glutamyl-tRNA synthetases are expected to tolerate changes in the anticodon loop of their substrate tRNAs since the enzyme naturally accommodates four different tRNA anticodons: UUC, CUC, UUG, and CUG. This is due to the fact that in archaeal species, glutamyl-tRNA synthetases must recognize and acylate both $tRNA^{Glu}$ and $tRNA^{Gln}$ (see, e.g., Tumbula et al., (2000) *Domain-specific recruitment of amide amino acids for protein synthesis, Nature* 407:106-110). An archaeal glutamyl-tRNA synthetase can tolerate variance within at least two positions of the anticodon of its tRNA substrate, which can permit efficient aminoacylation of a tRNA bearing, e.g., an amber-suppressing CUA anticodon. In addition, in vitro aminoacylation data (see, e.g., Kwok and Wong (1980) *Evolutionary relationship between Halobacterium cutirubrum and eukaryotes determined by use of aminoacyl-tRNA synthetases as phylogenetic probes, Can. J. Biochem.*, 58:213-218) predict that archaeal glutamic acid and glutamine tRNAs should be orthogonal in *E. coli*. Finally, the three dimensional structure of the glutamyl-tRNA synthetase from *Thermus thermophilus* is known (see, e.g., Nureki et al., (1995) *Architectures of class-defining and specific domains of glutamyl-tRNA synthetase, Science* 31: 1958-1965), which can facilitate the design of libraries of synthetase variants for use in directed evolution experiments. See the section entitled "Sources and Hosts," herein, for additional information.

Orthogonal tRNA (O-tRNA)

An orthogonal glutamyl tRNA (glutamyl O-tRNA) mediates incorporation of a selected amino acid into a protein that is encoded by a polynucleotide that comprises a selector codon that is recognized by the glutamyl O-tRNA, e.g., in vivo or in vitro. Typically, a glutamyl O-tRNA of the invention includes at least about, e.g., a 45%, a 50%, a 60%, a 75%, a 80%, or a 90% or more suppression efficiency in the presence of a cognate synthetase in response to a selector codon as compared to the glutamyl O-tRNA comprising or encoded by a polynucleotide sequence as set forth in SEQ ID NO.: 67 (AE(GC) tRNA) in the presence of a cognate RS.

Suppression efficiency can be determined by any of a number of assays known in the art. For example, a β-galactosidase reporter assay can be used, e.g., a derivatized lacZ plasmid (where the construct has a selector codon n the lacZ nucleic acid sequence) is introduced into cells from an appropriate organism (e.g., an organism where the orthogonal components can be used) along with plasmid comprising a O-tRNA of the invention. A cognate synthetase can also be introduced (either as a polypeptide or a polynucleotide that encodes the cognate synthetase when expressed). The cells are grown in media to a desired density, e.g., to an $OD_{600}$ of about 0.5, and O-galactosidase assays are performed, e.g., using the BetaFluor™ β-Galactosidase Assay Kit (Novagen). Percent suppression can be calculated as the percentage of activity for a sample relative to a comparable control, e.g., the value observed from the derivatived lacZ construct, where the construct has a corresponding sense codon at desired position rather than a selector codon.

An example of a glutamyl O-tRNA of the invention is a polynucleotide sequence comprising SEQ D) NO.: 67. See Table 3 and Example 2, herein, for sequences of exemplary O-tRNA and O-RS molecules. See also, the section entitled "Nucleic Acid and Polypeptide Sequence and Variants" herein. In the tRNA molecule, Thymine (T) is replaced with Uracil (U). The glutamyl O-tRNA of the invention also optionally includes a G:C base pair at position 10:28. Additional modifications to the bases can also be present. The invention also includes conservative variations of glutamyl O-tRNA. For example, conservative variations of glutamyl O-tRNA include those molecules that function like the glutamyl O-tRNA of SEQ ID NO.: 67 and maintain the tRNA L-shaped structure, but do not have the same sequence (and are other than wild type glutamyl tRNA molecules). See also, the section herein entitled "Nucleic acids and Polypeptides Sequence and Variants."

The composition comprising a glutamyl O-tRNA can further include an orthogonal glutamyl aminoacyl-tRNA synthetase (glutamyl O-RS), where the glutamyl O-RS preferentially aminoacylates the glutamyl O-tRNA with a selected amino acid. In certain embodiments, a composition including a glutamyl O-tRNA can further include a translation system (e.g., in vitro or in vivo). A nucleic acid that comprises a polynucleotide that encodes a polypeptide of interest, where the polynucleotide comprises a selector codon that is recognized by the glutamyl O-tRNA, or a combination of one or more of these can also be present in the cell. See also the section herein entitled "Orthogonal aminoacyl-tRNA synthetases."

Methods of producing an orthogonal glutamyl tRNA (glutamyl O-tRNA) are also a feature of the invention. A glutamyl O-tRNA produced by the method is also a feature of the invention. In certain embodiments of the invention, the glutamyl O-tRNAs can be produced by a consensus strategy. For example, potential orthogonal glutamyl tRNAs can be produced by aligning a plurality of glutamyl tRNA sequences (e.g., derived from a species other than a host cell's species, derived from an archaeal species, etc.); determining a consensus sequence; and, generating a library of mutant glutamyl tRNAs using the consensus sequence.

For example, a consensus sequence can be compiled with a computer program, e.g., the GCG program pileup or BLAST. Optionally, degenerate positions determined by the program are changed to the most frequent base at those positions. The library of mutant tRNAs can be generated using various mutagenesis techniques known in the art. For example, the mutant tRNAs can be generated by site-specific mutations, random point mutations, homologous recombination, DNA shuffling or other recursive mutagenesis methods, chimeric construction or any combination thereof. In one embodiment of the invention, overlap extension of oligonucleotides in which each site of the tRNA gene can be synthesized as a doped mixture of 90% the consensus sequence and 10% a mixture of the other 3 bases can be used to provide the library based on the consensus sequence. Other mixtures can also be used, e.g., 75% the consensus sequence and 25% a mixture of the other 3 bases, 80% the consensus sequence and 20% a mixture of the other 3 bases, 95% the consensus sequence and 5% a mixture of the other 3 bases, etc.

Additional mutations can be introduced at specific position(s), e.g., at nonconservative position(s), or at conservative position(s), at randomized position(s), or a combination of each in a desired loop or region of a tRNA, e.g., an anticodon loop, the acceptor stem, D arm or loop, variable loop, TψC arm or loop, other regions of the tRNA molecule, or a combination thereof. Typically, mutations in a glutamyl tRNA include mutating the anticodon loop of each member of the library of mutant glutamyl tRNAs to allow recognition of a selector codon. In one embodiment, mutations include a G10:C28 base pair. The method can further include adding an additional sequence (CCA) to a 3' terminus of the O-tRNA.

Optionally, the secondary structure of a member of the library of potential glutamyl O-tRNAs can be analyzed to identify non-canonical base pairs in the secondary structure, and optionally methods of the invention include mutating the non-canonical base pairs (e.g., the non-canonical base pairs are mutated to canonical base pairs). Typically, a glutamyl O-tRNA possesses an improvement of orthogonality for a desired organism compared to the starting material, e.g., the plurality of tRNA sequences, while preserving its affinity towards a desired RS.

The methods optionally include analyzing the homology of sequences of tRNAs and/or aminoacyl-tRNA synthetases to determine potential candidates for an O-tRNA, O-RS, and/or pairs thereof, that appear to be orthogonal for a specific organism. Computer programs known in the art and described herein can be used for the analysis. In one example, to choose potential orthogonal translational components for use in *E. coli*, a prokaryotic organism, a synthetase and/or a tRNA is chosen that does not display unusual homology to prokaryotic organisms.

Typically, a glutamyl O-tRNA is obtained by subjecting to, e.g., negative selection, a population of cells of a first species, where the cells comprise a member of the plurality of potential glutamyl O-tRNAs. The negative selection eliminates cells that comprise a member of the library of potential glutamyl O-tRNAs that is aminoacylated by an aminoacyl-tRNA synthetase (RS) that is endogenous to the cell. This provides a pool of glutamyl tRNAs that are orthogonal to the cell of the first species.

In certain embodiments, in the negative selection, a selector codon(s) is introduced into polynucleotide that encodes a negative selection marker, e.g., an enzyme that confers antibiotic resistance, e.g., β-lactamase, an enzyme that confers a detectable product, e.g., β-galactosidase, chloramphenicol acetyltransferase (CAT), e.g., a toxic product, such as barnase, at a nonessential position (e.g., still producing a functional barnase), etc. Screening/selection is optionally done by growing the population of cells in the presence of a selective agent (e.g., an antibiotic, such as ampicillin). In one embodiment, the concentration of the selection agent is varied.

For example, to measure the activity of suppressor glutamyl tRNAs, a selection system is used that is based on the in vivo suppression of selector codon, e.g., nonsense or frameshift mutations introduced into a polynucleotide that encodes a negative selection marker, e.g., a gene for β-lactamase (bla). For example, polynucleotide variants, e.g., bla variants, with a selector codon at a certain position (e.g., A184), are constructed. Cells, e.g., bacteria, are transformed with these polynucleotides. In the case of an orthogonal glutamyl tRNA, which cannot be efficiently charged by endogenous *E. coli* synthetases, antibiotic resistance, e.g., ampicillin resistance, should be about or less than that for a bacteria transformed with no plasmid. If the glutamyl tRNA is not orthogonal, or if a heterologous synthetase capable of charging the tRNA is co-expressed in the system, a higher level of antibiotic, e.g., ampicillin, resistance is be observed. Cells, e.g., bacteria, are chosen that are unable to grow on LB agar plates with antibiotic concentrations about equal to cells transformed with no plasmids.

In the case of a toxic product (e.g., ribonuclease or barnase), when a member of the plurality of potential glutamyl tRNAs is aminoacylated by endogenous host, e.g., *Escherichia coli* synthetases (i.e., it is not orthogonal to the host, e.g., *Escherichia coli* synthetases), the selector codon is suppressed and the toxic polynucleotide product produced leads to cell death. Cells harboring orthogonal glutamyl tRNAs or non-functional tRNAs survive.

In one embodiment, the pool of glutamyl tRNAs that are orthogonal to a desired organism are then subjected to a positive selection in which a selector codon is placed in a positive selection marker, e.g., encoded by a drug resistance gene, such a β-lactamase gene. The positive selection is performed on a cell comprising a polynucleotide encoding or comprising a member of the pool of tRNAs that are orthogonal to the cell, a polynucleotide encoding a positive selection marker, and a polynucleotide encoding a cognate RS. In certain embodiments, the second population of cells comprises cells that were not eliminated by the negative selection. The polynucleotides are expressed in the cell and the cell is grown in the presence of a selection agent, e.g., ampicillin. Glutamyl tRNAs are then selected for their ability to be aminoacylated by the coexpressed cognate synthetase and to insert an amino acid in response to this selector codon. Typically, these cells show an enhancement in suppression efficiency compared to cells harboring non-functional tRNA(s), or tRNAs that cannot efficiently be recognized by the synthetase of interest. The cell harboring the non-functional tRNA(s) or tRNAs that are not efficiently recognized by the synthetase of interest, are sensitive to the antibiotic. Therefore, glutamyl tRNAs that: (i) are not substrates for endogenous host, e.g., *Escherichia coli*, synthetases; (ii) can be aminoacylated by the synthetase of interest; and (iii) are functional in translation, survive both selections.

The stringency of the selection, e.g., the positive selection, the negative selection or both the positive and negative selection, in the above described-methods, optionally includes varying the selection stringency. For example, because barnase is an extremely toxic protein, the stringency of the negative selection can be controlled by introducing different numbers of selector codons into the barnase gene and/or by using an inducible promoter. In another example, the concentration of the selection or screening agent is varied (e.g., ampicillin concentration). In one aspect of the invention, the stringency is varied because the desired activity can be low during early rounds. Thus, less stringent selection criteria are applied in early rounds and more stringent criteria are applied in later rounds of selection. In certain embodiments, the negative selection, the positive selection or both the negative and positive selection, can be repeated multiple times. Multiple different negative selection markers, positive selection markers or both negative and positive selection markers, can be used. In certain embodiments, the positive and negative selection marker can be the same.

Other types of selections/screening can be used in the invention for producing orthogonal translational components, e.g., a glutamyl O-tRNA, a glutamyl O-RS, and a glutamyl O-tRNA/O-RS pair. For example, the negative selection marker, the positive selection marker or both the positive and negative selection markers can include a marker that fluoresces or catalyzes a luminescent reaction in the presence of a suitable reactant. In another embodiment, a product of the marker is detected by fluorescence-activated cell sorting (FACS) or by luminescence. Optionally, the marker includes an affinity based screening marker. See Francisco, J. A., et al., (1993) *Production and fluorescence-activated cell sorting of Escherichia coli expressing a functional antibody fragment on the external surface. Proc Natl Acad Sci USA.* 90:10444-8.

Additional general methods for producing a recombinant orthogonal tRNA can be found, e.g., in International patent application WO 2002/086075, supra; and patent applications U.S. Ser. No. 60/496,548, U.S. Ser. No. 60/479,931, and U.S. Ser. No. 60/463,869, supra. See also Forster et al., (2003) *Programming peptidomimetic synthetases by translating genetic codes designed de novo PNAS* 100(11):6353-6357; and, Feng et al., (2003), *Expanding tRNA recognition of a tRNA synthetase by a single amino acid change, PNAS* 100 (10): 5676-5681.

Orthogonal Aminoacyl-tRNA Synthetase (O-RS)

A glutamyl O-RS of the invention preferentially aminoacylates a glutamyl O-tRNA with a selected amino acid in vitro or in vivo. A glutamyl O-RS of the invention can be provided to the translation system, e.g., a cell, by a polypeptide that includes a glutamyl O-RS and/or by a polynucleotide that encodes a glutamyl O-RS or a portion thereof. For example, a glutamyl O-RS, or a portion thereof, is encoded by a polynucleotide sequence as set forth in any one of SEQ ID NO.: 68, 72, 74, or 76, or a complementary polynucleotide sequence thereof. In another example, a glutamyl O-RS comprises an amino acid sequence as set forth in any one of SEQ ID NO.: SEQ ID NO.: 69, 73, 75 and/or 77, or a conservative variation thereof. See, e.g., Table 3 and Example 2, herein, for sequences of exemplary glutamyl O-RS molecules. See also, the section entitled "Nucleic Acid and Polypeptide Sequence and Variants" herein.

Methods for identifying an orthogonal glutamyl aminoacyl-tRNA synthetase (O-RS), e.g., a glutamyl O-RS, for use with a glutamyl O-tRNA, are also a feature of the invention. For example, a method includes subjecting to selection, e.g., positive selection, a population of cells of a first species, where the cells individually comprise: 1) a member of a plurality of aminoacyl-tRNA synthetases (RSs), (e.g., the plurality of RSs can include mutant RSs, RSs derived from a species other than the first species or both mutant RSs and RSs derived from a species other than the first species); 2) the orthogonal tRNA (O-tRNA) (e.g., from one or more species); and 3) a polynucleotide that encodes a (e.g., positive) selection marker and comprises at least one selector codon. Cells are selected or screened for those that show an enhancement in suppression efficiency compared to cells lacking or with a reduced amount of the member of the plurality of glutamyl RSs. Suppression efficiency can be measured by techniques known in the art and as described herein. Cells having an enhancement in suppression efficiency comprise an active glutamyl RS that aminoacylates the glutamyl O-tRNA. A level of aminoacylation (in vitro or in vivo) by the active RS of a first set of tRNAs from the first species is compared to the level of aminoacylation (in vitro or in vivo) by the active RS of a second set of tRNAs from the second species. The level of aminoacylation can be determined by a detectable substance (e.g., a labeled amino acid or unnatural amino acid). The active RS that more efficiently aminoacylates the second set of tRNAs compared to the first set of tRNAs is typically selected, thereby providing an efficient (optimized) orthogonal glutamyl aminoacyl-tRNA synthetase for use with the glutamyl O-tRNA. A glutamyl O-RS, identified by the method is also a feature of the invention.

Any of a number of assays can be used to determine aminoacylation. These assays can be performed in vitro or in vivo. For example, in vitro aminoacylation assays are described in, e.g., Hoben and Soll (1985) *Methods Enzymol.* 113:55-59. Aminoacylation can also be determined by using a reporter along with orthogonal translation components and detecting the reporter in a cell expressing a polynucleotide comprising at least one selector codon that encodes a protein. See also, International Publication No. WO 2002/085923, and, International Application Number PCT/US2004/011786.

Identified glutamyl O-RS can be further manipulated to alter the substrate specificity of the synthetase, so that only a desired unnatural amino acid, but not any of the common 20 amino acids are charged to the glutamyl O-tRNA. Methods to generate an orthogonal glutamyl aminoacyl tRNA synthetase with a substrate specificity for an unnatural amino acid include mutating the synthetase, e.g., at the active site in the synthetase, at the editing mechanism site in the synthetase, at different sites by combining different domains of synthetases, or the like, and applying a selection process. A strategy is used, which is based on the combination of a positive selection followed by a negative selection. In the positive selection, suppression of the selector codon introduced at a nonessential position(s) of a positive marker allows cells to survive under positive selection pressure. In the presence of both natural and unnatural amino acids, survivors thus encode active synthetases charging the orthogonal suppressor tRNA with either a natural or unnatural amino acid. In the negative selection, suppression of a selector codon introduced at a nonessential position(s) of a negative marker removes synthetases with natural amino acid specificities. Survivors of the negative and positive selection encode synthetases that aminoacylate (charge) the orthogonal suppressor tRNA with unnatural amino acids only. These synthetases can then be subjected to further mutagenesis, e.g., DNA shuffling or other recursive mutagenesis methods.

A library of mutant glutamyl O-RSs can be generated using various mutagenesis techniques known in the art. For example, the mutant RSs can be generated by site-specific mutations, random point mutations, homologous recombination, DNA shuffling or other recursive mutagenesis methods, chimeric construction or any combination thereof. For example, a library of mutant glutamyl RSs can be produced from two or more other, e.g., smaller, less diverse "sub-libraries." Chimeric libraries of RSs are also included in the invention. It should be noted that libraries of tRNA synthetases from various organism (e.g., microorganisms such as eubacteria or archaebacteria) such as libraries that comprise natural diversity (see, e.g., U.S. Pat. No. 6,238,884 to Short et al; U.S. Pat. No. 5,756,316 to Schallenberger et al; U.S. Pat. No. 5,783,431 to Petersen et al; U.S. Pat. No. 5,824,485 to Thompson et al; U.S. Pat. No. 5,958,672 to Short et al), are optionally constructed and screened for orthogonal pairs.

Once the synthetases are subject to the positive and negative selection/screening strategy, these synthetases can then be subjected to further mutagenesis. For example, a nucleic acid that encodes the glutamyl O-RS can be isolated; a set of polynucleotides that encode mutated glutamyl O-RSs (e.g., by random mutagenesis, site-specific mutagenesis, recombination or any combination thereof) can be generated from the nucleic acid; and, these individual steps or a combination of these steps can be repeated until a mutated glutamyl O-RS is obtained that preferentially aminoacylates the glutamyl O-tRNA with the unnatural amino acid. In one aspect of the invention, the steps are performed multiple times, e.g., at least two times.

Additional levels of selection/screening stringency can also be used in the methods of the invention, for producing glutamyl O-tRNA, glutamyl O-RS, or pairs thereof. The selection or screening stringency can be varied on one or both steps of the method to produce an O-RS. This could include, e.g., varying the amount of selection/screening agent that is used, etc. Additional rounds of positive and/or negative selections can also be performed. Selecting or screening can also comprise one or more of a change in amino acid permeability, a change in translation efficiency, a change in translational fidelity, etc. Typically, the one or more change is based upon a mutation in one or more gene in an organism in which an orthogonal tRNA-tRNA synthetase pair is used to produce protein.

Additional general information regarding generating O-RS, and altering the substrate specificity of the synthetase can be found in International Publication Number WO 2002/086075, and, International Application Number PCT/US2004/011786.

Source and Host Organisms

The translational components of the invention can be derived from non-eukaryotic organisms. For example, the glutamyl O-tRNA can be derived from a non-eukaryotic organism (or a combination of organisms), e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis,*

*Methanopyrus kandleri, Methanosarcina mazei* (Mm), *Pyrobaculum aerophilum, Pyrococcus abyssi, Sulfolobus solfataricus* (Ss), *Sulfolobus tokodaii, Thermoplasma acidophilum, Thermoplasma volcanium*, or the like, or a *eubacterium*, such as *Escherichia coli, Thermus thermophilus, Bacillus stearothermophilus*, or the like, while the glutamyl O-RS can be derived from a non-eukaryotic organism (or a combination of organisms), e.g., an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei, Pyrobaculum aerophilum, Pyrococcus abyssi, Sulfolobus solfataricus, Sulfolobus tokodaii, Thermoplasma acidophilum, Thermoplasma volcanium*, or the like, or a *eubacterium*, such as *Escherichia coli, Thermus thermophilus, Bacillus stearothermophilus*, or the like. In one embodiment, eukaryotic sources, e.g., plants, algae, protists, fungi, yeasts, animals (e.g., mammals, insects, arthropods, etc.), or the like, can also be used as sources of glutamyl O-tRNAs and glutamyl O-RSs.

The individual components of a glutamyl O-tRNA/O-RS pair can be derived from the same organism or different organisms. In one embodiment, the glutamyl O-tRNA/O-RS pair is from the same organism. Alternatively, the glutamyl O-tRNA and the glutamyl O-RS of the glutamyl O-tRNA/O-RS pair are from different organisms. For example, the glutamyl O-tRNA can be derived from, e.g., from a collection of archaeal organisms, and glutamyl O-RS can be derived from, e.g., an *Archaeoglobus fulgidus* (Af), a *Methanosarcina mazei* (Mm), a *Methanobacterium thermoautotrophicum* (Mt), a *Pyrococcus horikoshii* (Ph), etc.), a *Methanosarcina mazei* or the like.

The glutamyl O-tRNA, glutamyl O-RS or glutamyl O-tRNA/O-RS pair can be selected or screened in vivo or in vitro and/or used in a cell, e.g., a non-eukaryotic cells, or eukaryotic cells, to produce a polypeptide with a selected amino acid. A non-eukaryotic cell can be from a variety of sources, e.g., a *eubacterium*, such as *Escherichia coli, Thermus thermophilus, Bacillus stearothermophilus*, or the like, or an archaebacterium, such as *Methanococcus jannaschii, Methanobacterium thermoautotrophicum, Halobacterium* such as *Haloferax volcanii* and *Halobacterium* species NRC-1, *Archaeoglobus fulgidus, Pyrococcus furiosus, Pyrococcus horikoshii, Aeuropyrum pernix, Methanococcus maripaludis, Methanopyrus kandleri, Methanosarcina mazei* (Mm), *Pyrobaculum aerophilum, Pyrococcus abyssi, Sulfolobus solfataricus* (Ss), *Sulfolobus tokodaii, Thermoplasma acidophilum, Thermoplasma volcanium*, or the like. A eukaryotic cell can be from any of a variety of sources, e.g., a plant (e.g., complex plant such as monocots, or dicots), an algae, a protist, a fungus, a yeast (e.g., *Saccharomyces cerevisiae*), an animal (e.g., a mammal, an insect, an arthropod, etc.), or the like. Compositions of cells with translational components of the invention are also a feature of the invention.

See also, International Application Number PCT/US2004/011786 for screening O-tRNA and/or O-RS in one species for use in another species.

Selector Codons

Selector codons of the invention expand the genetic codon framework of protein biosynthetic machinery. For example, a selector codon includes, e.g., a unique three base codon, a nonsense codon, such as a stop codon, e.g., an amber codon (UAG), or an opal codon (UGA), an unnatural codon, at least a four base codon, a rare codon, or the like. A number of selector codons can be introduced into a desired gene, e.g., one or more, two or more, more than three, etc. By using different selector codons, multiple orthogonal tRNA/synthetase pairs can be used that allow the simultaneous incorporation of multiple selected amino acids, e.g., unnatural amino acids, using these different selector codons.

In one embodiment, the methods involve the use of a selector codon that is a stop codon for the incorporation of a selected amino acid in vivo in a cell. For example, a glutamyl O-tRNA is produced that recognizes the stop codon and is aminoacylated by a glutamyl O-RS with a selected amino acid. This glutamyl O-tRNA is not recognized by the naturally occurring host's aminoacyl-tRNA synthetases. Conventional site-directed mutagenesis can be used to introduce the stop codon at the site of interest in a polynucleotide encoding a polypeptide of interest. See, e.g., Sayers, J. R., et al. (1988), *5',3' Exonuclease in phosphorothioate-based oligonucleotide-directed mutagenesis. Nucleic Acids Res,* 791-802. When the glutamyl O-RS, glutamyl O-tRNA and the nucleic acid that encodes a polypeptide of interest are combined, e.g., in vivo, the selected amino acid is incorporated in response to the stop codon to give a polypeptide containing the selected amino acid at the specified position. In one embodiment of the invention, a stop codon used as a selector codon is an amber codon, UAG, and/or an opal codon, UGA. In one example, a genetic code in which UAG and UGA are both used as a selector codon can encode 22 amino acids while preserving the ochre nonsense codon, UAA, which is the most abundant termination signal.

The incorporation of selected amino acids, in vivo, can be done without significant perturbation of the host cell. For example, in non-eukaryotic cells, such as *Escherichia coli*, because the suppression efficiency for the UAG codon depends upon the competition between the O-tRNA, e.g., the amber suppressor tRNA, and the release factor 1 (RF1) (which binds to the UAG codon and initiates release of the growing peptide from the ribosome), the suppression efficiency can be modulated by, e.g., either increasing the expression level of O-tRNA, e.g., the suppressor tRNA, or using an RF1 deficient strain. In eukaryotic cells, because the suppression efficiency for the UAG codon depends upon the competition between the O-tRNA, e.g., the amber suppressor tRNA, and a eukaryotic release factor (e.g., eRF) (which binds to a stop codon and initiates release of the growing peptide from the ribosome), the suppression efficiency can be modulated by, e.g., increasing the expression level of O-tRNA, e.g., the suppressor tRNA.

Selected amino acids can also be encoded with rare codons. For example, when the arginine concentration in an in vitro protein synthesis reaction is reduced, the rare arginine codon, AGG, has proven to be efficient for insertion of Ala by a synthetic tRNA acylated with alanine. See, e.g., Ma et al., *Biochemistry,* 32:7939 (1993). In this case, the synthetic tRNA competes with the naturally occurring tRNAArg, which exists as a minor species in *Escherichia coli.* In addition, some organisms do not use all triplet codons. An unassigned codon AGA in *Micrococcus luteus* has been utilized for insertion of amino acids in an in vitro transcription/translation extract. See, e.g., Kowal and Oliver, *Nucl. Acid. Res.* 25:4685 (1997). Components of the invention can be generated to use these rare codons in vivo.

Selector codons can also comprise extended codons, e.g., four or more base codons, such as, four, five, six or more base codons. Examples of four base codons include, e.g., AGGA, CUAG, UAGA, CCCU, and the like. Examples of five base codons include, e.g., AGGAC, CCCCU, CCCUC, CUAGA, CUACU, UAGGC, and the like. Methods of the invention include using extended codons based on frameshift suppression. Four or more base codons can insert, e.g., one or multiple selected amino acids, e.g., unnatural amino acids, into the same protein. In other embodiments, the anticodon loops can decode, e.g., at least a four-base codon, at least a five-base codon, or at least a six-base codon or more. Since there are 256 possible four-base codons, multiple unnatural amino acids can be encoded in the same cell using a four or more base codon. See also, Anderson et al., (2002) *Exploring the Limits of Codon and Anticodon Size, Chemistry and Biology,* 9:237-244; and, Magliery, (2001) *Expanding the Genetic Code: Selection of Efficient Suppressors of Four-base Codons and Identification of "Shifty" Four-base Codons with a Library Approach in Escherichia coli, J. Mol. Biol.* 307: 755-769.

For example, four-base codons have been used to incorporate unnatural amino acids into proteins using in vitro biosynthetic methods. See, e.g., Ma et al., (1993) *Biochemistry,* 32:7939; and Hohsaka et al., (1999) *J. Am. Chem. Soc.* 121: 34. CGGG and AGGU were used to simultaneously incorporate 2-naphthylalanine and an NBD derivative of lysine into streptavidin in vitro with two chemically acylated frameshift suppressor tRNAs. See, e.g., Hohsaka et al., (1999) *J. Am. Chem. Soc.,* 121:12194. In an in vivo study, Moore et al. examined the ability of $tRNA^{Leu}$ derivatives with NCUA anticodons to suppress UAGN codons (N can be U, A, G, or C), and found that the quadruplet UAGA can be decoded by a $tRNA^{Leu}$ with a UCUA anticodon with an efficiency of 13 to 26% with little decoding in the 0 or −1 frame. See Moore et al., (2000) *J. Mol. Biol.* 298:195. In one embodiment, extended codons based on rare codons or nonsense codons can be used in invention, which can reduce missense readthrough and frameshift suppression at other unwanted sites.

For a given system, a selector codon can also include one of the natural three base codons, where the endogenous system does not use (or rarely uses) the natural base codon. For example, this includes a system that is lacking a tRNA that recognizes the natural three base codon, and/or a system where the three base codon is a rare codon.

Selector codons optionally include unnatural base pairs. These unnatural base pairs further expand the existing genetic alphabet. One extra base pair increases the number of triplet codons from 64 to 125. Properties of third base pairs include stable and selective base pairing, efficient enzymatic incorporation into DNA with high fidelity by a polymerase, and the efficient continued primer extension after synthesis of the nascent unnatural base pair. Descriptions of unnatural base pairs which can be adapted for methods and compositions include, e.g., Hirao, et al., (2002) *An unnatural base pair for incorporating amino acid analogues into protein, Nature Biotechnology,* 20:177-182. See also Wu, Y., et al., (2002) *J. Am. Chem. Soc.* 124:14626-14630. Other relevant publications are listed below.

For in vivo usage, the unnatural nucleoside is membrane permeable and is phosphorylated to form the corresponding triphosphate. In addition, the increased genetic information is stable and not destroyed by cellular enzymes. Previous efforts by Benner and others took advantage of hydrogen bonding patterns that are different from those in canonical Watson-Crick pairs, the most noteworthy example of which is the iso-C:iso-G pair. See, e.g., Switzer et al., (1989) *J. Am. Chem. Soc.,* 111:8322; and Piccirilli et al., (1990) *Nature,* 343:33; Kool, (2000) *Curr. Opin. Chem. Biol.* 4:602. These bases in general mispair to some degree with natural bases and cannot be enzymatically replicated. Kool and co-workers demonstrated that hydrophobic packing interactions between bases can replace hydrogen bonding to drive the formation of base pair. See Kool, (2000) *Curr. Opin. Chem. Biol.* 4:602; and Guckian and Kool, (1998) *Angew. Chem. Int. Ed. Engl.,* 36, 2825. In an effort to develop an unnatural base pair satisfying all the above requirements, Schultz, Romesberg and co-workers have systematically synthesized and studied a series of unnatural hydrophobic bases. A PICS:PICS self-pair is found to be more stable than natural base pairs, and can be efficiently incorporated into DNA by Klenow fragment of *Escherichia coli* DNA polymerase I (KF). See, e.g., McMinn et al., (1999) *J. Am. Chem. Soc.* 121:11586; and Ogawa et al., (2000) *J. Am. Chem. Soc.,* 122:3274. A 3MN:3MN self-pair can be synthesized by KF with efficiency and selectivity sufficient for biological function. See, e.g., Ogawa et al., (2000) *J. Am. Chem. Soc.* 122:8803. However, both bases act as a chain terminator for further replication. A mutant DNA polymerase has been recently evolved that can be used to replicate the PICS self pair. In addition, a 7AI self pair can be replicated. See, e.g., Tae et al., (2001) *J. Am. Chem. Soc.,* 123:7439. A novel metallobase pair, Dipic:Py, has also been developed, which forms a stable pair upon binding Cu(II). See Meggers et al., (2000) *J. Am. Chem. Soc.* 122:10714. Because extended codons and unnatural codons are intrinsically orthogonal to natural codons, the methods of the invention can take advantage of this property to generate orthogonal tRNAs for them.

A translational bypassing system can also be used to incorporate a selected amino acid in a desired polypeptide. In a translational bypassing system, a large sequence is inserted into a gene but is not translated into protein. The sequence contains a structure that serves as a cue to induce the ribosome to hop over the sequence and resume translation downstream of the insertion.

Selected Amino Acids

As used herein, a selected amino acid refers to any desired naturally occurring amino acid or unnatural amino acid. A naturally occurring amino acid includes any one of the twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. In one embodiment, the selected amino acid is incorporated into a growing polypeptide chain with high fidelity, e.g., at greater than 75% efficiency for a given selector codon, at greater than about 80% efficiency for a given selector codon, at greater than about 90% efficiency for a given selector codon, at greater than about 95% efficiency for a given selector codon, or at greater than about 99% or more efficiency for a given selector codon.

As used herein, an unnatural amino acid refers to any amino acid, modified amino acid, or amino acid analogue other than selenocysteine and/or pyrrolysine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

I

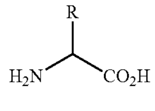

An unnatural amino acid is typically any structure having Formula I wherein the R group is any substituent other than one used in the twenty natural amino acids. See e.g., *Biochemistry* by L. Stryer, 3rd ed. 1988, Freeman and Company, New York, for structures of the twenty natural amino acids. Note that, the unnatural amino acids of the invention can be naturally occurring compounds other than the twenty alpha-amino acids above.

Because the unnatural amino acids of the invention typically differ from the natural amino acids in side chain, the unnatural amino acids form amide bonds with other amino acids, e.g., natural or unnatural, in the same manner in which they are formed in naturally occurring proteins. However, the unnatural amino acids have side chain groups that distinguish them from the natural amino acids. For example, R in Formula I optionally comprises an alkyl-, aryl-, acyl-, keto-, azido-, hydroxyl-, hydrazine, cyano-, halo-, hydrazide, alkenyl, alkynyl, ether, thiol, seleno-, sulfonyl-, borate, boronate, phospho, phosphono, phosphine, heterocyclic, enone, imine, aldehyde, ester, thioacid, hydroxylamine, amine, and the like, or any combination thereof. Other unnatural amino acids of interest include, but are not limited to, amino acids comprising a photoactivatable cross-linker, spin-labeled amino acids, fluorescent amino acids, metal binding amino acids, metal-containing amino acids, radioactive amino acids, amino acids with novel functional groups, amino acids that covalently or noncovalently interact with other molecules, photocaged and/or photoisomerizable amino acids, biotin or biotin-analogue containing amino acids, keto containing amino acids, amino acids comprising polyethylene glycol or polyether, heavy atom substituted amino acids, chemically cleavable or photocleavable amino acids, amino acids with an elongated side chain as compared to natural amino acids (e.g., polyethers or long chain hydrocarbons, e.g., greater than about 5, greater than about 10 carbons, etc.), carbon-linked sugar-containing amino acids, amino thioacid containing amino acids, and amino acids containing one or more toxic moiety. In some embodiments, the unnatural amino acids have a photoactivatable cross-linker that is used, e.g., to link a protein to a solid support. In one embodiment, the unnatural amino acids have a saccharide moiety attached to the amino acid side chain (e.g., glycosylated amino acids) and/or other carbohydrate modification.

In addition to unnatural amino acids that contain novel side chains, unnatural amino acids also optionally comprise modified backbone structures, e.g., as illustrated by the structures of Formula II and III:

II

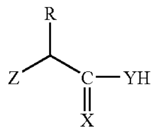

III

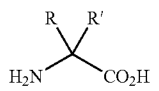

wherein Z typically comprises OH, $NH_2$, SH, NH—R', or S—R'; X and Y, which can be the same or different, typically comprise S or O, and R and R', which are optionally the same or different, are typically selected from the same list of constituents for the R group described above for the unnatural amino acids having Formula I as well as hydrogen. For example, unnatural amino acids of the invention optionally comprise substitutions in the amino or carboxyl group as illustrated by Formulas II and III. Unnatural amino acids of this type include, but are not limited to, α-hydroxy acids, α-thioacids α-aminothiocarboxylates, e.g., with side chains corresponding to the common twenty natural amino acids or unnatural side chains. In addition, substitutions at the α-carbon optionally include L, D, or α-α-disubstituted amino acids such as D-glutamate, D-alanine, D-methyl-O-tyrosine, aminobutyric acid, and the like. Other structural alternatives include cyclic amino acids, such as proline analogues as well as 3, 4, 6, 7, 8, and 9 membered ring proline analogues, β and γ amino acids such as substituted β-alanine and γ-amino butyric acid. Additional unnatural amino acid structures of the invention include homo-beta-type structures, e.g., where there is, e.g., a methylene or amino group sandwiched adjacent to the alpha carbon, e.g., isomers of homo-beta-tyrosine, alpha-hydrazino-tyrosine. See, e.g.,

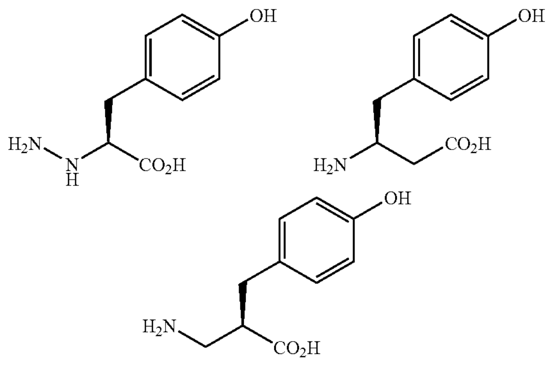

Many unnatural amino acids are based on natural amino acids, such as glutamine, tyrosine, phenylalanine, and the like. For example, glutamine analogs of the invention include, but are not limited to, α-hydroxy derivatives, γ-substituted derivatives, cyclic derivatives, and amide substituted glutamine derivatives. Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a $C_6$-$C_{20}$ straight chain or branched hydrocarbon, a saturated or unsaturated hydrocarbon, an O-methyl group, a polyether group, a nitro group, or the like. In addition, multiply substituted aryl rings are also contemplated. Example phenylalanine analogs include, but are not limited to, para-substituted phenylalanines, ortho-substituted phenyalanines, and meta-substituted phenylalanines, wherein the substituent comprises a hydroxy group, a methoxy group, a methyl group, an allyl group, an aldehyde or keto group, or the like. Specific examples of unnatural amino acids include, but are not limited to, a p-acetyl-L-phenylalanine, a p-propargyloxyphenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAcβ-serine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodophenylalanine, a p-bromophenylalanine, a p-amino-L-phenylalanine, and an isopropyl-L-phenylalanine, and the like. The structures of a variety of unnatural amino acids are provided in, for example, FIGS. 16, 17, 18, 19, 26, and 29 of WO 2002/085923, supra.

Chemical Synthesis of Unnatural Amino Acids

Many of the unnatural amino acids provided above are commercially available, e.g., from Sigma (USA) or Aldrich (Milwaukee, Wis., USA). Those that are not commercially available are optionally synthesized as provided in various publications or using standard methods known to those of skill in the art. For organic synthesis techniques, see, e.g., *Organic Chemistry* by Fessendon and Fessendon, (1982, Second Edition, Willard Grant Press, Boston Mass.); *Advanced Organic Chemistry* by March (Third Edition, 1985, Wiley and Sons, New York); and *Advanced Organic Chemistry* by Carey and Sundberg (Third Edition, Parts A and B, 1990, Plenum Press, New York). Additional publications describing the synthesis of unnatural amino acids include, e.g., WO 2002/085923, supra; Matsoukas et al., (1995) *J. Med. Chem.* 38, 4660-4669; King, F. E. & Kidd, D. A. A. (1949) *A New Synthesis of Glutamine and of γ-Dipeptides of Glutamic Acid from Phthylated Intermediates. J. Chem. Soc.,* 3315-3319; Friedman, O. M. & Chatterrji, R. (1959) *Synthesis of Derivatives of Glutamine as Model Substrates for Anti-Tumor Agents. J. Am. Chem. Soc.* 81, 3750-3752; Craig, J. C. et al. (1988) *Absolute Configuration of the Enantiomers of* 7-*Choro*-4[[4-(*diethylamino*)-1-*methylbutyl*]*amino*]*quinioline* (*Chloroquine*). *J. Org. Chem.* 53, 1167-1170; Azoulay, M., Vilmont, M. & Frappier, F. (1991) *Glutamine analogues as Potential Antimalarials, Eur. J. Med. Chem.* 26, 201-5; Koskinen, A. M. P. & Rapoport, H. (1989) *Synthesis of* 4-*Substituted Prolines as Conformationally Constrained Amino Acid Analogues. J. Org. Chem.* 54, 1859-1866; Christie, B. D. & Rapoport, H. (1985) *Synthesis of Optically Pure Pipecolates from L-Asparagine. Application to the Total Synthesis of* (+)-*Apovincamine through Amino Acid Decarbonylation and Iminium Ion Cyclization. J. Org. Chem.* 1989:1859-1866; Barton et al., (1987) *Synthesis of Novel a-Amino-Acids and Derivatives Using Radical Chemistry: Synthesis of L- and D-α-Amino-Adipic Acids, L-α-aminopimelic Acid and Appropriate Unsaturated Derivatives. Tetrahedron Lett.* 43:4297-4308; and, Subasinghe et al., (1992) *Quisqualic acid analogues: synthesis of beta-heterocyclic* 2-*aminopropanoic acid derivatives and their activity at a novel quisqualate-sensitized site. J. Med. Chem.* 35:4602-7. See also, International Application Number PCT/US03/41346, entitled "Protein Arrays," filed on Dec. 22, 2003.

Cellular Uptake of Unnatural Amino Acids

Unnatural amino acid uptake by a cell is one issue that is typically considered when designing and selecting unnatural amino acids, e.g., for incorporation into a protein. For example, the high charge density of α-amino acids suggests that these compounds are unlikely to be cell permeable. Natural amino acids are taken up into the cell via a collection of protein-based transport systems often displaying varying degrees of amino acid specificity. A rapid screen can be done which assesses which unnatural amino acids, if any, are taken up by cells. See, e.g., International Application Number PCT/US03/41346, entitled "Protein Arrays," filed on Dec. 22, 2003; and Liu, D. R. & Schultz, P. G. (1999) *Progress toward the evolution of an organism with an expanded genetic code. PNAS United States* 96:4780-4785. Although uptake is easily analyzed with various assays, an alternative to designing unnatural amino acids that are amenable to cellular uptake pathways is to provide biosynthetic pathways to create amino acids in vivo.

Biosynthesis of Unnatural Amino Acids

Many biosynthetic pathways already exist in cells for the production of amino acids and other compounds. While a biosynthetic method for a particular unnatural amino acid may not exist in nature, e.g., in a cell, the invention provides such methods. For example, biosynthetic pathways for unnatural amino acids are optionally generated in a host cell by adding new enzymes or modifying existing host cell pathways. Additional new enzymes are optionally naturally occurring enzymes or artificially evolved enzymes. For example, the biosynthesis of p-aminophenylalanine (as presented in an example in WO 2002/085923, supra) relies on the addition of a combination of known enzymes from other organisms. The genes for these enzymes can be introduced into a cell by transforming the cell with a plasmid comprising the genes. The genes, when expressed in the cell, provide an enzymatic pathway to synthesize the desired compound. Examples of the types of enzymes that are optionally added are provided in the examples below. Additional enzyme sequences are found, e.g., in Genbank. Artificially evolved enzymes are also optionally added into a cell in the same manner. In this manner, the cellular machinery and resources of a cell are manipulated to produce unnatural amino acids.

Indeed, any of a variety of methods can be used for producing novel enzymes for use in biosynthetic pathways, or for evolution of existing pathways, for the production of unnatural amino acids, in vitro or in vivo. Many available methods of evolving enzymes and other biosynthetic pathway components can be applied to the present invention to produce unnatural amino acids (or, indeed, to evolve synthetases to have new substrate specificities or other activities of interest). For example, DNA shuffling is optionally used to develop novel enzymes and/or pathways of such enzymes for the production of unnatural amino acids (or production of new synthetases), in vitro or in vivo. See, e.g., Stemmer (1994), *Rapid evolution of a protein in vitro by DNA shuffling, Nature* 370(4):389-391; and, Stemmer, (1994), *DNA shuffling by random fragmentation and reassembly: In vitro recombination for molecular evolution, Proc. Natl. Acad. Sci. USA.,* 91:10747-10751. A related approach shuffles families of related (e.g., homologous) genes to quickly evolve enzymes with desired characteristics. An example of such "family gene shuffling" methods is found in Crameri et al. (1998) "DNA shuffling of a family of genes from diverse species accelerates directed evolution" *Nature,* 391(6664): 288-291. New enzymes (whether biosynthetic pathway components or synthetases) can also be generated using a DNA recombination procedure known as "incremental truncation for the creation of hybrid enzymes" ("ITCHY"), e.g., as described in Ostermeier et al. (1999) "A combinatorial approach to hybrid enzymes independent of DNA homology" *Nature Biotech* 17:1205. This approach can also be used to generate a library of enzyme or other pathway variants which can serve as substrates for one or more in vitro or in vivo recombination methods. See also, Ostermeier et al. (1999) "Combinatorial Protein Engineering by Incremental Truncation," *Proc. Natl. Acad. Sci. USA,* 96: 3562-67, and Ostermeier et al. (1999), "Incremental Truncation as a Strategy in the Engineering of Novel Biocatalysts," *Biological and Medicinal Chemistry,* 7: 2139-44. Another approach uses exponential ensemble mutagenesis to produce libraries of enzyme or other pathway variants that are, e.g., selected for an ability to catalyze a biosynthetic reaction relevant to producing an unnatural amino acid (or a new synthetase). In this approach, small groups of residues in a sequence of interest are randomized in parallel to identify, at each altered position, amino acids which lead to functional proteins. Examples of such procedures, which can be adapted to the present invention to produce new enzymes for the production of unnatural amino acids (or new synthetases) are found in Delegrave & Youvan (1993) *Biotechnology Research* 11:1548-1552. In yet another approach, random or semi-random mutagenesis using doped or degenerate oligonucleotides for enzyme and/or pathway component engineering can be used, e.g., by using the general mutagenesis methods of e.g., Arkin and Youvan (1992) "Optimizing nucleotide mixtures to encode specific subsets of amino acids for semi-random mutagenesis" *Biotechnology* 10:297-300; or Reidhaar-Olson et al. (1991) "Random mutagenesis of protein sequences using oligonucleotide cassettes" *Methods Enzymol.* 208:564-86. Yet another approach, often termed a "non-stochastic" mutagenesis, which uses polynucleotide reassembly and site-saturation mutagenesis can be used to produce enzymes and/or pathway components, which can then be screened for an ability to perform one or more synthetase or biosynthetic pathway function (e.g., for the production of unnatural amino acids in vivo). See, e.g., Short "Non-Stochastic Generation of Genetic Vaccines and Enzymes" WO 00/46344.

An alternative to such mutational methods involves recombining entire genomes of organisms and selecting resulting progeny for particular pathway functions (often referred to as "whole genome shuffling"). This approach can be applied to the present invention, e.g., by genomic recombination and selection of an organism (e.g., an *E. coli* or other cell) for an ability to produce an unnatural amino acid (or intermediate thereof). For example, methods taught in the following publications can be applied to pathway design for the evolution of existing and/or new pathways in cells to produce unnatural amino acids in vivo: Patnaik et al. (2002) "Genome shuffling of *lactobacillus* for improved acid tolerance" *Nature Biotechnology,* 20(7): 707-712; and Zhang et al. (2002) "Genome shuffling leads to rapid phenotypic improvement in bacteria" Nature, February 7, 415(6872): 644-646.

Other techniques for organism and metabolic pathway engineering, e.g., for the production of desired compounds are also available and can also be applied to the production of unnatural amino acids. Examples of publications teaching useful pathway engineering approaches include: Nakamura and White (2003) "Metabolic engineering for the microbial production of 1,3propanediol" *Curr. Opin. Biotechnol.* 14(5): 454-9; Berry et al. (2002) "Application of Metabolic Engineering to improve both the production and use of Biotech Indigo" *J. Industrial Microbiology and Biotechnology* 28:127-133; Banta et al. (2002) "Optimizing an artificial metabolic pathway: Engineering the cofactor specificity of *Corynebacterium* 2,5-diketo-D-gluconic acid reductase for use in vitamin C biosynthesis" *Biochemistry,* 41(20), 6226-36; Selivonova et al. (2001) "Rapid Evolution of Novel Traits in Microorganisms" *Applied and Environmental Microbiology,* 67:3645, and many others.

Regardless of the method used, typically, the unnatural amino acid produced with an engineered biosynthetic pathway of the invention is produced in a concentration sufficient for efficient protein biosynthesis, e.g., a natural cellular amount, but not to such a degree as to significantly affect the concentration of other cellular amino acids or to exhaust cellular resources. Typical concentrations produced in vivo in this manner are about 10 mM to about 0.05 mM. Once a cell is engineered to produce enzymes desired for a specific pathway and an unnatural amino acid is generated, in vivo selections are optionally used to further optimize the production of the unnatural amino acid for both ribosomal protein synthesis and cell growth.

Nucleic Acid and Polypeptide Sequence and Variants

As described above and below, the invention provides for nucleic acid polynucleotide sequences, e.g., glutamyl O-tRNAs and glutamyl O-RSs, and polypeptide amino acid sequences, e.g., glutamyl O-RSs, and, e.g., compositions, systems and methods comprising said sequences. Examples of said sequences, e.g., glutamyl O-tRNAs and glutamyl O-RSs are disclosed herein (see, e.g., SEQ ID NO. 67, 68, 72, 74, 76, 69, 73, 75 and/or 77, along with others listed in Table 3 herein). However, one of skill in the art will appreciate that the invention is not limited to those sequences disclosed herein, e.g., as in the Examples. One of skill will appreciate that the invention also provides many related and even unrelated sequences with the functions described herein, e.g., encoding a glutamyl O-tRNA or a glutamyl O-RS.

The invention provides polypeptides (glutamyl O-RSs) and polynucleotides, e.g., glutamyl O-tRNA, polynucleotides that encode glutamyl O-RSs or portions thereof, oligonucleotides used to isolate aminoacyl-tRNA synthetase clones, etc. Polynucleotides of the invention include those that encode proteins or polypeptides of interest of the invention with one or more selector codon. In addition, polynucleotides of the invention include, e.g., a polynucleotide comprising a nucleotide sequence comprising SEQ ID NO.: 67; a polynucleotide that is complementary to or that encodes a polynucleotide sequence thereof. A polynucleotide of the invention also includes a polynucleotide that encodes a polypeptide of the invention. Similarly, an artificial nucleic acid that hybridizes to a polynucleotide indicated above under highly stringent conditions over substantially the entire length of the nucleic acid (and is other than a naturally polynucleotide) is a polynucleotide of the invention. In one embodiment, a composition includes a polypeptide of the invention and an excipient (e.g., buffer, water, pharmaceutically acceptable excipient, etc.).

The invention also provides an antibody or antisera specifically immunoreactive with a polypeptide of the invention. A polynucleotide of the invention also includes an artificial polynucleotide that is, e.g., at least 75%, at least 80%, at least 90%, at least 95%, at least 98% or more identical to that of a naturally occurring glutamyl tRNA, (but is other than a naturally occurring glutamyl tRNA. An artificial polynucleotide or polypeptide is a polynucleotide or a polypeptide that is man made (e.g., via recombinant expression or chemical synthesis) and is not naturally occurring.

In certain embodiments, a vector (e.g., a plasmid, a cosmid, a phage, a virus, etc.) comprises a polynucleotide of the invention. In one embodiment, the vector is an expression vector. In another embodiment, the expression vector includes a promoter operably linked to one or more of the polynucleotides of the invention. In another embodiment, a cell comprises a vector that includes a polynucleotide of the invention.

One of skill will also appreciate that many variants of the disclosed sequences are included in the invention. For example, conservative variations of the disclosed sequences that yield a functionally identical sequence are included in the invention. Variants of the nucleic acid polynucleotide sequences, wherein the variants hybridize to at least one disclosed sequence, are considered to be included in the invention. Unique subsequences of the sequences disclosed herein, as determined by, e.g., standard sequence comparison techniques, are also included in the invention.

Conservative Variations

Owing to the degeneracy of the genetic code, "silent substitutions" (i.e., substitutions in a nucleic acid sequence which do not result in an alteration in an encoded polypeptide) are an implied feature of every nucleic acid sequence which encodes an amino acid. Similarly, "conservative amino acid substitutions," in one or a few amino acids in an amino acid sequence are substituted with different amino acids with highly similar properties, are also readily identified as being highly similar to a disclosed construct. Such conservative variations of each disclosed sequence are a feature of the present invention.

"Conservative variations" of a particular nucleic acid sequence refers to those nucleic acids which encode identical or essentially identical amino acid sequences, or, where the nucleic acid does not encode an amino acid sequence, to essentially identical sequences. One of skill will recognize that individual substitutions, deletions or additions which alter, add or delete a single amino acid or a small percentage of amino acids (typically less than 5%, more typically less than 4%, 2% or 1%) in an encoded sequence are "conservatively modified variations" where the alterations result in the deletion of an amino acid, addition of an amino acid, or substitution of an amino acid with a chemically similar amino acid. Thus, "conservative variations" of a listed polypeptide sequence of the present invention include substitutions of a small percentage, typically less than 5%, more typically less than 2% or 1%, of the amino acids of the polypeptide sequence, with a conservatively selected amino acid of the same conservative substitution group. Finally, the addition of sequences which do not alter the encoded activity of a nucleic acid molecule, such as the addition of a non-functional sequence, is a conservative variation of the basic nucleic acid.

Conservative substitution tables providing functionally similar amino acids are well known in the art. The following sets forth example groups which contain natural amino acids that include "conservative substitutions" for one another.

Conservative Substitution Groups

| Nonpolar and/or Aliphatic Side Chains | Polar, Uncharged Side Chains | Aromatic Side Chains | Positively Charged Side Chains | Negatively Charged Side Chains |
|---|---|---|---|---|
| Glycine | Serine | Phenylalanine | Lysine | Aspartate |
| Alanine | Threonine | Tyrosine | Arginine | Glutamate |
| Valine | Cysteine | Tryptophan | Histidine | |
| Leucine | Methionine | | | |
| Isoleucine | Asparagine | | | |
| Proline | Glutamine | | | |

Nucleic Acid Hybridization

Comparative hybridization can be used to identify nucleic acids of the invention, such as SEQ ID NO.: 67, including conservative variations of nucleic acids of the invention, and this comparative hybridization method is a preferred method of distinguishing nucleic acids of the invention. In addition, target nucleic acids which hybridize to a nucleic acid represented by SEQ ID NO: 67 under high, ultra-high and ultra-ultra high stringency conditions are a feature of the invention. Examples of such nucleic acids include those with one or a few silent or conservative nucleic acid substitutions as compared to a given nucleic acid sequence.

A test nucleic acid is said to specifically hybridize to a probe nucleic acid when it hybridizes at least ½ as well to the probe as to the perfectly matched complementary target, i.e., with a signal to noise ratio at least ½ as high as hybridization of the probe to the target under conditions in which the perfectly matched probe binds to the perfectly matched complementary target with a signal to noise ratio that is at least about 5×-10× as high as that observed for hybridization to any of the unmatched target nucleic acids.

Nucleic acids "hybridize" when they associate, typically in solution. Nucleic acids hybridize due to a variety of well characterized physico-chemical forces, such as hydrogen bonding, solvent exclusion, base stacking and the like. An extensive guide to the hybridization of nucleic acids is found in Tijssen (1993) *Laboratory Techniques in Biochemistry and Molecular Biology—Hybridization with Nucleic Acid Probes* part I chapter 2, "Overview of principles of hybridization and the strategy of nucleic acid probe assays," (Elsevier, N.Y.), as well as in Ausubel, supra. Hames and Higgins (1995) *Gene Probes* 1 IRL Press at Oxford University Press, Oxford, England, (Hames and Higgins 1) and Hames and Higgins (1995) *Gene Probes* 2 IRL Press at Oxford University Press, Oxford, England (Hames and Higgins 2) provide details on the synthesis, labeling, detection and quantification of DNA and RNA, including oligonucleotides.

An example of stringent hybridization conditions for hybridization of complementary nucleic acids which have more than 100 complementary residues on a filter in a Southern or northern blot is 50% formalin with 1 mg of heparin at 42° C., with the hybridization being carried out overnight. An example of stringent wash conditions is a 0.2×SSC wash at 65° C. for 15 minutes (see, Sambrook, supra for a description of SSC buffer). Often the high stringency wash is preceded by a low stringency wash to remove background probe signal. An example low stringency wash is 2×SSC at 40° C. for 15 minutes. In general, a signal to noise ratio of 5× (or higher) than that observed for an unrelated probe in the particular hybridization assay indicates detection of a specific hybridization.

"Stringent hybridization wash conditions" in the context of nucleic acid hybridization experiments such as Southern and northern hybridizations are sequence dependent, and are different under different environmental parameters. An extensive guide to the hybridization of nucleic acids is found in Tijssen (1993), supra. and in Hames and Higgins, 1 and 2. Stringent hybridization and wash conditions can easily be determined empirically for any test nucleic acid. For example, in determining stringent hybridization and wash conditions, the hybridization and wash conditions are gradually increased (e.g., by increasing temperature, decreasing salt concentration, increasing detergent concentration and/or increasing the concentration of organic solvents such as formalin in the hybridization or wash), until a selected set of criteria are met. For example, in highly stringent hybridization and wash conditions, the hybridization and wash conditions are gradually increased until a probe binds to a perfectly matched complementary target with a signal to noise ratio that is at least 5× as high as that observed for hybridization of the probe to an unmatched target.

"Very stringent" conditions are selected to be equal to the thermal melting point ($T_m$) for a particular probe. The $T_m$ is the temperature (under defined ionic strength and pH) at which 50% of the test sequence hybridizes to a perfectly matched probe. For the purposes of the present invention, generally, "highly stringent" hybridization and wash conditions are selected to be about 5° C. lower than the $T_m$ for the specific sequence at a defined ionic strength and pH.

"Ultra high-stringency" hybridization and wash conditions are those in which the stringency of hybridization and wash conditions are increased until the signal to noise ratio for binding of the probe to the perfectly matched complementary target nucleic acid is at least 10× as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-high stringency conditions.

Similarly, even higher levels of stringency can be determined by gradually increasing the hybridization and/or wash conditions of the relevant hybridization assay. For example, those in which the stringency of hybridization and wash conditions are increased until the signal to noise ratio for binding of the probe to the perfectly matched complementary target nucleic acid is at least 10×, 20×, 50×, 100×, or 500× or more as high as that observed for hybridization to any of the unmatched target nucleic acids. A target nucleic acid which hybridizes to a probe under such conditions, with a signal to noise ratio of at least ½ that of the perfectly matched complementary target nucleic acid is said to bind to the probe under ultra-ultra-high stringency conditions.

Nucleic acids which do not hybridize to each other under stringent conditions are still substantially identical if the polypeptides which they encode are substantially identical. This occurs, e.g., when a copy of a nucleic acid is created using the maximum codon degeneracy permitted by the genetic code.

Unique Subsequences

In one aspect, the invention provides a nucleic acid that comprises a unique subsequence in a nucleic acid selected from the sequences of glutamyl O-tRNAs and glutamyl O-RSs disclosed herein. The unique subsequence is unique as compared to a nucleic acid corresponding to any known glutamyl O-tRNA or glutamyl O-RS nucleic acid sequence. Alignment can be performed using, e.g., BLAST set to default parameters. Any unique subsequence is useful, e.g., as a probe to identify the nucleic acids of the invention.

Similarly, the invention includes a polypeptide which comprises a unique subsequence in a polypeptide selected from the sequences of glutamyl O-RSs disclosed herein. Here, the unique subsequence is unique as compared to a polypeptide corresponding to any of known polypeptide sequence.

The invention also provides for target nucleic acids which hybridizes under stringent conditions to a unique coding oligonucleotide which encodes a unique subsequence in a polypeptide selected from the sequences of glutamyl O-RSs wherein the unique subsequence is unique as compared to a polypeptide corresponding to any of the control polypeptides (e.g., parental sequences from which synthetases of the invention were derived, e.g., by mutation). Unique sequences are determined as noted above.

Sequence Comparison, Identity, and Homology

The terms "identical" or percent "identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the sequence comparison algorithms described below (or other algorithms available to persons of skill) or by visual inspection.

The phrase "substantially identical," in the context of two nucleic acids or polypeptides (e.g., DNAs encoding an glutamyl O-tRNA or glutamyl O-RS, or the amino acid sequence of an O-RS) refers to two or more sequences or subsequences that have at least about 60%, about 80%, about 90-95%, about 98%, about 99% or more nucleotide or amino acid residue identity, when compared and aligned for maximum correspondence, as measured using a sequence comparison algorithm or by visual inspection. Such "substantially identical" sequences are typically considered to be "homologous," without reference to actual ancestry. Preferably, the "substantial identity" exists over a region of the sequences that is at least about 50 residues in length, more preferably over a region of at least about 100 residues, and most preferably, the sequences are substantially identical over at least about 150 residues, or over the full length of the two sequences to be compared.

Proteins and/or protein sequences are "homologous" when they are derived, naturally or artificially, from a common ancestral protein or protein sequence. Similarly, nucleic acids and/or nucleic acid sequences are homologous when they are derived, naturally or artificially, from a common ancestral nucleic acid or nucleic acid sequence. For example, any naturally occurring nucleic acid can be modified by any available mutagenesis method to include one or more selector codon. When expressed, this mutagenized nucleic acid encodes a polypeptide comprising one or more selected amino acid, e.g. unnatural amino acid. The mutation process can, of course, additionally alter one or more standard codon, thereby changing one or more standard amino acid in the resulting mutant protein as well. Homology is generally inferred from sequence similarity between two or more nucleic acids or proteins (or sequences thereof). The precise percentage of similarity between sequences that is useful in establishing homology varies with the nucleic acid and protein at issue, but as little as 25% sequence similarity is routinely used to establish homology. Higher levels of sequence similarity, e.g., 30%, 40%, 50%, 60%, 70%, 80%, 90%, 95%, or 99% or more, can also be used to establish homology. Methods for determining sequence similarity percentages (e.g., BLASTP and BLASTN using default parameters) are described herein and are generally available.

For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, W. Va.), or by visual inspection (see generally Ausubel et al., infra).

One example of an algorithm that is suitable for determining percent sequence identity and sequence similarity is the BLAST algorithm, which is described in Altschul et al., *J. Mol. Biol.* 215:403-410 (1990). Software for performing BLAST analyses is publicly available through the National Center for Biotechnology Information (www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Mutagenesis and Other Molecular Biology Techniques

Polynucleotide and polypeptides of the invention and used in the invention can be manipulated using molecular biological techniques. General texts which describe molecular biological techniques include Berger and Kimmel, *Guide to Molecular Cloning Techniques, Methods in Enzymology volume* 152 Academic Press, Inc., San Diego, Calif. (Berger); Sambrook et al., *Molecular Cloning—A Laboratory Manual* (*3rd Ed.*). Vol. 1-3, Cold Spring Harbor Laboratory, Cold Spring Harbor, N.Y., 2001 ("Sambrook") and *Current Protocols in Molecular Biology*, F. M. Ausubel et al., eds., *Current Protocols*, a joint venture between Greene Publishing Associates, Inc. and John Wiley & Sons, Inc., (supplemented through 2003) ("Ausubel")). These texts describe mutagenesis, the use of vectors, promoters and many other relevant topics related to, e.g., the generation of genes that include selector codons for production of proteins that include selected amino acids (e.g., unnatural amino acids), glutamyl orthogonal tRNAs, glutamyl orthogonal synthetases, and pairs thereof.

Various types of mutagenesis are used in the invention, e.g., to mutate glutamyl tRNA molecules, to produce libraries of glutamyl tRNAs, to produce libraries of glutamyl synthetases, to insert selector codons that encode a selected amino acid in a protein or polypeptide of interest. They include but are not limited to site-directed, random point mutagenesis, homologous recombination, DNA shuffling or other recursive mutagenesis methods, chimeric construction, mutagenesis using uracil containing templates, oligonucleotide-directed mutagenesis, phosphorothioate-modified DNA mutagenesis, mutagenesis using gapped duplex DNA or the like, or any combination thereof. Additional suitable methods include point mismatch repair, mutagenesis using repair-deficient host strains, restriction-selection and restriction-purification, deletion mutagenesis, mutagenesis by total gene synthesis, double-strand break repair, and the like. Mutagenesis, e.g., involving chimeric constructs, is also included in the invention. In one embodiment, mutagenesis can be guided by known information of the naturally occurring molecule or altered or mutated naturally occurring molecule, e.g., sequence, sequence comparisons, physical properties, crystal structure or the like.

Host cells are genetically engineered (e.g., transformed, transduced or transfected) with the polynucleotides of the invention or constructs which include a polynucleotide of the invention, e.g., a vector of the invention, which can be, for example, a cloning vector or an expression vector. For example, the coding regions for the orthogonal tRNA, the orthogonal tRNA synthetase, and the protein to be derivatized are operably linked to gene expression control elements that are functional in the desired host cell. Typical vectors contain transcription and translation terminators, transcription and translation initiation sequences, and promoters useful for regulation of the expression of the particular target nucleic acid. The vectors optionally comprise generic expression cassettes containing at least one independent terminator sequence, sequences permitting replication of the cassette in eukaryotes, or prokaryotes, or both (e.g., shuttle vectors) and selection markers for both prokaryotic and eukaryotic systems. Vectors are suitable for replication and/or integration in prokaryotes, eukaryotes, or preferably both. See Giliman & Smith, *Gene* 8:81 (1979); Roberts, et al., *Nature,* 328:731 (1987); Schneider, B., et al., *Protein Expr. Purif.* 6435:10 (1995); Ausubel, Sambrook, Berger (all supra). The vector can be, for example, in the form of a plasmid, a bacterium, a virus, a naked polynucleotide, or a conjugated polynucleotide. The vectors are introduced into cells and/or microorganisms by standard methods including electroporation (From et al., *Proc. Natl. Acad. Sci. USA* 82, 5824 (1985), infection by viral vectors, high velocity ballistic penetration by small particles with the nucleic acid either within the matrix of small beads or particles, or on the surface (Klein et al., *Nature* 327, 70-73 (1987)), and/or the like.

A catalogue of Bacteria and Bacteriophages useful for cloning is provided, e.g., by the ATCC, e.g., *The ATCC Catalogue of Bacteria and Bacteriophage* (1996) Gherna et al. (eds) published by the ATCC. Additional basic procedures for sequencing, cloning and other aspects of molecular biology and underlying theoretical considerations are also found in Sambrook (supra), Ausubel (supra), and in Watson et al. (1992) *Recombinant DNA Second Edition* Scientific American Books, NY. In addition, essentially any nucleic acid (and virtually any labeled nucleic acid, whether standard or non-standard) can be custom or standard ordered from any of a variety of commercial sources, such as the Midland Certified Reagent Company (Midland, Tex. mcrc.com), The Great American Gene Company (Ramona, Calif. available on the World Wide Web at genco.com), ExpressGen Inc. (Chicago, Ill. available on the World Wide Web at expressgen.com), Operon Technologies Inc. (Alameda, Calif.) and many others.

The engineered host cells can be cultured in conventional nutrient media modified as appropriate for such activities as, for example, screening steps, activating promoters or selecting transformants. These cells can optionally be cultured into transgenic organisms. Other useful references, e.g. for cell isolation and culture (e.g., for subsequent nucleic acid isolation) include Freshney (1994) *Culture of Animal Cells, a Manual of Basic Technique*, third edition, Wiley-Liss, New York and the references cited therein; Payne et al. (1992) *Plant Cell and Tissue Culture in Liquid Systems* John Wiley & Sons, Inc. New York, N.Y.; Gamborg and Phillips (eds) (1995) *Plant Cell, Tissue and Organ Culture*; Fundamental Methods Springer Lab Manual, Springer-Verlag (Berlin Heidelberg New York) and Atlas and Parks (eds) *The Handbook of Microbiological Media* (1993) CRC Press, Boca Raton, Fla.

Proteins and Polypeptides of Interest

Methods of producing a protein in a cell with a selected amino acid at a specified position are also a feature of the invention. For example, a method includes growing, in an appropriate medium, the cell, where the cell comprises a nucleic acid that comprises at least one selector codon and encodes a protein; and, providing the selected amino acid, and incorporating the selected amino acid into the specified position in the protein during translation of the nucleic acid with the at least one selector codon, thereby producing the protein. The cell further comprises: an orthogonal glutamyl-tRNA (glutamyl-O-tRNA) that functions in the cell and recognizes the selector codon; and, an orthogonal aminoacyl-tRNA synthetase (O-RS) that preferentially aminoacylates the glutamyl-O-tRNA with the selected amino acid. Typically, the glutamyl O-tRNA comprises at least about, e.g., a 45%, a 50%, a 60%, a 75%, a 80%, or a 90% or more suppression efficiency in the presence of a cognate synthetase in response to the selector codon as compared to the glutamyl O-tRNA comprising or encoded by a polynucleotide sequence as set forth in SEQ ID NO.: 67 (AE(GC) tRNA). A protein produced by this method is also a feature of the invention.

The compositions of the invention and compositions made by the methods of the invention optionally are in a cell. The glutamyl O-tRNA/O-RS pairs or individual components of the invention can then be used in a host system's translation machinery, which results in a selected amino acid, e.g., unnatural amino acid, being incorporated into a protein. The International Application Number PCT/US2004/011786; and published Internation Application Number WO 2002/085923, supra, describe similar processes (e.g., with other orthogonal O-tRNA/O-RS pairs) and are incorporated herein by reference. For example, when an glutamyl O-tRNA/O-RS pair is introduced into a host, e.g., *Escherichia coli*, the pair leads to the in vivo incorporation of selected amino acid, such as an unnatural amino acid, e.g., a synthetic amino acid, such as derivative of a glutamate or glutamic acid amino acid, which can be exogenously added to the growth medium, into a protein, in response to a selector codon. Optionally, the compositions of the invention can be in an in vitro translation system, or in an in vivo system(s).

Essentially any protein (or portion thereof) that includes a selected amino acid, e.g., an unnatural amino acid, (and any corresponding coding nucleic acid, e.g., which includes one or more selector codons) can be produced using the compositions and methods herein. No attempt is made to identify the hundreds of thousands of known proteins, any of which can be modified to include one or more unnatural amino acid, e.g., by tailoring any available mutation methods to include one or more appropriate selector codon in a relevant translation system. Common sequence repositories for known proteins include GenBank EMBL, DDBJ and the NCBI. Other repositories can easily be identified by searching the internet.

Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more selected amino acid. Examples of therapeutic, diagnostic, and other proteins that can be modified to comprise one or more selected amino acid, e.g., an unnatural amino acid, can be found, but not limited to, those in U.S. Ser. No. 60/496,548, U.S. Ser. No. 60/479,931, and U.S. Ser. No. 60/463,869, supra; and, WO 2002/085923, supra.

In certain embodiments, the protein or polypeptide of interest (or portion thereof) in the methods and/or compositions of the invention is encoded by a nucleic acid. Typically, the nucleic acid comprises at least one selector codon, at least two selector codons, at least three selector codons, at least four selector codons, at least five selector codons, at least six selector codons, at least seven selector codons, at least eight selector codons, at least nine selector codons, ten or more selector codons.

Genes coding for proteins or polypeptides of interest can be mutagenized using methods well-known to one of skill in the art and described herein under "Mutagenesis and Other Molecular Biology Techniques" to include, e.g., one or more selector codon for the incorporation of a selected amino acid, e.g., an unnatural amino acid. For example, a nucleic acid for a protein of interest is mutagenized to include one or more selector codon, providing for the insertion of the one or more selected amino acids, e.g., unnatural amino acid. The invention includes any such variant, e.g., mutant, versions of any protein, e.g., including at least one selected amino acid. Similarly, the invention also includes corresponding nucleic acids, i.e., any nucleic acid with one or more selector codon that encodes one or more selected-amino acid.

To make a protein that includes a selected amino acid, one can use host cells and organisms that are adapted for the in vivo incorporation of the selected amino acid via orthogonal glutamyl tRNA/RS pairs. Host cells are genetically engineered (e.g., transformed, transduced or transfected) with one or more vectors that express the orthogonal glutamyl tRNA, the orthogonal glutamyl tRNA synthetase, and a vector that encodes the protein to be derivatized. Each of these components can be on the same vector, or each can be on a separate vector, or two components can be on one vector and the third component on a second vector. The vector can be, for example, in the form of a plasmid, a bacterium, a virus, a naked polynucleotide, or a conjugated polynucleotide.

Defining Polypeptides by Immunoreactivity

Because the polypeptides of the invention provide a variety of new polypeptide sequences (e.g., comprising selected amino acids (e.g., unnatural amino acids) in the case of proteins synthesized in the translation systems herein, or, e.g., in the case of the novel synthetases, novel sequences of standard amino acids), the polypeptides also provide new structural features which can be recognized, e.g., in immunological assays. The generation of antisera, which specifically bind the polypeptides of the invention, as well as the polypeptides which are bound by such antisera, are a feature of the invention. The term "antibody," as used herein, includes, but is not limited to a polypeptide substantially encoded by an immunoglobulin gene or immunoglobulin genes, or fragments thereof which specifically bind and recognize an analyte (antigen). Examples include polyclonal, monoclonal, chimeric, and single chain antibodies, and the like. Fragments of immunoglobulins, including Fab fragments and fragments produced by an expression library, including phage display, are also included in the term "antibody" as used herein. See, e.g., Paul, *Fundamental Immunology,* 4th Ed., 1999, Raven Press, New York, for antibody structure and terminology.

In order to produce antisera for use in an immunoassay, one or more of the immunogenic polypeptides is produced and purified as described herein. For example, recombinant protein can be produced in a recombinant cell. An inbred strain of mice (used in this assay because results are more reproducible due to the virtual genetic identity of the mice) is immunized with the immunogenic protein(s) in combination with a standard adjuvant, such as Freund's adjuvant, and a standard mouse immunization protocol (see, e.g., Harlow and Lane (1988) *Antibodies A Laboratory Manual*, Cold Spring Harbor Publications, New York, for a standard description of antibody generation, immunoassay formats and conditions that can be used to determine specific immunoreactivity.

Additional details on proteins, antibodies, antisera, etc. can be found in U.S. Ser. No. 60/496,548, U.S. Ser. No. 60/479,931, and U.S. Ser. No. 60/463,869, supra; WO 2002/085923, supra; patent application entitled "Glycoprotein synthesis" filed Oct. 15, 2003; and patent application entitled "Protein Arrays," filed on Dec. 22, 2002.

Use of Glutamyl O-tRNA and Glutamyl O-RS and Glutamyl O-tRNA/O-RS Pairs

The compositions of the invention and compositions made by the methods of the invention optionally are in a cell. The glutamyl O-tRNA/O-RS pairs or individual components of the invention can then be used in a host system's translation machinery, which results in a selected amino acid being incorporated into a protein. WO 2002/085923 by Schultz, et al., supra, describes related processes in general, and is incorporated herein by reference. For example, when an O-tRNA/O-RS pair is introduced into a host, e.g., *Escherichia coli*, the pair leads to the in vivo incorporation of a selected amino acid, which can be exogenously added to the growth medium, into a protein in response to a selector codon, e.g., an amber nonsense codon. Optionally, the compositions of the present invention can be in an in vitro translation system, or in an in vivo system(s). Proteins with the selected amino acid can be used as therapeutic proteins and can be used to facilitate studies on protein structure, interactions with other protein, and the like.

Kits

Kits are also a feature of the invention. For example, a kit for producing a protein that comprises at least one selected amino acid, e.g., an unnatural amino acid, in a cell is provided, where the kit includes a container containing a polynucleotide sequence encoding an glutamyl O-tRNA, and/or an glutamyl O-tRNA, and/or a polynucleotide sequence encoding an glutamyl O-RS, and/or an glutamyl O-RS. In one embodiment, the kit further includes a selected amino acid. In another embodiment, the kit further comprises instructional materials for producing the protein.

EXAMPLES

The following examples are offered to illustrate, but not to limit the claimed invention. One of skill will recognize a variety of non-critical parameters that may be altered without departing from the scope of the claimed invention.

Example 1

An Archaebacteria-Derived Glutamyl-tRNA Synthetase and tRNA Pair for Unnatural Amino Acid Mutagenesis In this embodiment of the invention, the development of an orthogonal glutaric acid synthetase and tRNA pair is described. The tRNA is derived from the consensus sequence obtained from a multiple sequence alignment of, e.g., archaeal $tRNA^{Glu}$ sequences. The glutamyl-tRNA synthetase is from, e.g., the achaebacterium *Pyrococcus horikoshii*. The new orthogonal pair suppresses, e.g., amber, nonsense codons with an efficiency roughly comparable to that of the orthogonal tyrosine pair derived from *Methanococcus jannaschii*, which has been used to selectively incorporate a variety of unnatural amino acids into proteins in *E. coli*. Development of the glutamic acid orthogonal pair increases the potential diversity of unnatural amino acid structures that can be incorporated into proteins in *E. coli*, and can permit the in vivo incorporation of multiple distinct unnatural amino acids into the same protein.

The ability to genetically incorporate unnatural amino acids into proteins offers new opportunities to investigate protein structure and function in vitro and in vivo, as well as produce large quantities of proteins with novel properties. This approach involves the directed evolution of the amino acid specificity of an aminoacyl-tRNA synthetase and tRNA pair that is orthogonal in, e.g., *E. coli*. See, e.g., 1. Liu, D. R. and Schultz, P. G. (1999) *Progress toward the evolution of an organism with an expanded genetic code. Proc. Natl. Acad. Sci. USA,* 96:4780-4785; Wang, L., Brock, A., Herberich, B. and Schultz, P. G. (2001) *Expanding the genetic code of Escherichia coli. Science,* 292:498-500; and, Santoro, S. W., Wang, L., Herberich, B., King, D. S. and Schultz, P. G. (2002) *An efficient system for the evolution of aminoacyl-tRNA synthetase specificity. Nat. Biotechnol.* 20:1044-1048. Such orthogonal pairs satisfy several criteria: the tRNA is not a substrate for any of the endogenous *E. coli* synthetases but functions efficiently in protein translation; the orthogonal synthetase efficiently aminoacylates the orthogonal tRNA, the anticodon of which has been modified to recognize a selector codon, e.g., an amber (UAG) or opal (UGA) stop codon, a four-base codon, etc.; and the synthetase does not aminoacylate any of the endogenous *E. coli* tRNAs. To date, several orthogonal pairs have been developed for use in *E. coli*, including glutamine (see, e.g., Liu, D. R. and Schultz, P. G. (1999) *Progress toward the evolution of an organism with an expanded genetic code. Proc. Natl. Acad. Sci. USA,* 96:4780-4785), aspartic acid (see, e.g., Pastrnak, M., Magliery, T. J. and Schultz, P. G. (2000) *A new orthogonal suppressor tRNA/aminoacyl-tRNA synthetase pair for evolving an organism with an expanded genetic code. Helvetica Chimica Acta,* 83:2277-2286) and tyrosine (see, e.g., Ohno, S., Yokogawa, T., Fujii, I., Asahara, H., Inokuchi, H. and Nishikawa, K. (1998) *Co-expression of yeast amber suppressor tRNATyr and tyrosyl-tRNA synthetase in Escherichia coli: possibility to expand the genetic code. J. Biochem.* (*Tokyo*), 124:1065-1068; and, Kowal, A. K., Kohrer, C. and RajBhandary, U. L. (2001) *Twenty-first aminoacyl-tRNA synthetase-suppressor tRNA pairs for possible use in site-specific incorporation of amino acid analogues into proteins in eukaryotes and in eubacteria. Proc. Natl. Acad. Sci. USA,* 98:2268-2273) pairs from *Saccharomyces cerevisiae*, a tyrosine pair from *Methanococcus jannaschii* (see, e.g., Wang, L., Magliery, T. J., Liu, D. R. and Schultz, P. G. (2000) *A new functional suppressor tRNA/aminoacyl-tRNA synthetase pair for the in vivo incorporation of unnatural amino acids into proteins. J. Am. Chem. Soc.,* 122:5010-5011), and a leucine pair from *Methanobacterium thermoautotrophicum* (see, e.g., Anderson J C, & Schultz P G, (2003), *Adaptation of an orthogonal archaeal leucyl-tRNA and synthetase pair for four-base, amber, and opal suppression, Biochemistry*, August 19; 42(32):9598-9608). In addition, glutamine (see, e.g., Kowal, A. K., Kohrer, C. and RajBhandary, U. L. (2001) *Twenty-first aminoacyl-tRNA synthetase-suppressor tRNA pairs for possible use in site-specific incorporation of amino acid analogues into proteins in eukaryotes and in eubacteria. Proc. Natl. Acad. Sci. USA,* 98:2268-2273) and tyrosine (see, e.g., Edwards and Schimmel (1990) *A bacterial amber suppressor in Saccharomyces cerevisiae is selectively recognized by a bacterial aminoacyl-tRNA synthetase. Mol. Cell. Biol.,*

10:1633-1641) synthetase-tRNA pairs from *E. coli* have been developed for use as orthogonal pairs in *S. cerevisiae.*

The orthogonal tyrosine pair from *M. jannaschii* has been successfully used to incorporate unnatural amino acids into proteins in *E. coli*. Many if not all of the unnatural amino acids that have been incorporated thus far using variants of the tyrosyl-tRNA synthetase are aryl derivatives, including p-azido- (see, e.g., Chin, J. W., Santoro, S. W., Martin, A. B., King, D. S., Wang, L. and Schultz, P. G. (2002) *Addition of p-azido-L-phenylalanine to the genetic code of Escherichia coli. J. Am. Chem. Soc.,* 124:9026-9027), p-benzoyl- (see, e.g., Chin, J. W., Martin, A. B., King, D. S., Wang, L. and Schultz, P. G. (2002) *Addition of a photocrosslinking amino acid to the genetic code of Escherichia coli. Proc. Natl. Acad. Sci. USA,* 99:11020-11024), p-amino- (see, e.g., Santoro, S. W., Wang, L., Herberich, B., King, D. S. and Schultz, P. G. (2002) *An efficient system for the evolution of aminoacyl-tRNA synthetase specificity. Nat. Biotechnol.* 20:1044-1048), p-isopropyl- (see, e.g., Santoro, S. W., Wang, L., Herberich, B., King, D. S. and Schultz, P. G. (2002) *An efficient system for the evolution of aminoacyl-tRNA synthetase specificity. Nat. Biotechnol.* 20:1044-1048), m-acetyl-(see, e.g., Wang, L., Zhang, Z., Brock, A. and Schultz, P. G. (2003) *Addition of the keto functional group to the genetic code of Escherichia coli. Proc. Natl. Acad. Sci. USA,* 100:56-61), and p-acetyl-phenylalanine (see, e.g., Wang, L., Zhang, Z., Brock, A. and Schultz, P. G. (2003) *Addition of the keto functional group to the genetic code of Escherichia coli. Proc. Natl. Acad. Sci. USA,* 100:56-61); O-methyl- (see, e.g., Wang, L., Brock, A., Herberich, B. and Schultz, P. G. (2001) *Expanding the genetic code of Escherichia coli. Science,* 292:498-500) and O-allyl-tyrosine (Santoro, S. W., Wang, L., Herberich, B., King, D. S. and Schultz, P. G. (2002) *An efficient system for the evolution of aminoacyl-tRNA synthetase specificity. Nat. Biotechnol.* 20:1044-1048; and, Zhang, Z., Wang, L., Brock, A. and Schultz, P. G. (2002) *The selective incorporation of alkenes into proteins in Escherichia coli. Angew. Chem. Int. Ed. Engl.,* 41:2840-2842); 3-(2-naphthyl)alanine (see, e.g., Wang, L., Brock, A. and Schultz, P. G. (2002) *Adding L-3-(2-Naphthyl) alanine to the genetic code of E. coli. J. Am. Chem. Soc.* 124:1836-1837), etc. In order to increase the structural and chemical diversity of unnatural amino acids that can be incorporated into proteins expressed by, e.g., *E. coli*, additional active orthogonal pairs would be useful.

Archaea appear to be an especially good source of orthogonal pairs for *E. coli*. Previous studies revealed that several archaeal tRNAs are not recognized by *E. coli* aminoacyl-tRNA synthetases (see, e.g., Kwok, Y. and Wong, J. T. (1980) *Evolutionary relationship between Halobacterium cutirubrum and eukaryotes determined by use of aminoacyl-tRNA synthetases as phylogenetic probes. Can. J. Biochem.,* 58:213-218). Two such synthetase-tRNA pairs derived from archaea, for tyrosine (see e.g., Wang, L., Magliery, T. J., Liu, D. R. and Schultz, P. G. (2000) *A new functional suppressor tRNA/aminoacyl-tRNA synthetase pair for the in vivo incorporation of unnatural amino acids into proteins. J. Am. Chem. Soc.,* 122:5010-5011) and leucine (see, e.g., Anderson J C, & Schultz P G, (2003), *Adaptation of an orthogonal archaeal leucyl-tRNA and synthetase pair for four-base, amber, and opal suppression, Biochemistry*, August 19; 42(32):9598-9608), were developed for use in *E. coli*. Both exhibited high levels of orthogonality and amber suppression efficiency. Moreover, these archaeal synthetases and tRNAs are efficiently produced and processed in *E. coli*. Finally, the recent proliferation of genomic sequence data for archaeal species and the commercial availability of their genomic DNA have facilitated the cloning of synthetases from these organisms as well as the design of compatible tRNAs.

Archaeal glutamyl-tRNA synthetases and tRNAs are attractive starting points for the generation of additional orthogonal pairs for several reasons. Archaeal glutamyl-tRNA synthetases are expected to tolerate changes in the anticodon loop of their substrate tRNAs since the enzyme naturally accommodates four different tRNA anticodons: UUC, CUC, UUG, and CUG. This is due to the fact that in archaeal species, glutamyl-tRNA synthetases must recognize and acylate both $tRNA^{Glu}$ and $tRNA^{Gln}$ (see, e.g., Tumbula, D. L., Becker, H. D., Chang, W. Z. and Soll, D. (2000) *Domain-specific recruitment of amide amino acids for protein synthesis. Nature,* 407:106-110). It follows that an archaeal glutamyl-tRNA synthetase should tolerate variance within at least two positions of the anticodon of its tRNA substrate, which should permit efficient aminoacylation of a tRNA bearing an amber-suppressing CUA anticodon. In addition, in vitro aminoacylation data (see, e.g., Kwok, Y. and Wong, J. T. (1980) *Evolutionary relationship between Halobacterium cutirubrum and eukaryotes determined by use of aminoacyl-tRNA synthetases as phylogenetic probes. Can. J. Biochem.,* 58:213-218) predict that archaeal glutamic acid and glutamine tRNAs should be orthogonal in *E. coli*. Finally, the three dimensional structure of the glutamyl-tRNA synthetase from *Thermus thermophilus* is known (see, e.g., Nureki, O., Vassylyev, D. G., Katayanagi, K., Shimizu, T., Sekine, S., Kigawa, T., Miyazawa, T., Yokoyama, S. and Morikawa, K. (1995) *Architectures of class-defining and specific domains of glutamyl-tRNA synthetase. Science,* 31:1958-1965; and, Sekine, S., Nureki, O., Shimada, A., Vassylyev, D. G. and Yokoyama, S. (2001) *Structural basis for anticodon recognition by discriminating glutamyl-tRNA synthetase. Nat. Struct. Biol.,* 8:203-206), which should facilitate the design of libraries of synthetase variants for use in directed evolution experiments.

Materials and Methods

Bacterial strains, plasmids, and reagents: *E. coli* strains DH5α and DH10B were purchased from Stratagene (La Jolla, Calif.) and Invitrogen Life Sciences (Carlsbad, Calif.), respectively. *Archaeoglobus fulgidus* (Af), *Aeropyrum pernix* (Ap), *Methanococcus jannaschii* (Mj), *Methanosarcina mazei Goel* (Mm), *Methanobacterium thermoautotrophicum* (Mt), *Pyrococcus horikoshii* (Ph), and *Sulfolobus solfataricus* (Ss) genomic DNA was obtained from ATCC (Manassas, Va.). *E. coli* genomic DNA was prepared from strain DH5a. Plasmid pKQ, which contains a ColE1 origin of replication, a kanamycin resistance marker, and cloning sites for an aminoacyl-tRNA synthetase gene, has been described previously (see, e.g., Anderson J C, & Schultz P G, (2003), *Adaptation of an orthogonal archaeal leucyl-tRNA and synthetase pair for four-base, amber, and opal suppression, Biochemistry*, August 19; 42(32):9598-9608). Plasmid pACKO-A184TAG, which contains a p15A origin of replication, a chloramphenicol resistance marker, a β-lactamase ampicillin resistance gene containing an amber stop codon at position Ala184, and tRNA cloning sites, has been described previously (see, e.g., Anderson J C, & Schultz P G, (2003), *Adaptation of an orthogonal archaeal leucyl-tRNA and synthetase pair for four-base, amber, and opal suppression, Biochemistry*, August 19; 42(32):9598-9608). Plasmid pArgU218, which contains a p15A origin of replication and encodes a kanamycin resistance marker and the isoacceptor of $tRNA^{Arg}$ corresponding to the codons AGA and AGG, has been described previously (see, e.g., Bullard, J. M., Cai, Y. C. and Spremulli, L. L. (2000) *Expression and characterization of the human mitochondrial leucyl-tRNA synthetase. Biochim. Biophys.*

*Acta,* 1490:245-258). Plasmid pBAD-Myc/HisA was purchased from Invitrogen. PCR reactions were carried out using the Expand Kit (Roche, Indianapolis, Ind.). Whole *E. coli* tRNA was purchased from Roche. Whole halobacterial tRNA was isolated from cultures of *Halobacterium* sp. NRC-1 using the RNA/DNA Extraction Kit (Qiagen). Overlap extensions were carried out using Taq polymerase (Stratagene). Restriction enzymes were purchased from New England Biolabs (Beverly, Mass.). DNA was purified using miniprep, gel purification, or PCR purification kits (Qiagen). Oligonucleotides were prepared by Qiagen Operon (Alameda, Calif.). Sequences of oligodeoxyribonucleotides used in this example:

```
pKQ-AfERS.N:
d(GGAGAGAAGACTACATGAAAGAAGTCATAATGAAATAC)

pKQ/pBAD-AfERS.C:
d(CGTTAGAAGACTGAATTCGGATTTTGGTCACGGGTGCG)

pKQ-ApERS.N:
d(GCTATCACACCATGGCGATGCTCCTAGGGGACCATC)

pKQ-ApERS.C:
d(GATCAGTCAGAATTCTTACTTGTGTGTGTATATCACCCTG)

pKQ-MjERS.N:
d(GGAGACGTCTCACATGGAAGAGAAGATATTGCC)

pKQ-MjERS.C:
d(CGTTACGTCTCGAATTTTATCTATGTGCATAGCAAC)

pKQ-MmERS.N:
d(GGAGACGTCTCACATGACCTTAAGTCCTGAAGA)

pKQ/pBAD-MmERS.C:
d(CGTTACGTCTCGAATTTTATTTATGAGCAAAGTACGCCACGAC)

pKQ-MtERS.N:
d(GGAGACGTCTCTCATGGTGCCAGTGGAGGACCT)

pKQ/pBAD-MtERS.C:
d(CGTTACGTCTCTAATTTTATTTGTGGGCATAGTAGAAG)

pKQ-PhERS.N:
d(GGAAAGGTCTCTCATGGATGTGGAAAAGATAGC)

pKQ/pBAD-PhERS.C:
d(GAGTAGGTCTCTAATTTTACTTGTGAGCATATATTG)

pKQ-SsERS.N:
d(GCTACTGCACCATGGAATTAAATGAATTACGAGAAC)

pKQ-SsERS.C:
d(GACTCAGTAGAATTCATTAGTCGTGTGAGAATACAACA)

AEGU-tRNA.F:
d(CGGAATTCGCCCCGGTGGTGTAGCCCGGCCAAGCATGCGGGCCTCT
AA)

AEGU-RNA.R:
d(AAACTGCAGTGGTGCCCCGGCCGGGATTTGAACCCGGGTCGCGGGCTT
TAGAGGCCCGCATGCTTGG)

AQGU-RNA.F:
d(CGAATTCAGCCCCGTGGTGTAGCGGCCAAGCATGCGGGGCTCTAAACC
CCGCGACCG)

AQGU-RNA.R:
d(AAACTGCAGTGGTAGCCCCGCGGGGATTCGAACCCCGGTCGCGGGGTT
TAGAGCC)

AQGC-RNA.F:
d(CGGAATTCAGCCCCGTGGTGTAGCGGCCAAGCACGCGGGGCTCTAAAC
CCCGCGACCG)
```

-continued

```
AQGC-RNA.R:
d(AAACTGCAGTGGTAGCCCCGCGGGGATTCGAACCCCGGTCGCGGGGTT
TAGAGCC)

AENN-RNA.F:
d(CGGAATTCGCCCCGGTGNTGTAGCCCGGCCAAGCANGCGGGCCTCT
AA)

pAC-tRNA.F:
d(GGACAGCGGTGCGGACTG)

pAC-tRNA.R:
d(GTGCTCAACGGCCTCAAC)

pBAD-EcERS.N:
d(AGGCTTTTAACCATGGCAAAAATCAAAACTCGCTTCGC)

pBAD-EcERS.C:
d(ACGTGAGAGGAATTCTGCTGATTTTCGCGTTCA)

pBAD-AfERS.C:
d(CGTTAGAAGACTGAATTGGGGTGAGTGTACACCGCGACCAGTTCCT
CG)

pBAD-MmERS.C:
d(CGTTACGTCTCGAATTCTTATGAGCAAAGTACGCCACGAC)

pBAD-MtERS.C:
d(CGTTACGTCTCTAATTTTTGTGGGCATAGTAGAAGACC)

pBAD-PhERS.C:
d(GAGTAGGTCTCTAATTCTTGTGAGCATATATTGCGATAA)
```

Cloning of aminoacyl-tRNA synthetase genes: The open reading frames of glutamyl-tRNA synthetase from *A. fulgidus* (AfERS), *A. pernix* (ApERS), *M. jannaschii* (MjERS), *M. mazei* (MmERS), *M. thermoautotrophicum* (MtERS), *P. horikoshii* (PhERS), and *S. solfataricus* (SsERS) were amplified by PCR using genomic DNA as template and the appropriate oligonucleotide primers (see above) to yield products of ~1.7 kilo-base pairs (kbp). In these experiments, the amplification of the MjERS gene was unsuccessful. The AfERS PCR product was digested with BbsI, the ApERS and SsERS products with EcoRI and NcoI, the MmERS and MtERS products with BsmBI, and the PhERS product with BsaI to generate EcoRI/NcoI compatible cohesive ends for all products. Construction of plasmids pKQ-AfERS, pKQ-ApERS, pKQ-MjERS, pKQ-MmERS, pKQ-MtERS, pKQ-PhERS, and pKQ-SsERS was accomplished by insertion of restriction-digested, gel-purified glutamyl-tRNA synthetase gene PCR fragments into plasmid pKQ. Plasmid constructs were confirmed by restriction mapping and sequencing of individual clones.

Design and cloning of tRNAs: Consensus archaeal tRNA genes were identified by alignment using the program pileup from Genetics Computer Group, Inc. (GCG). Genes for tRNAs were constructed by overlap extension of the appropriate forward and reverse primers (see above). EcoRI/PstI-digested extension fragments were inserted into a 4.2 kbp fragment of plasmid pACKO-A184TAG to construct plasmids pAC-AE(GU), pAC-AQ(GU), and pAC-AQ(GC). The AE(NN) tRNA library was constructed by PCR amplification using primers AE(NN)-RNA.F and pAC-tRNA.R with plasmid pAC-AE(GU) as template. The pAC-AE(NN) plasmid library was constructed by insertion of the EcoRI/PstI-digested AE(NN) tRNA library PCR fragment into the tRNA cloning site of pACKO-A184TAG. Plasmid constructs were confirmed by sequence analysis

.

Nomenclature of tRNAs:

AQ(GU): A-archaeal; Q-glutaminyl; GU-base pair at postion 10-26

AQ(GC): A-archaeal; Q-glutaminyl; GC-base pair at postion 10-26

AE(GU): A-archaeal; E-glutamyl; GU-base pair at postion 10-28

AE(GC): A-archaeal; E-glutamyl; GC-base pair at postion 10-28

AE(NN): A-archaeal; E-glutamyl; NN-base pair at postion 10-28

Ampicillin $IC_{50}$ value measurements: To examine the orthogonality of tRNAs, 10 μL of *E. coli* DH10B cells (1 cfu/μL) carrying a tRNA-expressing plasmid were plated on a series of LB agar plates containing chloramphenicol and varying concentrations of ampicillin. To measure the $IC_{50}$ values for cells carrying both tRNA- and synthetase-expressing plasmids, cells were plated on LB agar plates containing chloramphenicol, kanamycin, and varying concentrations of ampicillin. In the initial series, cells were plated on five ampicillin concentrations varying from 0 to 1000 μg/mL and incubated overnight at 37° C. In subsequent series, cells were plated on a narrower ampicillin concentration range surrounding the value initial ampicillin $IC_{50}$ value estimate. Typically, 10 ampicillin concentrations spanning a range ±45% of the initial $IC_{50}$ estimate were tested in 10% increments. Measurements were made in duplicate or triplicate for each cell strain.

Optimization of the AEGU tRNA: *E. coli* DH10B cells carrying plasmid pKQ-MmERS were transformed with the pAC-AE(NN) plasmid library to yield ~$10^6$ independent transformants. Cells were plated (~1000 cfu/plate) on a series of ten LB agar plates containing chloramphenicol, kanamycin, and 0-1000 μg/mL ampicillin. Ten individual colonies from the plate containing 500 μg/mL ampicillin were picked and their pAC-AE(NN) plasmids amplified, miniprepped, and sequenced.

Synthetase overexpression: Aminoacyl-tRNA synthetase genes were PCR-amplified using the appropriate N- and C-terminal pBAD construct primers (see Bacterial strains, plasmids and reagents) and the appropriate synthetase pKQ construct templates. The AfERS PCR product was digested with BbsI, the EcERS product with EcoRI and NcoI, the MmERS and MtERS products with BsmBI, and the PhERS product with BsaI to generate EcoRI/NcoI compatible cohesive ends for all products. Construction of the synthetase pBAD plasmids was accomplished by insertion of restriction-digested, gel-purified PCR fragments into the EcoRI and NcoI cloning sites of plasmid pKQ. Plasmid constructs were confirmed by restriction mapping and sequencing of individual clones. The synthetase pBAD plasmids were transferred to DH10B cells carrying plasmid pArgU218. Individual colonies were used to inoculate 500-mL cultures of 2YT containing ampicillin and kanamycin. Protein was isolated according to the QIAexpressionist (Qiagen) protocol under native conditions and dialyzed overnight against 20 mM Tris-HCl (pH 8), 200 mM NaCl, and 1 mM DTT. Glycerol was added to protein samples to a final concentration of 50%. Glycerol-containing samples were stored at −20° C. Protein concentrations were determined using sodium-dodecyl sulfate polyacrylamide gel electrophoresis by comparison to a BSA standard.

In vitro aminoacylation assays: Reactions were carried out as described previously (see, e.g., Hoben, P. and Soll, D. (1985) *Glutaminyl-tRNA synthetase of Escherichia coli. Methods Enzymol.,* 113:55-59). Each 20-μL reaction contained 50 mM Tris-HCl (pH 7.5), 30 mM KCl, 20 mM $MgCl_2$, 0.1 mg/mL BSA, 5 mM glutathione, 2.5 mM ATP, 100 nM 1-[G-$^3$H]Glutamic acid (Amersham), 750 nM aminoacyl-tRNA synthetase, and 40 μM whole halobacterial tRNA. Reactions were allowed to proceed for 15 minutes at 37° C.

Results and Discussion

Development of an orthogonal tRNA: An orthogonal tRNA derived from the consensus sequence of archaeal leucine tRNAs can serve as an efficient substrate for archaeal leucyl-tRNA synthetases. See, e.g., the generation of an orthogonal $tRNA^{Leu}$ (see e.g., Anderson J C, & Schultz P G, (2003), *Adaptation of an orthogonal archaeal leucyl-tRNA and synthetase pair for four-base, amber, and opal suppression, Biochemistry*, August 19; 42(32):9598-9608). The design of an orthogonal tRNA using this strategy involves: alignment of a group of related tRNA sequences to determine the consensus sequence; analysis of the secondary structure of the consensus-derived tRNA to identify and correct potentially deleterious non-canonical base pairs; and conversion of the anticodon of the consensus tRNA to CUA to allow recognition and suppression of an amber stop codon within the target mRNA. The same strategy was applied to construct a cognate orthogonal tRNA for archaeal glutamyl-tRNA synthetases.

In archaebacteria, a single enzyme, glutamyl-tRNA synthetase, aminoacylates both $tRNA^{Glu}$ and $tRNA^{Gln}$. The product of the latter reaction, glu-$tRNA^{Gln}$, is subsequently converted to gln-$tRNA^{Gln}$ by transamidation (see, e.g., Tumbula, D. L., Becker, H. D., Chang, W. Z. and Soll, D. (2000) *Domain-specific recruitment of amide amino acids for protein synthesis. Nature,* 407:106-110). Previous reports suggest that both archaeal $tRNA^{Glu}$ and archaeal $tRNA^{Gln}$ are not substrates for endogenous *E. coli* synthetases (see, e.g., Kwok, Y. and Wong, J. T. (1980) *Evolutionary relationship between Halobacterium cutirubrum and eukaryotes determined by use of aminoacyl-tRNA synthetases as phylogenetic probes. Can. J. Biochem.,* 58:213-218). Thus, both tRNAs were viewed as attractive starting points for the development of an orthogonal tRNA using the consensus sequence design strategy. The available archaeal $tRNA^{Glu}$ and $tRNA^{Gln}$ sequences were separately aligned, revealing a high degree of homology within each family (Tables 1 and 2). The consensus sequence of each family was derived by identification of the consensus base at each position within the primary sequence. The consensus $tRNA^{Glu}$ sequence contains three positions outside of the anticodon (positions 3, 25, and 72) at which two bases predominate with approximately equal frequency (Table 1). The consensus $tRNA^{Gln}$ sequence contains five positions outside the anticodon (positions 16, 32, 40, 51 and 63) at which two bases predominate with approximately equal frequency and two positions (positions 6 and 67) at which one base predominates but does not represent a majority at its position (Table 2).

The secondary structures of the consensus archaeal $tRNA^{Glu}$ and $tRNA^{Gln}$ sequences (FIG. 1, Panel A) were used to design three candidate orthogonal tRNAs (FIG. 1, Panel B). The anticodon loops contained the sequence CUA for suppression of an amber stop codon (UAG). The nucleotide to the 3' side of each anticodon was converted to A to improve suppression efficiency in *E. coli* (see, e.g., Anderson J C, & Schultz P G, (2003), *Adaptation of an orthogonal archaeal leucyl-tRNA and synthetase pair for four-base, amber, and opal suppression, Biochemistry*, August 19; 42(32):9598-9608). Consensus $tRNA^{Glu}$ and $tRNA^{Gln}$ structures contain a conserved non-canonical G-U base pair at positions 10-28 and 10-26, respectively (FIG. 1, Panel A). Although it has been demonstrated that alteration of non-canonical base pairs within orthogonal tRNAs can improve amber stop codon suppression efficiency in *E. coli* (see, e.g., Anderson J C, & Schultz P G, (2003), *Adaptation of an orthogonal archaeal leucyl-tRNA and synthetase pair for four-base, amber, and opal suppression, Biochemistry*, August 19; 42(32):9598-9608), the conserved nature of this pair suggested that it might constitute an important identity element for recognition by archaeal glutamyl-tRNA synthetases. Therefore, in designing the $tRNA^{Glu}$ orthogonal tRNA, AE(GU), the 10-28 G-U base pair was preserved (FIG. 1, Panel B). In designing the $tRNA^{Gln}$ orthogonal tRNAs, AQ(GU) and AQ(GC), the 10-26 pair was either preserved or changed to a G-C pair, respectively.

TABLE 1

ARCHAEAL GLUTAMIC ACID AND CONSENSUS tRNAs

| tRNA (anticodon) | Sequence[1] |
|---|---|
| *Aeropyrum pernix* (CUC) | GCCGCGGUAGUAUAGCCCGGCCCAGUAUGCGGGCCUCUCGAGCCCGU<br>GACCCGGGUUCAAAUCCCGGCCGCGGCACCA |
| *Aeropyrum pernix* (UUC) | GCCGCGGUAGUAUAGCCCGGCCCAGUAUGCGGGCCUUUCGAGCCCGU<br>GACCCGGGUUCAAAUCCCGGCCGCGGCACCA |
| *Archaeoglobus fulgidus* (CUC) | GCUCCGGUGGUGUAGCCCGGCCAAUCAUACGGGACUCUCGAUCCCGU<br>GACCCGGGUUCAAAUCCCGGCCGGAGCACCA |
| *Archaeoglobus fulgidus* (UUC) | GCUCCGGUGGUGUAGCCCGGCCAAUCAUUCCGGCCUUUCGAGCCGGC<br>GACCCGGGUUCAAAUCCCGGCCGGAGCACCA |
| *Halobacterium* sp. (CUC) | GCUCCGUUGGUGUAGUCCGGCCAAUCAUCUUGCCCUCUCACGGCAAG<br>GACUAGGGUUCAAAUCCCUGACGGAGCACCA |
| *Halobacterium* sp. (UUC) | GCUCGGUUGGUGUAGUCCGGCCAAUCAUGUUGGCCUUUCGAGCCGA<br>CGACCAGGGUUCAAAUCCCUGACCGAGCACCA |
| *Methanobacterium thermautotrophicus* (UUC) | GCUCCGGUAGUGUAGUCCGGCCAAUCAUUUCGGCCUUUCGAGCCGAA<br>GACUCGGGUUCAAAUCCCGGCCGGAGCACCA |
| *Methanococcus jannaschii* (UUC) | GCUCCGGUGGUGUAGUCCGGCCAAUCAUGCGGGCCUUUCGAGCCCGC<br>GACCCGGGUUCAAAUCCCGGCCGGAGCACCA |
| *Methanococcus maripaludis* (UUC) | GCUCCAGUGGUGUAGUCCGGCCAAUCAUCCGGCCCUUUCGAGGCCGG<br>GACUCGGGUUCAAAUCCCGGCUGGAGCACCA |
| *Methanosarcina mazei* (CUC) | GCUCCGAUAGUGUAGCUCGGCCAAUCAUUCAGGACUCUCACUCCUGC<br>GACUGGGGUUCAAAUCCCCAUCGGAGCACCA |
| *Methanosarcina mazei* (UUC) | GCUCCGGUAGUGUAGUCCGGCCAAUCAUUCCGGCCUUUCGAGCCGAA<br>GACUCGGGUUCGAAUCCCGGCCGGAGCACCA |
| *Pyrobaculum aerophilum* (CUC) | CAGCCGGUAGUCUAGCCCGGACAAUGAUGCGGGCCUCUCGAGCCCGU<br>GACCCGGGUUCAAAUCCCGGCCGGAGCACCA |
| *Pyrococcus abyssi* (CUC) | GCCCCGGUGGUGUAGCCCGGUCAAUCAUGCGGGACUCUCGAUCCCGC<br>GACCCGGGUUCAAAUCCCGGCCGGGGCACCA |
| *Pyrococcus abyssi* (UUC) | GCCCCGGUGGUGUAGCCCGGUCAAACAUGCGGGCCUUUCGAGCCCGC<br>GCCCCGGGUUCAAAUCCCGGCCGGGGCACCA |
| *Pyrococcus furiosus* (CUC) | GCCCCGGUGGUGUAGCCCGGUCAAUCAUGCGGGACUCUCGAUCCCGC<br>GACCCGGGUUCAAAUCCCGGCCGGGGCACCA |
| *Pyrococcus furiosus* (UUC) | GCCCCGGUGGUGUAGCCCGGUCAAACAUGCGGGCCUUUCGAGCCCGC<br>GCCCCGGGUUCAAAUCCCGGCCGGGGCACCA |
| *Pyrococcus horikoshii* (CUC) | GCCCCGGUGGUGUAGCCCGGUCAAUCAUGCGGGACUCUCGAUCCCGC<br>GACCCGGGUUCAAAUCCCGGCCGGGGCACCA |
| *Pyrococcus horikoshii* (UUC) | GCCCCGGUGGUGUAGCCCGGCCAAACAUGCGGGCCUUUCGAGCCCGC<br>GCCCCGGGUUCAAAUCCCGGCCGGGGCACCA |
| *Sulfolobus solfataricus* (CUC) | GCCGCGGUGGUUUAGCCCGGUC-<br>AGAAUGCGGGCCUCUCGAGCCCGUGACCCGGGUUCAAAUCCCGGCC<br>GCGGCACCA |

TABLE 1-continued

ARCHAEAL GLUTAMIC ACID AND CONSENSUS tRNAs

| tRNA (anticodon) | Sequence[1] |
|---|---|
| *Sulfolobus solfataricus* (UUC) | GCCGCGGUGGUUUAGCCCGGUC-<br>AGAAUGCGGGCCUUUCGAGCCCGUGACCCGGGUUCAAAUCCCGGCCG<br>CGGCACCA |
| *Sulfolobus tokodaii* (CUC) | GCCGCGGUAGUAUAGCCCGGUC-<br>AGUAUGCGGGCCUCUCAAGCCCGUGGCCCGGGUUCAAAUCCCGGCCG<br>CGGCACCA |
| *Sulfolobus tokodaii* (UUC) | GCCGCGGUAGUAUAGCCCGGUCAAGCACGCGGGCCUUUCGAGCCCGU<br>GACCCGGGUUCAAAUCCCGGCCGCGGCACCA |
| *Thermoplasma acidophilum* (CUC) | GCUCCGGUGGUGUAGUCCGGCCAAGCAUUAGGGACUCUCAAUCCCCC<br>GACUCGGGUCCAAAUCCCGACCGGAGCACCA |
| *Thermoplasma acidophilum* (UUC) | GCUCCGGUGGUAUAGUCCGGACAAGCAUAUCGGCCUUUCGAGCCGA<br>CGACCUGGGUCCAAAUCCCGGCCGGAGCACCA |
| *Thermoplasma volcanium* (CUC) | GCUCCGGUGGUGUAGUCCGGCCAAGCAUUAGGGACUCUCAAUCCCCC<br>GACUCGGGUCCAAAUCCCGACCGGAGCACCA |
| *Thermoplasma volcanium* (UUC) | GCUCCGGUGGUGUAGUCCGGACAAGCAUAUCGGCCUUUCGAGCCGA<br>CGACCUGGGUCCAAAUCCCGGCCGGAGCACCA |
| Consensus (YUC)[2] | GC**Y**CCGGUGG**U**GUAGCCCGGCCAAKCA**U**GCGGGCCUYUCGAGCCCG<br>CGACCCGGGUUCAAAUCCCGGCCGG**R**GCACCA |
| AE(GU) (CUA)[3] | GCcCCGGUGGUGUAGCCCGGCCAAgCAUGCGGGCCUcUAaAGCCCGCGA<br>CCCGGGUUCAAAUCCCGGCCGGgGCACCA |

[1]Bases indicated by underlining deviate from the identity of their consensus bases. Bases highlighted in black correspond to positions at which two different bases predominate with approximately equal frequency. Anticodon positions are boxed.
[2]Bases that are in boldface correspond to positions involved in non-canonical base pairs (FIG. 1, Panel A). Y corresponds to bases C or U; R corresponds to bases A or G; S corresponds to bases C or G.
[3]Bases in lowercase correspond to positions that were varied from the consensus sequence in the design of a prospective orthogonal tRNA (FIG. 1, Panel B).

TABLE 2

ARCHAEAL GLUTAMINE AND CONSENSUS tRNAs

| tRNA (anticodon) | Sequence[1] |
|---|---|
| *Aeropyrum pernix* (CUG) | AGCCGGGUCGUCUAGCGGCCCAGGAUGCGGGGCUCUGGCCCC<br>CGUGACCGGGGUUCGAAUCCCCGCCCGGCUACCA |
| *Aeropyrum pernix* (UUG) | AGCCGGGUCGUCUAGCGGCCCAGGAUGCGGGGUUUUGGCCCC<br>CGUGACCCGGGUUCGAAUCCGGGCCCGGCUACCA |
| *Archaeoglobus fulgidus* (CUG) | AGCCCCGUGGGGUAGCGGUCAAUCCUGCCGGACUCUGGAUCC<br>GGCGACGCCGGUUCGAAUCCGGCCGGGGCUACCA |
| *Archaeoglobus fulgidus* (UUG) | AGCCCCGUGGUGUAGCGGUCAAUCAUGCGGGCCUUUGGAGCC<br>CGCGACCGCGGUUCGAAUCCCCGCGGGGCUACCA |
| *Halobacterium* sp. (CUG) | AGUCCCGUAGGGUAGUGGCCAAUCCUGAAGCCUUCUGGGGGC<br>UUCGACGGAAGUUCGAAUCUUCCCGGGACUACCA |
| *Halobacterium* sp. (UUG) | AGUCCCGUGGUGUAGUGGCCAAUCAUAUGGGCCUUUGGAGCC<br>CACGACGGCGGUUCGAAUCCGCCCGGGACUACCA |
| *Methanobacterium thermautotrophicus* (CUG) | AGUCCCGUGGGGUAAUGGCA-<br>AUCCUGAUGGACUCUGGAUCCAUCGAUAGCGGUUCGACUCCG<br>CUCGGGACUACCA |
| *Methanobacterium thermautotrophicus* (UUG) | AGUCCCGUGGGGUAGUGGUA-<br>AUCCUGCUGGCCUUUGGACCCGGCGACAGCGGUUCGACUCCG<br>CUCGGGACUACCA |

TABLE 2-continued

ARCHAEAL GLUTAMINE AND CONSENSUS tRNAs

| tRNA (anticodon) | Sequence[1] |
|---|---|
| *Methanococcus jannaschii* (UUG) | AGCCCGGUGGUGUAGUGGCCUAUCAUCCGGGGCUUUGGACCC<br>CGGGACCGCGGUUCGAAUCCGCGCCGGGCUACCA |
| *Methanococcus maripaludis* (UUG) | AGCCCAGUAGUGUAGUGGCCAAUCAUCCGUGCCUUUGGAGCA<br>UGGGACCGCGGUUCGAAUCCGCGCUGGGCUACCA |
| *Methanopyrus kandleri* (UUG) | AGGGCCGUGGGGUAGCGGUCUAUCCUGCGGGGCUUUGGACCC<br>CGCGACCCCGGUUCAAAUCCGGGCGGCCCUACCA |
| *Methanosarcina mazei* (CUG) | AGCCCGGUAGUGUAGUGGUCAAUCAUGCGGGACUCUGGACCC<br>UGCAACCUCGGUUCGAAUCCGUGCCGGGCUACCA |
| *Methanosarcina mazei* (UUG) | AGUCCUGUAGGGUAGUGGUCAAUCCUUCGGGCCUUUGGAGCC<br>CGGGACAGCGGUUCGAAUCCGCUCAGGACUACCA |
| *Pyrobaculum aerophilum* (CUG) | AGCCCGGUCGUCUAGCGGCC-<br>AGGAUGCGGGGCUCUGGACCCCGUGGCCCGGGUUCGAAUCCC<br>GGCCGGGCUACCA |
| *Pyrobaculum aerophilum* (UUG) | AGCCCGGUCGUCUAGCGGCCAAGGAUGCGGGGCUUUGGACCC<br>CGUGGCCCGGGUUCGAAUCCCGGCCGGGCUACCA |
| *Pyrococcus abyssi* (CUG) | AGCCCCGUGGUGUAGCGGCCAAGCAUGCGGGACUCUGGAUCC<br>CGCGACCGGGGUUCGAAUCCCCGCGGGGCUACCA |
| *Pyrococcus abyssi* (UUG) | AGCCCCGUGGUGUAGCGGCCAAGCAUGCGGGACUUUGGAUCC<br>CGCGACCCGGGUUCGAAUCCCGGCGGGGCUACCA |
| *Pyrococcus furiosus* (CUG) | AGCCCCGUGGUGUAGCGGCCAAGCAUGCGGGACUCUGGAUCC<br>CGCGACCGGGGUUCGAAUCCCCGCGGGGCUACCA |
| *Pyrococcus furiosus* (UUG) | AGCCCCGUGGUGUAGCGGCCAAGCAUGCGGGACUUUGGAUCC<br>CGCGACCCGGGUUCGAAUCCCGGCGGGGCUACCA |
| *Pyrococcus horikoshii* (CUG) | AGCCCCGUGGUGUAGCGGCCAAGCAUGCGGGACUCUGGAUCC<br>CGCGACCGGGGUUCGAAUCCCCGCGGGGCUACCA |
| *Pyrococcus horikoshii* (UUG) | AGCCCCGUGGUGUAGCGGCCAAGCAUGCGGGACUUUGGAUCC<br>CGCGACCCGGGUUCGAAUCCCGGCGGGGCUACCA |
| *Sulfolobus solfataricus* (CUG) | AGCCGGGUAGUCUAGUGGUCAAGGAUCCAGGGCUCUGGCCCCC<br>UGGGACCAGGGUUCGAAUCCCUGCCCGGCUACCA |
| *Sulfolobus solfataricus* (UUG) | AGCCGGGUAGUCUAGUGGUCAAGGAUCCAGGGCUUUGGCCCCC<br>UGGGACCAGGGUUCGAAUCCCUGCCCGGCUACCA |
| *Sulfolobus tokodaii* (CUG) | AGCCGGGUCGUCUAGUGGUCAAGGAUCGAGGGCUCUGGCCCCC<br>UCGGACCUGGGUUCAAAUCCCAGCCCGGCUACCA |
| *Sulfolobus tokodaii* (UUG) | AGCCGGGUCGUCUAGUGGUCAAGGAUCGAGGGCUUUGGCCCCC<br>UCGGACCUGGGUUCAAAUCCCAGCCCGGCUACCA |
| *Thermoplasma acidophilum* (CUG) | AGCCCUGUGGUGUAGUGGCCAAGCAUUAUGGGCUCUGGACCC<br>AUCGACGGCAGUUCGAAUCUGCCCAGGGCUACCA |
| *Thermoplasma acidophilum* (UUG) | AGCCCUGUGGUGUAGUGGACAAGCAUUUUGGACUUUGGAUUC<br>CAAAGACGGCAGUUCGAAUCUGCCCAGGGCUACCA |
| *Thermoplasma volcanium* (CUG) | AGCCCUGUGGUGUAGCGGCCAAGCAUUAUGGTCUCUGGACCC<br>AUCGACGGCAGUUCGAAUCUGCCCAGGGCUACCA |
| *Thermoplasma volcanium* (UUG) | AGCCCUGUGGUGUAGUGGACAAGCAUUUUGGACUUUGGAUCC<br>AACGACGGCAGUUCGAAUCUGCCCAGGGCUACCA |

TABLE 2-continued

ARCHAEAL GLUTAMINE AND CONSENSUS tRNAs

| tRNA (anticodon) | Sequence[1] |
|---|---|
| Consensus (YUG)[2] | AGCCCCGUG**G**UGUAGYGGCCAAGCA**U**GCGGGRCUYUGGAYCC CGCGACCGSGGUUCGAAUCCSCGCGGGGCUACCA |
| AQ(GU) (CUA)[3] | AGCCCCGUGGUGUAGcGGCCAAGCAUGCGGGgCUcUaaAcCCCGC GACCGgGGUUCGAAUCCcCGCGGGGCUACCA |
| AQ(GC) (CUA)[3] | AGCCCCGUGGUGUAGcGGCCAAGCAcGCGGGgCUcUaaAcCCCGC GACCGgGGUUCGAAUCCcCGCGGGGCUACCA |

[1]Bases indicated by underlining deviate from the identity of their consensus bases. Bases highlighted in black correspond to positions at which two different bases predominate with approximately equal frequency. Anticodon positions are boxed.
[2]Bases that are in boldface correspond to positions involved in non-canonical base pairs (FIG. 1, Panel A). Y corresponds to bases C or U; R corresponds to bases A or G; S corresponds to bases C or G.
[3]Bases in lowercase correspond to positions that were varied from the consensus sequence in the design of a prospective orthogonal tRNA (FIG. 1, Panel B).

Figure 2:
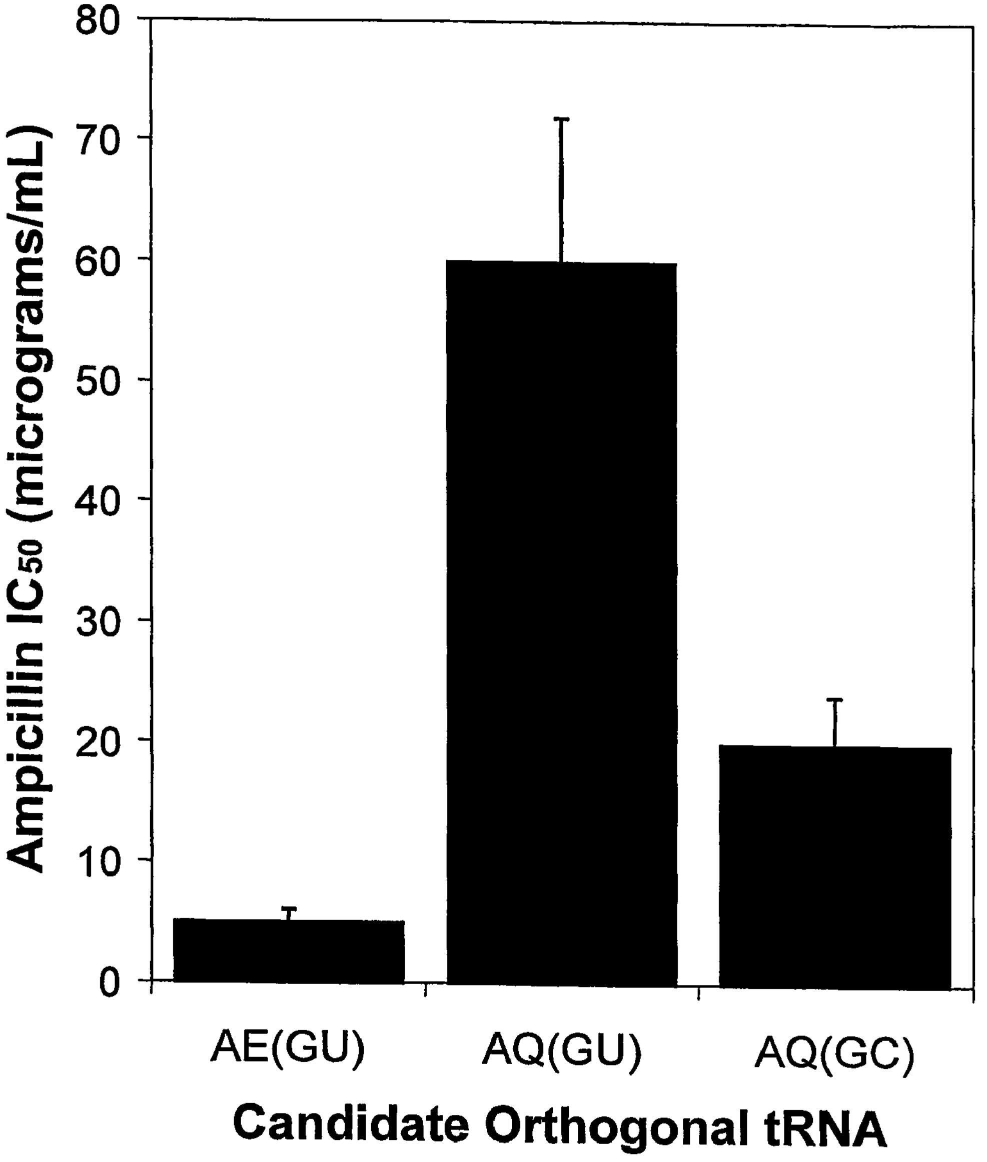
FIG. 2 provides a histogram demonstrating the orthogonality of candidate tRNAs in *E. coli*, e.g., using a β-lactamase amber suppression assay to measure the ampicillin $IC_{50}$ values for *E. coli* expressing the indicated tRNA.

Orthogonality of tRNAs: To test the activity and cross-reactivity of the AE(GU), AQ(GU), and AQ(GC) tRNAs, their genes were inserted into plasmid pACKO-A184TAG. *E. coli* cells were transformed with the resulting plasmids, pAC-AE (GU), pAC-AQ(GU), and pAC-AQ(GC), and the ampicillin $IC_{50}$ values for the cells were assayed. The tRNA-expressing pAC-based plasmids carry a β-lactamase reporter gene containing an amber mutation at the permissive site Ala184, which serves as a useful reporter for amber codon suppression. Acylation of an amber suppressor tRNA causes the incorporation of the activated amino acid at position 184 of β-lactamase, resulting in suppression of the amber stop codon, production of active full-length β-lactamase and resistance to ampicillin. Because an orthogonal tRNA should not cross-react with endogenous aminoacyl-tRNA synthetases, strains transformed with an orthogonal suppressor tRNA alone should survive only on low concentrations of ampicillin. To assess the orthogonality of designed tRNAs, *E. coli* transformants were plated on LB agar plates containing varying concentrations of ampicillin (FIG. 2). Cells expressing the AQ(GU) and AQ(GC) tRNAs exhibited ampicillin $IC_{50}$ values of 60±12 and 20±4 μg/mL, respectively. Cells expressing the AE(GU) tRNA exhibited a relatively lower ampicillin $IC_{50}$ value of 5±1 μg/mL, suggesting that this tRNA is the least cross-reactive of the three.

Figure 3:
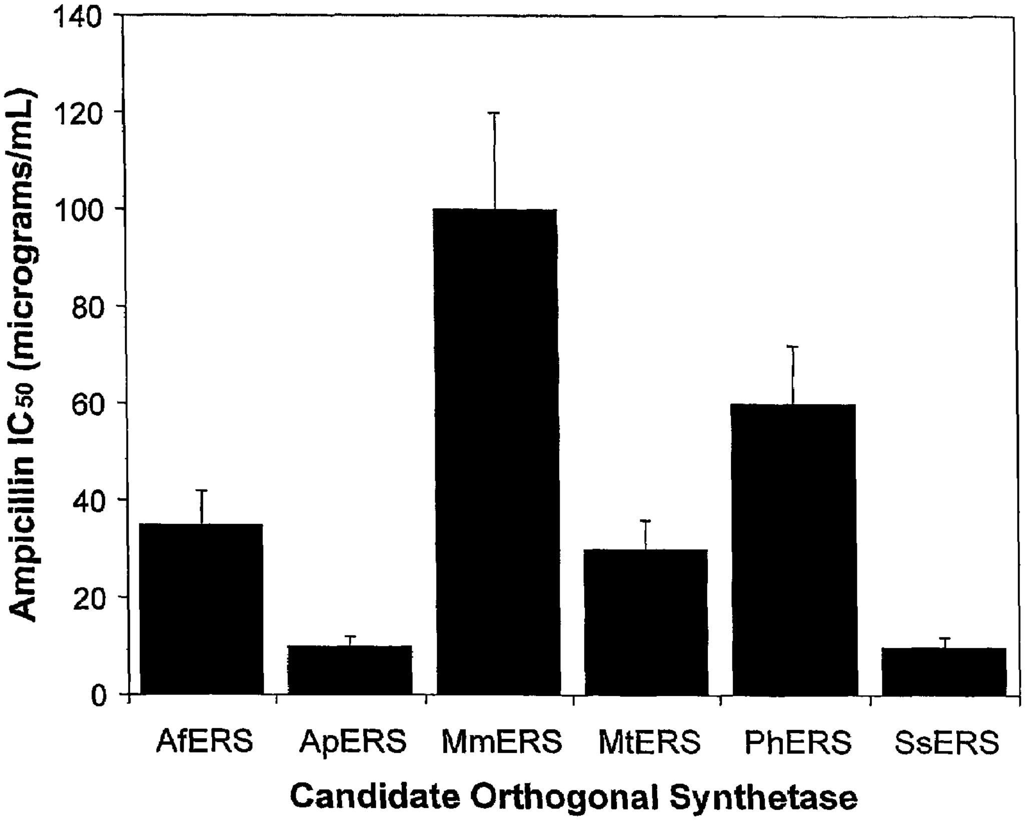
FIG. 3 provides a histogram demonstrating aminoacylation of the AE(GU) tRNA by orthogonal synthetase candidates in *E. coli*, e.g., using a β-lactamase amber suppression assay to measure the ampicillin $IC_{50}$s of *E. coli* expressing the indicated glutamyl-tRNA synthetase together with the AE(GU) tRNA. Ampicillin $IC_{50}$ values reflect amber suppression efficiency in *E. coli.*

Cloning and assaying archaeal glutamyl-tRNA synthetases in *E. coli*: Based on previous experiments (see, e.g., Anderson J C, & Schultz P G, (2003), *Adaptation of an orthogonal archaeal leucyl-tRNA and synthetase pair for four-base, amber, and opal suppression, Biochemistry*, August 19; 42(32):9598-9608), it was anticipated that the AE(GU), AQ(GU) and AQ(GC) tRNAs might serve as substrates for archaeal glutamyl-tRNA synthetases. Suppression efficiencies corresponding to various synthetases-tRNA pair combinations were assessed using the ampicillin $IC_{50}$ assay. If the designed tRNAs are recognized by the archaeal synthetases, then *E. coli* cells co-expressing the synthetase-tRNA pairs should exhibit ampicillin $IC_{50}$ values greater than those displayed by cells expressing tRNAs alone. The AfERS, ApERS, MnERS, MtERS, PhERS, and SsERS genes were each inserted into the vector pKQ, which can be co-maintained in *E. coli* in combination with the tRNA-expressing plasmids. Following co-transformation of *E. coli* with all pair-wise combinations of synthetase- and tRNA-expressing plasmids, cells were grown on LB agar plates containing varying concentrations of ampicillin. Cells expressing synthetase-AQ (GU) or synthetase-AQ(GC) combinations exhibited $IC_{50}$ values equivalent to those of cells expressing AQ(GU) alone or AQ(GC) alone, respectively, suggesting that neither of these tRNAs is recognized by any of the archaeal glutamyl-tRNA synthetases when co-expressed in *E. coli*. In contrast, cells expressing combinations of synthetase and AE(GU) tRNA exhibited ampicillin $IC_{50}$ values 2-20-fold higher than those displayed by cells expressing AE(GU) alone (FIG. 3). The greatest $IC_{50}$ value differences were exhibited by cells co-expressing the AE(GU) tRNA together with MtERS (6 fold), AfERS (7 fold), PhERS (12 fold), and MmERS (20 fold). Cells co-expressing the best pair, MmERS and AE(GU), exhibited an $IC_{50}$ value of 100 μg/mL, a value still 4.5-fold lower than that displayed by the *M. jannaschii*-derived tyrosine pair (see, e.g., Wang, L., Brock, A., Herberich, B. and Schultz, P. G. (2001) *Expanding the genetic code of Escherichia coli. Science,* 292:498-500) and 10-fold lower than that displayed by the *M. thermoautotrophicum*-derived leucine pair (see, e.g., Anderson J C, & Schultz P G, (2003), *Adaptation of an orthogonal archaeal leucyl-tRNA and synthetase pair for four-base, amber, and opal suppression, Biochemistry*, August 19; 42(32):9598-9608). These results indicate that the AE(GU) tRNA combined with MtERS, AfERS, PhERS or MmERS constitute active but inefficient orthogonal pairs in *E. coli.*

Selection and characterization of an optimized consensus $tRNA^{Glu}$: In order to increase the efficiency of the archaeal glutamic acid orthogonal pairs, improved variants of the AE(GU) tRNA were sought. The presence of the non-canonical G10-U28 base pair was regarded as a possible explanation for the low amber-suppression efficiency exhibited by synthetase-AE(GU) pairs. An attempt to investigate the importance of this G-U base pair had already been made with the construction of the two $tRNA^{Gln}$-based consensus tRNAs, AQ(GU) and AQ(GC), which differed only with respect to this base pair. However, because both AQ(GU) and AQ(GC) lacked the ability to be aminoacylated by archaeal glutamyl-tRNA synthetases in *E. coli*, the importance of the G-U base pair was still unknown. To further address this issue, a small library of variants of the consensus $tRNA^{Glu}$, AE(GU), was constructed in which nucleotides in the 10 and 28 positions were randomized (FIG. 4, Panel A). This "AE(NN)" tRNA library was constructed by PCR using a degenerate oligonucleotide primer (see Materials and Methods), and inserted into the tRNA cloning site of plasmid pACKO-A184TAG, to afford the pAC-AE(NN) plasmid library. *E. coli* cells co-transformed with plasmid pKQ-MmERS and plasmid library pAC-AE(NN) were then plated on a series of LB agar plates containing varying concentrations of ampicillin. Bacterial colonies were observed on plates containing ampicillin concentrations as high as 500 μg/mL, indicating that at least one variant of the AE(GU) tRNA exhibited enhanced amber-suppression efficiency compared to the parent when co-expressed with MERS in *E. coli*. Ten bacterial colonies were picked from the 500-μg/mL ampicillin plate, and the pAC-AE(NN) plasmids were sequenced. All ten of the clones contained a G10-C28 base pair (FIG. 4, Panel B), indicating that this "AE(GC)" tRNA is the most active variant within the AE(NN) library.

To measure the amber suppression efficiency of the selected AE(GC) tRNA, *E. coli* cells carrying either pAC-AE (GC) alone or in combination with plasmid pKQ-AfERS, pKQ-MmERS, pKQ-MtERS, or pKQ-PhERS were plated on a series of LB agar plates containing varying concentrations of ampicillin. In all cases, *E. coli* cells co-expressing the AE(GC) tRNA were found to exhibit ampicillin $IC_{50}$ values 4-5-fold greater than those of cells co-expressing the AE(GU) tRNA (FIG. 4, Panel C). Cells co-expressing the MmERS and AE(GC) pair exhibited an ampicillin $IC_{50}$ value of 450 μg/mL, 4.5-fold greater than that displayed by cells co-expressing the MmERS and AE(GU) combination. Similarly, cells coexpressing the PhERS and AE(GC) pair exhibited an $IC_{50}$ value of 212 μg/mL, ~3.5-fold greater than those co-expressing PhERS and AE(GU). The ampicillin $IC_{50}$ value for cells expressing the AE(GC) tRNA alone also increased 4-fold relative to cells expressing the AE(GU) tRNA alone (20 μg/mL versus 5 μg/mL ampicillin), suggesting that the U28 to G replacement enhanced the overall amber suppression efficiency of the tRNA. Without being limited to one theory, such an enhancement may have resulted from improved *E. coli* processing of the AE(GC) tRNA compared to AE(GU) (see, e.g., Anderson J C, & Schultz P G, (2003), *Adaptation of an orthogonal archaeal leucyl-tRNA and synthetase pair for four-base, amber, and opal suppression, Biochemistry*, August 19; 42(32):9598-9608). Alternatively, the increased $IC_{50}$ value could be due to an increased rate of background aminoacylation of the AE(GC) tRNA compared to AE(GU).

Figure 5:
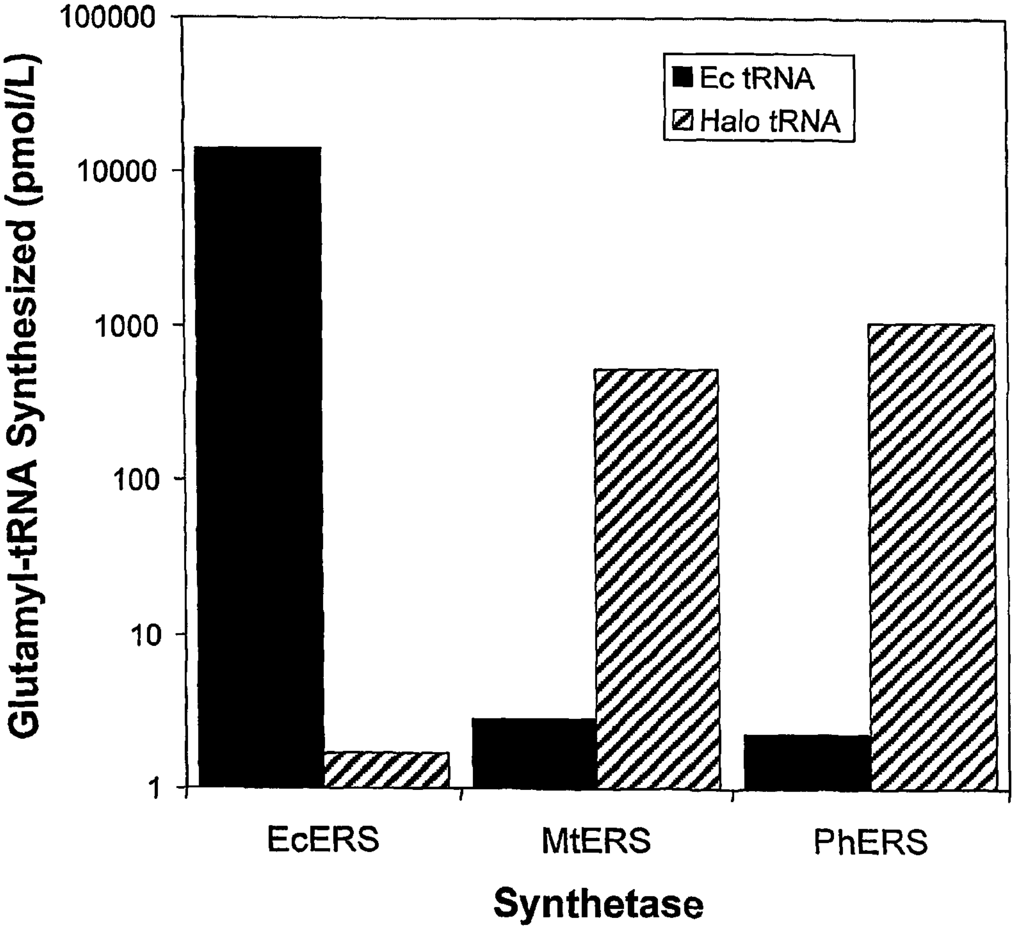
FIG. 5 provides a histogram demonstrating orthogonality of archaeal synthetases in vitro. For example, aminoacylation of whole tRNA from either *E. coli* (Ec) or *Halobacterium* sp. NRC-1 (halo) with [$^3$H]-glutamic acid is assayed in vitro.

Orthogonality of archaeal glutamyl-tRNA synthetases in *E. coli*: The ampicillin $IC_{50}$ measurements described above provide insights into the orthogonality of consensus-designed tRNAs, but provide no information about the orthogonality of archaeal glutamyl-tRNA synthetases in *E. coli*. To investigate synthetase orthogonality, the AfERS, MnERS, MtERS, and PhERS genes were inserted into a protein overexpression vector. *E. coli* glutamyl-tRNA synthetase (EcERS) was inserted into the same vector for use as a control. Synthetases were overexpressed in *E. coli*, purified to homogeneity, and used in an in vitro aminoacylation assay with whole tRNA prepared from either *E. coli* or the halophilic archaebacterium *Halobacterium* sp. NRC-1. As expected, EcERS robustly aminoacylated whole *E. coli* tRNA (14,000 pmol/L) and exhibited virtually no activity toward whole archaeal tRNA (1.7 pmol/L; FIG. 5). In contrast, none of the four archaeal synthetases exhibited measurable aminoacylation activity with whole *E. coli* tRNA (≦2.8 pmol/L), while two of the four synthetases actively aminoacylated whole archaeal tRNA (530 and 1100 pmol/L for MtERS and PhERS, respectively). In these experiments, it is unclear why AfERS and MmERS could not aminoacylate whole halobacterial tRNA in vitro (≦5 pmol/L). Without being limited to one theory, it is possible that the enzyme purification and/or assay conditions employed were deleterious to the aminoacylation activity of AfERS and MmERS. Another possibility is that subtle differences in tRNA identity elements might preclude recognition of a given archaeal $tRNA^{Glu}$ by all archaeal glutamyl-tRNA synthetases. To test the latter, the activity of MmERS was investigated using the in vitro aminoacylation assay with whole tRNA derived from *E. coli* expressing the AE(GC) tRNA. Again, no activity was observed, suggesting that the C-terminally His-tagged AfERS and MmERS enzymes are not active following purification. The above data demonstrate the orthogonality of MtERS and PhERS, and the likely orthogonality of AfERS and MmERS.

The consensus sequence strategy for the design of orthogonal tRNAs was successfully applied to the development of an orthogonal tRNA based on the family of $tRNA^{Glu}$ sequences from archaea. The initial candidate $tRNA^{Glu}$-based tRNA, AE(GU), was found to be highly orthogonal in *E. coli*, with cells expressing the tRNA alone displaying an ampicillin $IC_{50}$ value of just 5 μg/mL. However, the AE(GU) tRNA inefficiently suppressed amber codons when expressed in combination with archaeal glutamyl-tRNA synthetases in *E. coli*. Cells containing this synthetase-tRNA pair displayed an ampicillin $IC_{50}$ value of only 60 and 100 μg/mL for the two best synthetases, PhERS and MmERS, respectively. In order to improve the amber suppression efficiency of the AE(GU) tRNA, a small library of variants, randomized at the 10 and 28 positions, was constructed. Library members were selected for the ability to efficiently suppress an amber stop codon in *E. coli* when expressed in combination with MnERS. The resulting AE(GC) tRNA, when paired with PhERS and MmERS, suppress amber codons with high efficiency. Cells co-expressing this tRNA with PhERS and MmERS display ampicillin $IC_{50}$ values of 212 and 450 μg/mL, respectively.

An orthogonal tRNA based on the $tRNA^{Gln}$ family of sequences from the same organisms was not developed with the consensus sequence strategy. Without being limited to one theory, members of the family of archaeal $tRNA^{Gln}$ sequences, in general, deviate more from their consensus tRNA than do $tRNA^{Glu}$ sequences from theirs (Tables 1 and 2). This deviation suggests that individuals within the family of $tRNA^{Gln}$ may cluster less tightly in their evolutionary relatedness compared to tRNAs within the archaeal $tRNA^{Glu}$ family. Moreover, the degree of deviation within the $tRNA^{Gln}$ family may prevent individual synthetases from productively recognizing the consensus tRNA. A second possible explanation for the failure of the $tRNA^{Gln}$-based consensus design is that the AQ(GU) and AQ(GC) tRNAs may lack unknown elements that permit efficient processing in *E. coli*. *E. coli* cells expressing the AQ(GU) and AQ(GC) tRNAs without co-expressed archaeal glutamyl-tRNA synthetases exhibit relatively relatively high ampicillin $IC_{50}$ values compared to cells expressing the AE(GU) tRNA or no exogenous tRNA (FIG. 2). Without being limited to one theory, these data suggest that the AQ(GU) and AQ(GC) tRNAs are processed to at least some extent in *E. coli* and that their inability to be charged by archaeal glutamyl-tRNA synthetases in *E. coli* is due to the fact that they are not recognized as substrates.

The glutamyl-tRNA synthetase from *P. horikoshii* functions as part of an orthogonal tRNA synthetase and amber suppressor tRNA pair in *E. coli*. The development of this pair is a significant step in the process of incorporating unnatural amino acids into proteins in vivo. Synthetase variants can be evolved to selectively recognize unnatural amino acids and catalyze their condensation with the orthogonal AE(GC) tRNA. The evolved synthetases can then be used in unnatural amino acid mutagenesis of target proteins in *E. coli*.

Without being limited to one theory, it is likely that the amber suppression efficiency of the orthogonal synthetase and tRNA pair in *E. coli* is an important determinant of synthetase evolvability. Amber suppression efficiency, in turn, is determined by several kinetic parameters, including the rate of synthetase and tRNA production and processing in *E. coli* and the catalytic efficiency of tRNA aminoacylation. Altering the amino acid substrate specificity of a synthetase through the variation of active site residues likely reduces amber suppression efficiency by affecting either the $k_{cat}$ or $K_M$ of the variant enzyme (see, e.g., Wang, L., Brock, A., Herberich, B. and Schultz, P. G. (2001) *Expanding the genetic code of Escherichia coli. Science,* 292:498-500; and, Agou, F., Quevillon, S., Keijan, P. and Mirande, M. (1998) *Switching the amino acid specificity of an aminoacyl-tRNA synthetase. Biochemistry,* 11:11309-11314). Thus, the suppression efficiency of the parent synthetase-tRNA pair should be high enough to withstand a reduction in catalytic efficiency that can accompany protein evolution and allow the selection criteria to be met.

Amber suppression efficiencies can be determined by measurement of ampicillin $IC_{50}$ values for *E. coli* bearing a synthetase-tRNA pair. The only orthogonal synthetase that has been evolved to accept unnatural amino acids in *E. coli*, the tyrosyl-tRNA synthetase from *M. jannaschii*, exhibits an ampicillin $IC_{50}$ value of 440 μg/mL (see, e.g., Wang, L., Brock, A., Herberich, B. and Schultz, P. G. (2001) *Expanding the genetic code of Escherichia coli. Science,* 292:498-500). In contrast, the glutamine pair derived from *S. cerevisiae*, for which variants capable of accepting unnatural amino acids have not yet been found, displays an ampicillin $IC_{50}$ value of only 140 μg/mL (see, e.g., Pastrnak, M., Magliery, T. J. and Schultz, P. G. (2000) *A new orthogonal suppressor tRNA/aminoacyl-tRNA synthetase pair for evolving an organism with an expanded genetic code. Helvetica Chimica Acta,* 83:2277-2286). The difference in suppression efficiency between these two pairs may explain the apparent difference in the evolvability of their synthetases. On the basis of these data, PhERS, which, together with the AE(GC) tRNA, exhibits an amber suppression efficiency in *E. coli* ~2-fold less than that of the tyrosyl-tRNA synthetase, can be amenable to selection experiments to alter amino acid specificity. MmERS, which has an ampicillin $IC_{50}$ value roughly comparable to that of the tyrosyl-tRNA synthetase, can also be amenable to selection. Besides catalytic efficiency, however, other factors are likely to play a role in synthetase evolvability. The extensive hydrogen bonding network within the active site of the glutamine synthetase, for example, may affect the enzyme's evolvability. Our understanding of the relative importance of activity versus other, perhaps more subtle, features will improve our ability to generate and evolve additional orthogonal pairs.

The *M. jannaschii*-derived tyrosine orthogonal pair has been evolved to recognize a variety of unnatural amino acids containing aryl side chains. Efforts to develop variants of this synthetase that accept more diverse chemical structures are in progress. The availability of additional orthogonal pairs opens the possibility of expanding the diversity of unnatural amino acids that can be incorporated in, e.g., *E. coli*. The glutamic acid orthogonal pair described here, for example, can facilitate the development of synthetase variants that recognize negatively charged amino acids. This involves the generation of a large library of synthetase variants containing random amino acids substitutions at specific residues involved in binding the natural amino acid. Therefore, the availability of high-resolution structural information about the amino acid substrate-binding site is helpful for the directed evolution of a synthetase. Although the x-ray crystal structure of the glutamyl-tRNA synthetase from *M. mazei* has not yet been solved, the structure of the homologous enzyme from *Thermus thermophilus* is available (see, e.g., Nureki, O., Vassylyev, D. G., Katayanagi et al., (1995) *Architectures of class-defining and specific domains of glutamyl-tRNA synthetase. Science,* 31:1958-1965; and, Sekine et al., (2001) *Structural basis for anticodon recognition by discriminating glutamyl-tRNA synthetase. Nat. Struct. Biol.,* 8:203-206). This information is supplemented by co-crystal structural data of the glutaminyl-tRNA synthetase from *E. coli* with a glutaminyl-adenylate analog (see, e.g., Rath et al., (1998) *How glutaminyl-tRNA synthetase selects glutamine. Structure,* 6:439-449). Although they recognize somewhat different amino acid structures, the amino acid binding pockets of these enzymes are superimposable.

For many applications, the ability to incorporate multiple distinct unnatural amino acids into a protein in vivo is highly desirable. For example, the incorporation of two different fluorescent amino acids into a protein molecule would enable the use of fluorescence resonance energy transfer (FRET) for studying the conformational dynamics of proteins in vivo. The incorporation of two distinct unnatural amino acids into a protein requires the use of two mutually orthogonal synthetases that have been evolved to accept different unnatural amino acids. The development of an orthogonal glutamyl-tRNA synthetase and tRNA pair further advances the potential that multiple distinct unnatural amino acids can be incorporated into a single protein chain in living cells. Moreover, the archaeal species represent a rich source of orthogonal pairs for use in unnatural amino acid mutagenesis in, e.g., *E. coli*. These results provide insight into the rational design of efficiently-charged orthogonal tRNAs.

Example 2

Exemplary Glutamyl O-RSs and Glutamyl O-tRNAs

An exemplary O-tRNA comprises, e.g., SEQ ID NO.: 67 (and others herein) (See Table 3). Exemplary O-RSs include, e.g., SEQ ID NOs.: 69, 73, 75 and 77 (and others herein) (See Table 3). Exemplary polynucleotides that encode O-RSs or portions thereof include, e.g., SEQ ID NOs.: 68, 72, 74 and 76 (and others herein).

Further details of the invention, and in particular experimental details, can be found in Anderson, John Christopher, "Pathway Engineering of the Expanding Genetic Code," Ph.D. Dissertation, The Scripps Research Institute [2003].

It is understood that the examples and embodiments described herein are for illustrative purposes only and that various modifications or changes in light thereof will be suggested to persons skilled in the art and are to be included within the spirit and purview of this application and scope of the appended claims.

While the foregoing invention has been described in some detail for purposes of clarity and understanding, it will be clear to one skilled in the art from a reading of this disclosure that various changes in form and detail can be made without departing from the true scope of the invention. For example, all the techniques and apparatus described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

TABLE 3

SEQUENCES

| SEQ ID: | Label | SEQUENCE |
|---|---|---|
| SEQ ID: 1 | *Aeropyrum pernix* (CUC) Glutamic acid tRNA | GCCGCGGUAGUAUAGCCCGGCCCAGUAUGCGGGCCUCUCGAGCCC GUGACCCGGGUUCAAAUCCCGGCCGCGGCACCA |
| SEQ ID: 2 | *Aeropyrum pernix* (UUC) Glutamic acid tRNA | GCCGCGGUAGUAUAGCCCGGCCCAGUAUGCGGGCCUUUCGAGCCC GUGACCCGGGUUCAAAUCCCGGCCGCGGCACCA |
| SEQ ID: 3 | *Archaeo-globus fulgidus* (CUC) Glutamic acid tRNA | GCUCCGGUGGUGUAGCCCGGCCAAUCAUACGGGACUCUCGAUCCC GUGACCCGGGUUCAAAUCCCGGCCGGAGCACCA |
| SEQ ID: 4 | *Archaeo-globus fulgidus* (UUC) Glutamic acid tRNA | GCUCCGGUGGUGUAGCCCGGCCAAUCAUUCCGGCCUUUCGAGCCG GCGACCCGGGUUCAAAUCCCGGCCGGAGCACCA |
| SEQ ID: 5 | Halobac-terium sp. (CUC) Glutamic acid tRNA | GCUCCGUUGGUGUAGUCCGGCCAAUCAUCUUGCCCUCUCACGGCA AGGACUAGGGUUCAAAUCCCUGACGGAGCACCA |
| SEQ ID: 6 | Halobac-terium sp. (UUC) Glutamic acid tRNA | GCUCGGUUGGUGUAGUCCGGCCAAUCAUGUUGGCCUUUCGAGCCG ACGACCAGGGUUCAAAUCCCUGACCGAGCACCA |
| SEQ ID: 7 | Methano-bacterium *thermauto-trophicus* (UUC) Glutamic acid tRNA | GCUCCGGUAGUGUAGUCCGGCCAAUCAUUUCGGCCUUUCGAGCCG AAGACUCGGGUUCAAAUCCCGGCCGGAGCACCA |
| SEQ ID: 8 | *Methano-coccus jannaschii* (UUC) Glutamic acid tRNA | GCUCCGGUGGUGUAGUCCGGCCAAUCAUGCGGGCCUUUCGAGCCC GCGACCCGGGUUCAAAUCCCGGCCGGAGCACCA |
| SEQ ID: 9 | *Methano-coccus maripaludis* (UUC) Glutamic acid tRNA | GCUCCAGUGGUGUAGUCCGGCCAAUCAUCCGGCCCUUUCGAGGCC GGGACUCGGGUUCAAAUCCCGGCUGGAGCACCA |
| SEQ ID: 10 | *Methano-sarcina mazei* (CUC) Glutamic acid tRNA | GCUCCGAUAGUGUAGCUCGGCCAAUCAUUCAGGACUCUCACUCCU GCGACUGGGGUUCAAAUCCCCAUCGGAGCACCA |
| SEQ ID: 11 | *Methano-sarcina mazei* (UUC) Glutamic acid tRNA | GCUCCGGUAGUGUAGUCCGGCCAAUCAUUCCGGCCUUUCGAGCCG AAGACUCGGGUUCGAAUCCCGGCCGGAGCACCA |

TABLE 3-continued

| SEQ ID: | Label | SEQUENCE |
|---|---|---|
| | SEQUENCES | |
| SEQ ID: 12 | *Pyrobaculum aerophilum* (CUC) Glutamic acid tRNA | CAGCCGGUAGUCUAGCCCGGACAAGGAUGCGGGCCUCUCGAGCCC GUGACCCGGGUUCAAAUCCCGGCCGGGGCACCA |
| SEQ ID: 13 | *Pyrococcus abyssi* (CUC) Glutamic acid tRNA | GCCCCGGUGGUGUAGCCCGGUCAAUCAUGCGGGACUCUCGAUCCC GCGACCCGGGUUCAAAUCCCGGCCGGGGCACCA |
| SEQ ID: 14 | *Pyrococcus abyssi* (UUC) Glutamic acid tRNA | GCCCCGGUGGUGUAGCCCGGUCAAACAUGCGGGCCUUUCGAGCCC GCGCCCCGGGUUCAAAUCCCGGCCGGGGCACCA |
| SEQ ID: 15 | *Pyrococcus furiosus* (CUC) Glutamic acid tRNA | GCCCCGGUGGUGUAGCCCGGUCAAUCAUGCGGGACUCUCGAUCCC GCGACCCGGGUUCAAAUCCCGGCCGGGGCACCA |
| SEQ ID: 16 | *Pyrococcus furiosus* (UUC) Glutamic acid tRNA | GCCCCGGUGGUGUAGCCCGGUCAAACAUGCGGGCCUUUCGAGCCC GCGCCCCGGGUUCAAAUCCCGGCCGGGGCACCA |
| SEQ ID: 17 | *Pyrococcus horikoshii* (CUC) Glutamic acid tRNA | GCCCCGGUGGUGUAGCCCGGUCAAUCAUGCGGGACUCUCGAUCCC GCGACCCGGGUUCAAAUCCCGGCCGGGGCACCA |
| SEQ ID: 18 | *Pyrococcus horikoshii* (UUC) Glutamic acid tRNA | GCCCCGGUGGUGUAGCCCGGCCAAACAUGCGGGCCUUUCGAGCCC GCGCCCCGGGUUCAAAUCCCGGCCGGGGCACCA |
| SEQ ID: 19 | *Sulfolobus solfataricus* (CUC) Glutamic acid tRNA | GCCGCGGUGGUUUAGCCCGGUCAGAAUGCGGGCCUCUCGAGCCCG UGACCCGGGUUCAAAUCCCGGCCGCGGCACCA |
| SEQ ID: 20 | *Sulfolobus solfataricus* (UUC) Glutamic acid tRNA | GCCGCGGUGGUUUAGCCCGGUCAGAAUGCGGGCCUUUCGAGCCCG CCCGGGUUCAAAUCCCGGCUGACGCGGCACCA |
| SEQ ID: 21 | *Sulfolobus tokodaii* (CUC) Glutamic acid tRNA | GCCGCGGUAGUAUAGCCCGGUCAGUAUGCGGGCCUCUCAAGCCCG UGGCCCGGGUUCAAAUCCCGGCCGCGGCACCA |
| SEQ ID: 22 | *Sulfolobus tokodaii* (UUC) Glutamic acid tRNA | GCCGCGGUAGUAUAGCCCGGUCAAGCACGCGGGCCUUUCGAGCCC GUGACCCGGGUUCAAAUCCCGGCCGCGGCACCA |
| SEQ ID: 23 | Thermoplasma *acidophilum* (CUC) Glutamic acid tRNA | GCUCCGGUGGUGUAGUCCGGCCAAGCAUUAGGGACUCUCAAUCCC CCGACUCGGGUCCAAAUCCCGACCGGAGCACCA |

TABLE 3-continued

SEQUENCES

| SEQ ID: | Label | SEQUENCE |
|---|---|---|
| SEQ ID: 24 | Thermoplasma *acidophilum* (UUC) Glutamic acid tRNA | GCUCCGGUGGUGUAGUCCGGACAAGCAUAUCGGCCUUUCGAGCCG ACGACCUGGGUCCAAAUCCCGGCCGGAGCACCA |
| SEQ ID: 25 | Thermoplasma *volcanium* (CUC) Glutamic acid tRNA | GCUCCGGUGGUGUAGUCCGGCCAAGCAUUAGGGACUCUCAAUCCC CCGACUCGGGUCCAAAUCCCGACCGGAGCACCA |
| SEQ ID: 26 | Thermoplasma *volcanium* (UUC) Glutamic acid tRNA | GCUCCGGUGGUGUAGUCCGGACAAGCAUAUCGGCCUUUCGAGCCG ACGACCUGGGUCCAAAUCCCGGCCGGAGCACCA |
| SEQ ID: 27 | Consensus (YUC) Glutamic acid tRNA | GCYCCGGUGGUGUAGCCCGGCCAAKCAUGCGGGCCUYUCGAGCCC GCGACCCGGGUUCAAAUCCCGGCCGGRGCACCA |
| SEQ ID: 28 | AE (GU) (CUA) Glutamic acid tRNA | GCCCCGGUGGUGUAGCCCGGCCAAGCAUGCGGGCCUCUAAAGCCC GCGACCCGGGUUCAAAUCCCGGCCGGGGCACCA |
| SEQ ID: 29 | *Aeropyrum pernix* (CUG) Glutamine tRNA | AGCCGGGUCGUCUAGCGGCCCAGGAUGCGGGGCUCUGGCCCCCGU GACCGGGGUUCGAAUCCCCGCCCGGCUACCA |
| SEQ ID: 30 | *Aeropyrum pernix* (UUG) Glutamine tRNA | AGCCGGGUCGUCUAGCGGCCCAGGAUGCGGGGUUUUGGCCCCCGU GACCCGGGUUCGAAUCCCGGCCCGGCUACCA |
| SEQ ID: 31 | *Archaeo-globus fulgidus* (CUG) Glutamine tRNA | AGCCCCGUGGGGUAGCGGUCAAUCCUGCCGGACUCUGGAUCCGGC GACGCCGGUUCGAAUCCGGCCGGGGCUACCA |
| SEQ ID: 32 | *Archaeo-globus fulgidus* (UUG) Glutamine tRNA | AGCCCCGUGGUGUAGCGGUCAAUCAUGCGGGCCUUUGGAGCCCGC GACCGGGGUUCGAAUCCCCGCGGGGCUACCA |
| SEQ ID: 33 | Halobac-terium sp. (CUG) Glutamine tRNA | AGUCCCGUAGGGUAGUGGCCAAUCCUGAAGCCUUCUGGGGGCUUC GACGGAAGUUCGAAUCUUCCCGGGACUACCA |
| SEQ ID: 34 | Halobacter sp. (UUG) Glutamine tRNA | AGUCCCGUGGUGUAGUGGCCAAUCAUAUGGGCCUUUGGAGCCCAC GACGGCGGUUCGAAUCCGCCCGGGACUACCA |
| SEQ ID: 35 | Methano-bacterium *thermauto-trophicus* (CUG) Glutamine tRNA | AGUCCCGUGGGGUAAUGGCAAUCCUGAUGGACUCUGGAUCCAUCG AUAGCGGUUCGACUCCGCUCGGACUACCA |

TABLE 3-continued

SEQUENCES

| SEQ ID: | Label | SEQUENCE |
|---|---|---|
| SEQ ID: 36 | Methano-bacterium *thermauto-trophicus* (UUG) Glutamine tRNA | AGUCCCGUGGGGUAGUGGUAAUCCUGCUGGGCUUUGGACCCGGCG ACAGCGGUUCGACUCCGCUCGGGACUACCA |
| SEQ ID: 37 | *Methano-coccus jannaschii* (UUG) Glutamine tRNA | AGCCCGGUGGUGUAGUGGCCUAUCAUCCGGGGCUUUGGACCCCGG GACCGCGGUUCGAAUCCGCGCCGGGCUACCA |
| SEQ ID: 38 | *Methano-coccus maripaludis* (UUG) Glutamine tRNA | AGCCCAGUAGUGUAGUGGCCAAUCAUCCGUGCCUUUGGAGCAUGG GACCGCGGUUCGAAUCCGCGCUGGGCUACCA |
| SEQ ID: 39 | *Methanopyrus kandleri* (UUG) Glutamine tRNA | AGGGCCGUGGGGUAGCGGUCUAUCCUGCGGGGCUUUGGACCCCGC GACCCCGGUUCAAAUCCGGGCGGCCCUACCA |
| SEQ ID: 40 | *Methano-sarcina mazei* (CUG) Glutamine tRNA | AGCCCGGUAGUGUAGUGGUCAAUCAUGCGGGACUCUGGAUCCUGC AACCUCGGUUCGAAUCCGUGCCGGGCUACCA |
| SEQ ID: 41 | *Methano-sarcina mazei* (UUG) Glutamine tRNA | AGUCCUGUAGGGUAGUGGUCAAUCCUUCGGGCCUUUGGAGCCCGG GACAGCGGUUCGAAUCCGCUCAGGACUACCA |
| SEQ ID: 42 | *Pyrobaculum aerophilum* (CUG) Glutamine tRNA | AGCCCGGUCGUCUAGCGGCCAGGAUGCGGGGCUCUGGACCCCGUG GCCCGGGUUCGAAUCCCGGCCGGGCUACCA |
| SEQ ID: 43 | *Pyrobaculum aerophilum* (UUG) Glutamine tRNA | AGCCCGGUCGUCUAGCGGCCAAGGAUGCGGGGCUUUGGACCCCGU GGCCCGGGUUCGAAUCCCGGCCGGGCUACCA |
| SEQ ID: 44 | *Pyrococcus abyssi* (CUG) Glutamine tRNA | AGCCCCGUGGUGUAGCGGCCAAGCAUGCGGGACUCUGGAUCCCGC GACCGGGGUUCGAAUCCCCGCGGGGCUACCA |
| SEQ ID: 45 | *Pyrococcus abyssi* (UUG) Glutamine tRNA | AGCCCCGUGGUGUAGCGGCCAAGCAUGCGGGACUUUGGAUCCCGC GACCCGGGUUCGAAUCCCGGCGGGGCUACCA |
| SEQ ID: 46 | *Pyrococcus furiosus* (CUG) Glutamine tRNA | AGCCCCGUGGUGUAGCGGCCAAGCAUGCGGGACUCUGGAUCCCGC GACCGGGGUUCGAAUCCCCGCGGGGCUACCA |

TABLE 3-continued

SEQUENCES

| SEQ ID: | Label | SEQUENCE |
|---|---|---|
| SEQ ID: 47 | *Pyrococcus furiosus* (UUG) Glutamine tRNA | AGCCCCGUGGUGUAGCGGCCAAGCAUGCGGGACUUUGGAUCCCGC GACCCGGGUUCGAAUCCCGGCGGGGCUACCA |
| SEQ ID: 48 | *Pyrococcus horikoshii* (CUG) Glutamine tRNA | AGCCCCGUGGUGUAGCGGCCAAGCAUGCGGGACUCUGGAUCCCGC GACCGGGGUUCGAAUCCCCGCGGGGCUACCA |
| SEQ ID: 49 | *Pyrococcus horikoshii* (UUG) Glutamine tRNA | AGCCCCGUGGUGUAGCGGCCAAGCAUGCGGGACUUUGGAUCCCGC GACCCGGGUUCGAAUCCCGGCGGGGCUACCA |
| SEQ ID: 50 | *Sulfolobus solfataricus* (CUG) Glutamine tRNA | AGCCGGGUAGUCUAGUGGUCAAGGAUCCAGGGCUCUGGCCCCUGG GACCAGGGUUCGAAUCCCUGCCCGGCUACCA |
| SEQ ID: 51 | *Sulfolobus solfataricus* (UUG) Glutamine tRNA | AGCCGGGUAGUCUAGUGGUCAAGGAUCCAGGGCUUUGGCCCCUGG GACCAGGGUUCGAAUCCCUGCCCGGCUACCA |
| SEQ ID: 52 | *Sulfolobus tokodaii* (CUG) Glutamine tRNA | AGCCGGGUCGUCUAGUGGUCAAGGAUCGAGGGCUCUGGCCCCUCG GACCUGGGUUCAAAUCCCAGCCCGGCUACCA |
| SEQ ID: 53 | *Sulfolobus tokodaii* (UUG) Glutamine tRNA | AGCCGGGUCGUCUAGUGGUCAAGGAUCGAGGGCUUUGGCCCCUCG GACCUGGGUUCAAAUCCCAGCCCGGCUACCA |
| SEQ ID: 54 | Thermoplasma *acidophilum* (CUG) Glutamine tRNA | AGCCCUGUGGUGUAGUGGCCAAGCAUUAUGGGCUCUGGACCCAUC GACGGCAGUUCGAAUCUGCCCAGGGCUACCA |
| SEQ ID: 55 | Thermoplasma *acidophilum* (UUG) Glutamine tRNA | AGCCCUGUGGUGUAGUGGACAAGCAUUUUGGACUUUGGAUCCAAA GACGGCAGUUCGAAUCUGCCCAGGGCUACCA |
| SEQ ID: 56 | Thermoplasma *volcanium* (CUG) | AGCCCUGUGGUGUAGCGGCCAAGCAUUAUGGGCUCUGGACCCAUC GACGGCAGUUCGAAUCUGCCCAGGGCUACCA |
| SEQ ID: 57 | Thermoplasma *volcanium* (UUG) Glutamine tRNA | AGCCCUGUGGUGUAGUGGACAAGCAUUUUGGACUUUGGAUCCAAC GACGGCAGUUCGAAUCUGCCCAGGGCUACCA |
| SEQ ID: 58 | Consensus (YUG) Glutamine tRNA | AGCCCCGUGGUGUAGYGGCCAAGCAUGCGGGRCUYUGGAYCCCGC GACCGSGGUUCGAAUCCSCGCGGGGCUACCA |
| SEQ ID: 59 | AQ (GU) (CUA) Glutamine tRNA | AGCCCCGUGGUGUAGCGGCCAAGCAUGCGGGGCUCUAAACCCCGC GACCGGGGUUCGAAUCCCCGCGGGGCUACCA |

TABLE 3-continued

SEQUENCES

| SEQ ID: | Label | SEQUENCE |
|---|---|---|
| SEQ ID: 60 | AQ (GC) (CUA) Glutamine tRNA | AGCCCCGUGGUGUAGCGGCCAAGCACGCGGGGCUCUAAACCCCGC<br>GACCGGGGUUCGAAUCCCCGCGGGGCUACCA |
| SEQ ID: 61 | Glu consensus tRNA | GCYCCGGUGGUGUAGCCCGGCCAAKCAUGCGGGCCUYUCGAGCCC<br>GCGACCCGGGUUCAAAUCCCGGCCGGRGCACCA |
| SEQ ID: 62 | Gln consensus tRNA | AGCCCCGUGGUGUAGYGGCCAAGCAUGCGGGRCUYUGGAYCCCGC<br>GACCGSGGUUCGAAUCCSCGCGGGGCUACCA |
| SEQ ID: 63 | AE (GU) tRNA | GCCCCGGUGGUGUAGCCCGGCCAAGCAUGCGGGCCUCUAAAGCCC<br>GCGACCCGGGUUCAAAUCCCGGCCGGGGCACCA |
| SEQ ID: 64 | AQ (GU) tRNA | AGCCCCGUGGUGUAGCGGCCAAGCAUGCGGGGCUCUAAACCCCGC<br>GACCGGGGUUCGAAUCCCCGCGGGGCUACCA |
| SEQ ID: 65 | AQ (GC) tRNA | AGCCCCGUGGUGUAGCGGCCAAGCACGCGGGGCUCUAAACCCCGC<br>GACCGGGGUUCGAAUCCCCGCGGGGCUACCA |
| SEQ ID: 66 | AE (NN) tRNA library | GCCCCGGUGNUGUAGCCCGGCCAAGCANGCGGGCCUCUAAAGCCC<br>GCGACCCGGGUUCAAAUCCCGGCCGGGGCACCA |
| SEQ ID: 67 | AE (GC) tRNA | GCCCCGGUGGUGUAGCCCGGCCAAGCACGCGGGCCUCUAAAGCCC<br>GCGACCCGGGUUCAAAUCCCGGCCGGGGCACCA |
| SEQ ID: 68 | AfERS | gtgaaagaag tcataatgaa atacgtagtt cagaacgccg caaagtacgg<br>aaaagccagt gaaaaggctg taatggggaa ggtgatggca gaaaatccag<br>aactcagaaa aaaagctaaa gaggtccttg aactcgtaaa ggagtgcatt<br>accgagttcg aagcgctttc tgaagaagta aggaaggagc taatcaaaaa<br>atacagcatg gatagcgaag ctaaaaggga gttggagacg aagaagcttc<br>cagagcttga gggggctgag aaagggaaag ttgtgatgag attcgctcct<br>aatccaaacg gtccacctac actcggttct gctaggggga taatcgtcaa<br>cggtgaatac gcgaagatgt acgaagggaa gtacattatc aggtttgacg<br>atacagaccc cagaaccaag agaccgatga ttgaggccta cgagtggtac<br>ctagaggaca ttgaatggct cggttacaag cctgacgagg ttatttacgc<br>ctcaagaagg attcccatct actacgatta tgcaagaaag cttatagaaa<br>tgggcaaagc ctacacctgc ttctgcagtc aggaggagtt caagaagttc<br>agggacagtg gtgaggagtg cccacacaga aacatcagcg tcgaggatac<br>acttgaagtc tgggagagaa tgcttgaagg agactatgag gaaggagaag<br>tcgttcttag aattaagacg gatatgcgcc acaaggatcc ggcaataagg<br>gactgggtgg ctttcaggat aataaaggaa tcacatcctc tcgttgggga<br>taaatatgtt gtctatccca cactcgattt tgaatctgct atagaggatc<br>accttttagg cataacgcac attatcaggg gtaaggactt aattgattct<br>gagaggaggc agagatacat ctacgagtat tttggctgga tttaccccat<br>tacaaagcac tggggcaggg ttaaaatctt cgaattcggg aagctatcga<br>cttcttcaat taagaaggat attgaaaggg gtaagtatga gggctgggat<br>gacccaaggc tgccaacctt gagagccttc aggaggagag gatttgagcc<br>tgaagccata aagagcttct tcctttcgct gggagttggc gagaacgacg<br>tttccgtcag tctcaagaat ctttacgctg agaacaggaa aatcatcgat<br>cgcaaggcaa accgttactt tttcatttgg gggcccgtga agattgaaat<br>cgttaacctg ccggagaaga aagaggtcga gctcccgctg aatccgcaca<br>cgggcgagaa gagaaggctg aaaggtgaaa gaactatata tgttacaaaa<br>gacgacttcg agaggttgaa agggcaggtt gtaaggctga aggacttctg<br>caacgttctg cttgacgaga aggcagagtt catgggtttt gagcttgagg<br>gggtcaagaa ggggaagaac ataatccact ggcttcctga gagcgaggct<br>atcaagggca aggttatcgg cgaaagggaa gcggaagggc ttgtggagag<br>aaacgcagtt agagatgtcg ggaaagtcgt gcagttcgag agatttgctt<br>tctgtaaagt agagtctgct gacgaggaac tggtcgcggt gtacacgcac<br>ccgtga |
| SEQ ID: 69 | AfERS.pep | VKEVIMKYVV QNAAKYGKAS EKAVMGKVMA ENPELRKKAK EVLELVKECI<br>TEFEALSEEV RKELIKKYSM DSEAKRELET KKLPELEGAE KGKVVMRFAP<br>NPNGPPTLGS ARGIIVNGEY AKMYEGKYII RFDDTDPRTK RPMIEAYEWY<br>LEDIEWLGYK PDEVIYASRR IPIYYDYARK LIEMGKAYTC FCSQEEFKKF<br>RDSGEECPHR NISVEDTLEV WERMLEGDYE EGEVVLRIKT DMRHKDPAIR<br>DWVAFRIIKE SHPLVGDKYV VYPTLDFESA IEDHLLGITH IIRGKDLIDS<br>ERRQRYIYEY FGWIYPITKH WGRVKIFEFG KLSTSSIKKD IERGKYEGWD<br>DPRLPTLRAF RRRGFEPEAI KSFFLSLGVG ENDVSVSLKN LYAENRKIID<br>RKANRYFFIW GPVKIEIVNL PEKKEVELPL NPHTGEKRRL KGERTIYVTK |

TABLE 3-continued

SEQUENCES

| SEQ ID: | Label | SEQUENCE |
|---|---|---|
| | | DDFERLKGQV VRLKDFCNVL LDEKAEFMGF ELEGVKKGKN IIHWLPESEA<br>IKGKVIGERE AEGLVERNAV RDVGKVVQFE RFAFCKVESA DEELVAVYTH<br>P* |
| SEQ ID: 70 | ApERS | atgtcaatgc tcctagggga ccatcctgag cttaggagta gggcgaggga<br>gatagcctcc ctggctgcaa gggtcgtgga gcaggtgaac agcatgcctg<br>ctggcgagca gaagaggctc ctctcagaac agtatccgga gctagcgagg<br>tttgaagagc agcgcgagaa aggcgataaa ggcctacccc cgctgcccgg<br>ggccgtggaa ggcagggtca agctgaggtt cgcccccaac ccagactttg<br>tgatacacat gggcaacgct aggccggcca tagtgaacca cgagtacgcc<br>aggatgtata aggggaggat ggtgctgcgg ttcgaagaca cagaccctag<br>gacaaagact cccctacggg aggcgtacga cctcatccgc caggacctca<br>agtggcttgg cgtttcctgg gacgaggagt acatccagag cctcaggatg<br>gaggtcttct acagcgtagc cagaagggct atagagcggg ggtgcgccta<br>cgtcgacaac tgtgggagag agggtaagga gctgctctcg cgtggagagt<br>attgtccgac cagggatctt ggccccgagg ataatctgga gctgtttgag<br>aagatgcttg aaggagagtt ttacgagggg gaggctgttg tgaggatgaa<br>gacggacccg cgccacccca accccagcct gagggactgg gtggccatga<br>ggattataga cacggagaaa cacccccacc ccctcgtggg gagcaggtac<br>ctggtgtggc cgacctataa cttcgccgtc agcgtcgacg accacatgat<br>ggagataacc cacgtgctca ggggtaagga gcaccagctg aacaccgaga<br>agcagcttgc cgtctacagg tgtatgggct ggaggccgcc gtacttcatc<br>cacttcggca ggctaaagct ggaggggttt atactgagca agagcaagat<br>aagaaagctc ctcgaagaga ggccaggaga gttcatgggc tacgacgacc<br>cccgcttcgg cacgatagcc gggctgagga ggaggggtgt gctggcggag<br>gccataagac agataatact cgaggtgggg gtcaagccca cggacgctac<br>aataagctgg gcaaacctgg cggccgctaa taggaagctg ctggacgagc<br>gggcggacag gataatgtat gtcgaagacc ccgttgagat ggaggtcgag<br>ctggcccagg tggagtgcag agccgcggag ataccgttcc acccgagccg<br>cccccagagg aagaggagga taaccttgtg cacgggggac aaggttctcc<br>tcacaaggga ggacgcagta gagggtaggc aactgaggct catgggccta<br>tcaaacttca ccgtcagcca aggcatattg agggaggtgg atcccagcct<br>cgagtatgcg aggagaatga agctacctat agtacaatgg gtgaagaagg<br>gcggagaagc tagcgtagag gtactcgagc ccgtcgagct ggagctcagg<br>aggcaccagg gctacgctga ggacgctatt aggggctatg ggttgacag<br>ccgcctacag tttgtaaggt acggttttgt gagggtggac agcgtggaag<br>acggggtcta cagggtgata tacacacaca agtag |
| SEQ ID: 71 | ApERS.pep | MSMLLGDHPE LRSRAREIAS LAARVVEQVN SMPAGEQKRL LSEQYPELAR<br>FEEQREKGDK GLPPLPGAVE GRVKLRFAPN PDFVIHMGNA RPAIVNHEYA<br>RMYKGRMVLR FEDTDPRTKT PLREAYDLIR QDLKWLGVSW DEEYIQSLRM<br>EVFYSVARRA IERGCAYVDN CGREGKELLS RGEYCPTRDL GPEDNLELFE<br>KMLEGEFYEG EAVVRMKTDP RHPNPSLRDW VAMRIIDTEK HPHPLVGSRY<br>LVWPTYNFAV SVDDHMMEIT HVLRGKEHQL NTEKQLAVYR CMGWRPPYFI<br>HFGRLKLEGF ILSKSKIRKL LEERPGEFMG YDDPRFGTIA GLRRRGVLAE<br>AIRQIILEVG VKPTDATISW ANLAAANRKL LDERADRIMY VEDPVEMEVE<br>LAQVECRAAE IPFHPSRPQR KRRITLCTGD KVLLTREDAV EGRQLRLMGL<br>SNFTVSQGIL REVDPSLEYA RRMKLPIVQW VKKGGEASVE VLEPVELELR<br>RHQGYAEDAI RGYGVDSRLQ FVRYGFVRVD SVEDGVYRVI YTHK* |
| SEQ ID: 72 | MmERS | atgaccttaa gtcctgaaga tattaaaata attgaaaaat acgctcttca<br>aaatgctgta aaatacggaa aagccccaca gcccaaagct gttatgggta<br>aagttatggg ggaatgtccc cagttgaggg ctgaccccag cggggtatct<br>gctgcccttg aaaatatagt ttcagaaatt gctaaaggaa accctgaagc<br>ctgggaagcc cgcctgtcgg aaatcgctcc cgagcttata gaggctctga<br>gtgtaaagaa agagcctgac aaaggcttaa aacctcttga gggagccgaa<br>accggtaagg ttgtaatgcg ctttgcccca aatcccaacg gacccgcaac<br>cctgggaagt tcaaggggaa tggttgtcaa ttccgagtat gtaaaagtgt<br>ataaaggaaa gtttatcctg cgctttgatg acactgaccc tgatataaag<br>cgtcccatgc tcgaagccta tgactggtac atggacgact ttaaatggct<br>cggggttgtg cctgaccagg ttgtacgtgc ctctgaccgt ttcccgattt<br>attacgatta tgcaagaaaa ctgattgaga tgggaaaagc ctatgtctgt<br>ttctgtaaag gagaagactt caaaaggtta aaagactcca aaaaggcctg<br>ccctcacagg gacacagacc ctgaagaaaa ccttatgcac tgggaaaaga<br>tgcttgccgg agaatatgaa gaccagcagg ctgttctgcg cataaagacc<br>gatatagagc acaaagaccc tgcacttcgg gactggggag cattcaggat<br>tagaaaaatg tcccacccac gccctgagat tggaaataaa tacatcgtct<br>ggcccccttct ggactttgca ggtgctatcg aagaccacga gctcggtatg<br>acccacatca tccggggtaa agaccttatc gacagtgaaa aacggcagac<br>atacatttac aaatacttcg gctggacata cccgaaaaca actcactggg<br>gcagggtaaa gatccatgag ttcggaaagt tcagcacaag taccctgcgt<br>aaagctatcg aatccggaga atacagcggc tgggacgacc cccgcctgcc<br>gacaataagg gcaatcaggc gccgtggaat tagggctgaa gctctcaaaa<br>agttcatgat agaaatggga gtcgggatga ccgatgtgag catcagcatg<br>gaatctcttt atgccgagaa ccgcaaaatc gtggacccgg ttgcaaaccg |

TABLE 3-continued

SEQUENCES

| SEQ ID: | Label | SEQUENCE |
|---|---|---|
| | | ctatttcttt gtctggaacc ctgtggagct tgaaattgaa ggtatgaaac ctgtggtcgc aaaggtcccc cgtcacccaa cagaccatgc aagaggaatg agggaaatct ctatcgaaaa taaggttctt gtctgtgccg aggacattga aaagctcaat gtaggttctg tcctccgctt aaaagatctc tgcaacgttg aaattacttc cctttccccg ctgcgggtta agcgctccga aacctctctc gaagacctca aaaaagcaaa aggaaaaatc atccactggg tgccggttga tggaattcct gtgaaagtct gcgggccaga gggcgatatc gaagggacag gagaacgcgg gatcgagacc gagcttgata atattgtcca gtttgaacgc ttcggtttct gcaggatcga cgccgtagac ggagaaaatg tcgtggcgta ctttgctcac aaatga |
| SEQ ID: 73 | MmERS.pep | MTLSPEDIKI IEKYALQNAV KYGKAPQPKA VMGKVMGECP QLRADPSGVS AALENIVSEI AKGNPEAWEA RLSEIAPELI EALSVKKEPD KGLKPLEGAE TGKVVMRFAP NPNGPATLGS SRGMVVNSEY VKVYKGKFIL RFDDTDPDIK RPMLEAYDWY MDDFKWLGVV PDQVVRASDR FPIYYDYARK LIEMGKAYVC FCKGEDFKRL KDSKKACPHR DTDPEENLMH WEKMLAGEYE DQQAVLRIKT DIEHKDPALR DWGAFRIRKM SHPRPEIGNK YIVWPLLDFA GAIEDHELGM THIIRGKDLI DSEKRQTYIY KYFGWTYPKT THWGRVKIHE FGKFSTSTLR KAIESGEYSG WDDPRLPTIR AIRRRGIRAE ALKKFMIEMG VGMTDVSISM ESLYAENRKI VDPVANRYFF VWNPVELEIE GMKPVVAKVP RHPTDHARGM REISIENKVL VCAEDIEKLN VGSVLRLKDL CNVEITSLSP LRVKRSETSL EDLKKAKGKI IHWVPVDGIP VKVCGPEGDI EGTGERGIET ELDNIVQFER FGFCRIDAVD GENVVAYFAH K* |
| SEQ ID: 74 | MtERS | gtggtgccag tggaggacct tgtctacagg tacgcactcc tgaacgctgt gaaacacagg ggaagggcaa acccgggggc cgtcatgggg gccgtcatga gcaacgaacc tgaactcagg aagatggcgc cccaggttaa ggaagcagtt gaggccgctg ttgagagggt taacagttta agccccgagg agcagcagca ggagatggag aggctgggcc ttgagatcac cgagaggaaa cagaagaagc ggaagggtct aagggaactg gccggggtga agggtgaggt ggtcctcagg ttcgccccca accccagcgg acccctccac ataggccatg caagggccgc gatcctcaac catgaatatg caaggaaata tgacggcagg ctcatcctca ggatagagga cacggacccc cgcagggttg acccggaggc ctacgatatg attccagccg accttgagtg gctgggcgtt gaatgggatg agacagttat ccagagcgac cgcatggaaa cctactatga gtacacagag aaactcatag agaggggtgg tgcgtatgta tgcacatgca ggccggagga gttcagggaa ctcaagaaca ggggagaggc ctgtcactgc aggtcccttg gtttcaggga gaacctccag cgatggaggg aaatgttcga gatgaaggag ggctcagccg ttgtgagggt taaaacggac ctgaaccacc caaaccctgc cataagagac tgggtctcaa tgaggatcgt tgaggcagag cacccacgca ccggtacacg ctacagggtc taccccatga tgaacttctc agtggcggtt gatgaccacc tccttggcgt gacacacgtc ctgaggggta aggaccacct ggcaaacaga gagaagcagg agtacctcta caggcacctt ggctgggagc cccccgaatt catacactac gggcgcctga agatggacga cgttgcactc agcacctcgg gggcccgtga gggcatcctc aggggtgagt attctggatg ggacgaccca cgcctcggaa ccctgagggc cattgcaagg aggggtatac gaccggaggc cataagaaag ttaatggttg aaatcggcgt aaagatagca gattccacaa tgagctggaa gaagatctac ggcctcaaca ggagcatcct cgaagaggag gccaggaggt acttctttgc tgcagatcct gttaaacttg aagtggtggg tttacccgga cctgtcaggg ttgaaaggcc cctacacccg gaccaccctg aaatcgggaa cagggtactt gaactgaggg gtgaggtgta cctgccgggc gatgaccttg gggaaggacc gctgcgcctc atagacgcgg ttaacgtgat ctactctggg ggtgaactga ggtaccacag tgagggcatc gaggaggccc gtgaactcgg cgcttcaatg atacactggg tccctgcaga gtccgccctt gaggccgagg tcatcatgcc ggacgcctcc agggtgaggg gagtcatcga ggctgacgca tcagaactgg aggttgatga tgttgtgcag cttgagaggt tcggcttcgc ccgcctggat tctgcaggcc caggaatggt cttctactat gcccacaaat ga |
| SEQ ID: 75 | MtERS.pep | VVPVEDLVYR YALLNAVKHR GRANPGAVMG AVMSNEPELR KMAPQVKEAV EAAVERVNSL SPEEQQQEME RLGLEITERK QKKRKGLREL AGVKGEVVLR FAPNPSGPLH IGHARAAILN HEYARKYDGR LILRIEDTDP RRVDPEAYDM IPADLEWLGV EWDETVIQSD RMETYYEYTE KLIERGGAYV CTCRPEEFRE LKNRGEACHC RSLGFRENLQ RWREMFEMKE GSAVVRVKTD LNHPNPAIRD WVSMRIVEAE HPRTGTRYRV YPMMNFSVAV DDHLLGVTHV LRGKDHLANR EKQEYLYRHL GWEPPEFIHY GRLKMDDVAL STSGAREGIL RGEYSGWDDP RLGTLRAIAR RGIRPEAIRK LMVEIGVKIA DSTMSWKKIY GLNRSILEEE ARRYFFAADP VKLEVVGLPG PVRVERPLHP DHPEIGNRVL ELRGEVYLPG DDLGEGPLRL IDAVNVIYSG GELRYHSEGI EEARELGASM IHWVPAESAL EAEVIMPDAS RVRGVIEADA SELEVDDVVQ LERFGFARLD SAGPGMVFYY AHK* |
| SEQ ID: 76 | PhERS | atggatgtgg aaaagatagc tctcaaacat gcccttatta atgcaattga gcatggaggt aaggctaatc ttaaggccgt catcggtaaa gtgctcggcg agaaccctga gcttaggccc agggccaagg agataattcc cataattaat |

TABLE 3-continued

SEQUENCES

| SEQ ID: | Label | SEQUENCE |
|---|---|---|
| | | aaggtagtgg aagaggtcaa ctcactagca agggatgagc agctggaaaa<br>gcttaaggat atatatccag agtactttga aaagaaggaa gagaagaagg<br>aaaagaaggg actacctctt cttcctaaag cagagaaagg caaggtcgtt<br>actcgctttg ctccaaatcc agatggtgct tttcacctgg gtaatgcaag<br>ggccgcaata cttagttatg aatacgccaa gatgtacggt gggaagttta<br>tactccgctt tgatgatacc gatccaaaag tcaagaggcc tgaacccata<br>ttctacaaga tgataattga agatctagag tggcttggaa taaagccaga<br>tgaaatagtg tacgctagtg atagactcga aatttactac aagtacgctg<br>aggaactaat aaaaatgggt aaagcatatg tctgcacttg tcctccagag<br>aagttcagag agcttagaga taagggaatt ccatgtccgc atagagatga<br>gcctgtggaa gttcagctcg agcgctggaa gaagatgtta aacggcgaat<br>ataaagaagg agaagctgtt gtaaggataa agactgactt aaatcaccca<br>aatcctgcgg ttagggattg gcccgcactt agaataattg ataacccaaa<br>ccatccgaga accggaaata agtacagggt atggcctctc tacaattttg<br>cctcagcgat tgatgatcac gagcttggag ttacccatat cttccgtgga<br>caggagcacg ccgagaacga gactagacag aggtatatct acgagtactt<br>tggttgggag tatcccgtca cgatccatca cgggaggctt agcatagagg<br>gagttgtttt aagcaaatcc aagacaagga aaggaataga agaaggtaag<br>tatctcggtt gggatgatcc taggcttgga acgataagag ctttgaggag<br>gaggggaatt cttcctgaag ccataaaaga attgatcata gaagttggat<br>tgaagaaaag tgacgcgacg atcagttggg agaatctggc agcgataaac<br>agaaaacttg ttgatccaat tgccaataga tatttctttg ttgcagatcc<br>aattccgatg gaagtcgaag gggctcctga atttatagca gagataccgc<br>ttcatcctga ccatcctgaa aggggcgtta gaaggcttaa gttcactcca<br>gaaagacctg tttacgtttc gaaagacgat ttgaatctct taaaaccagg<br>caattttgtg aggttaaagg atctcttcaa tgttgaaata cttgaagttg<br>gagacaaaat aagagctagg ttctacagct ttgaatatga aattgcaaag<br>aagaacaggt ggaagatggt tcactgggtt accgaaggta gaccctgtga<br>ggttataatt cctgaaggag acgagcttgt agtgaggaag ggattgctcg<br>agaaggatgc caaagttcaa gttaacgaaa tagtccagtt tgaacgtttc<br>ggttttgtaa ggatagacag aattgagggg gataaagtta tcgcaatata<br>tgctcacaag taa |
| SEQ ID: 77 | PhERS.pep | MDVEKIALKH ALINAIEHGG KANLKAVIGK VLGENPELRP RAKEIIPIIN<br>KVVEEVNSLA RDEQLEKLKD IYPEYFEKKE EKKEKKGLPL LPKAEKGKVV<br>TRFAPNPDGA FHLGNARAAI LSYEYAKMYG GKFILRFDDT DPKVKRPEPI<br>FYKMIIEDLE WLGIKPDEIV YASDRLEIYY KYAEELIKMG KAYVCTCPPE<br>KFRELRDKGI PCPHRDEPVE VQLERWKKML NGEYKEGEAV VRIKTDLNHP<br>NPAVRDWPAL RIIDNPNHPR TGNKYRVWPL YNFASAIDDH ELGVTHIFRG<br>QEHAENETRQ RYIYEYFGWE YPVTIHHGRL SIEGVVLSKS KTRKGIEEGK<br>YLGWDDPRLG TIRALRRRGI LPEAIKELII EVGLKKSDAT ISWENLAAIN<br>RKLVDPIANR YFFVADPIPM EVEGAPEFIA EIPLHPDHPE RGVRRLKFTP<br>ERPVYVSKDD LNLLKPGNFV RLKDLFNVEI LEVGDKIRAR FYSFEYEIAK<br>KNRWKMVHWV TEGRPCEVII PEGDELVVRK GLLEKDAKVQ VNEIVQFERF<br>GFVRIDRIEG DKVIAIYAHK * |
| SEQ ID: 78 | SsERS | ttgatggaat taaatgaatt acgagaaact atttataaat atgctcttca<br>aaatgcggta aagcataatg ggaaagccga aacgggtcca gtgatgagta<br>agattatagc ggagaggccg gaattaagat caaatgctag agaaattgta<br>aagattatca aggagatcat agaacaagtt aactcattaa ctttagagca<br>gcagttaact gaaattaaag caaagtatcc agagttatta gaagagaaga<br>agcatgaaga aaaaagaaaa gtgttgccac ctcttcctaa tgttaaagga<br>caagtagtaa ctagatttgc ccctaatccg gatggtcctc ttcatttagg<br>taacgcaagg tctgcgattc tatcttacga atacgctaaa atgtataacg<br>gtaagttcat actgaggttt gatgatacag atcctaaggt taaaaggcca<br>attctagatg catatgattg gattaaggag gatctaaaat ggctgggaat<br>taaatgggaa caagaacttt acgcttcgga aaggctcgag ttatactata<br>agtacgctcg gtatttgata gaaaaaggat atgcgtatgt tgatacatgt<br>gatagtagta ttttcaggaa gtttagggat agtagaggta aaatgaaaga<br>gccagaatgt ttacatagga gctcttcacc agagagtaat ctggagctgt<br>ttgaaaaaat gctaggagga aagtttaaag aaggagaagc tgtggttagg<br>ttaaagaccg atctatcgga tccagatcca tctcaaatag attgggtaat<br>gcttagaata attgatactg ctaaaaatcc tcatccacga gtagggagca<br>agtattgggt atggcctacc tataactttg cttctataat agatgatcat<br>gaacttggaa ttactcatgt actgagagct aaggagcata tgtcaaatac<br>agaaaagcag agatacattt ctgagtacat gggatgggaa tttccagagg<br>tcttacagtt tggaagacta agacttgaag gttttatgat gagtaagtcg<br>aaaataagag gaatgttaga gaagggtacc aatagggatg atcctagatt<br>gccaacttta gctggactca gaagaagagg aatcttacca gatacaatta<br>aagacgtaat aattgatgtc ggagtaaagg taactgatgc tactataagt<br>tttgagaaca ttgccgcaat taataggaaa aaactagatc cggtagctaa<br>aagaataatg tttgtaaaag atgcagaaga atttagcgtc gagctacctg<br>aatcactaaa tgctaaaata cctttaattc cctctaaaca agaaatgaat<br>agaactatta ttgtcaatcc aggagataaa attttgatag aatctaacga<br>tgcagaagat aatagtatac taaggttaat ggaattatgc aatgttaaag |

TABLE 3-continued

SEQUENCES

| SEQ ID: | Label | SEQUENCE |
|---|---|---|
| | | ttgataagca taatcgtaag ctcatatttc acagcaaaac gttagacgag |
| | | gctaagaaag tcaatgcaaa gatagttcaa tgggtaaaat caaatgaaaa |
| | | agtaccagta atggtagaga aagcggaaag agatgagata aaaatgataa |
| | | atggttatgc tgaaaaaata gcagcagatt tggagataga cgaaattgta |
| | | caattttacc gatttggatt tgtaagagta gataggaaag atgagaatat |
| | | gctacgtgtt gtattctcac acgactga |
| SEQ ID: 79 | SsERS.pep | LMELNELRET IYKYALQNAV KHNGKAETGP VMSKIIAERP ELRSNAREIV |
| | | KIIKEIIEQV NSLTLEQQLT EIKAKYPELL EEKKHEEKRK VLPPLPNVKG |
| | | QVVTRFAPNP DGPLHLGNAR SAILSYEYAK MYNGKFILRF DDTDPKVKRP |
| | | ILDAYDWIKE DLKWLGIKWE QELYASERLE LYYKYARYLI EKGYAYVDTC |
| | | DSSIFRKFRD SRGKMKEPEC LHRSSSPESN LELFEKMLGG KFKEGEAVVR |
| | | LKTDLSDPDP SQIDWVMLRI IDTAKNPHPR VGSKYWVWPT YNFASIIDDH |
| | | ELGITHVLRA KEHMSNTEKQ RYISEYMGWE FPEVLQFGRL RLEGFMMSKS |
| | | KIRGMLEKGT NRDDPRLPTL AGLRRRGILP DTIKDVIIDV GVKVTDATIS |
| | | FENIAAINRK KLDPVAKRIM FVKDAEEFSV ELPESLNAKI PLIPSKQEMN |
| | | RTIIVNPGDK ILIESNDAED NSILRLMELC NVKVDKHNRK LIFHSKTLDE |
| | | AKKVNAKIVQ WVKSNEKVPV MVEKAERDEI KMINGYAEKI AADLEIDEIV |
| | | QFYRFGFVRV DRKDENMLRV VFSHD* |
| SEQ ID: 80 | pACKO-A184TAG | gaactccgga tgagcattca tcaggcgggc aagaatgtga ataaaggccg |
| | | gataaaactt gtgcttattt ttctttacgg tctttaaaaa ggccgtaata |
| | | tccagctgaa cggtctggtt ataggtacat tgagcaactg actgaaatgc |
| | | ctcaaaatgt tctttacgat gccattggga tatatcaacg gtggtatatc |
| | | cagtgatttt tttctccatt ttagcttcct tagctcctga aaatctcgat |
| | | aactcaaaaa atacgcccgg tagtgatctt atttcattat ggtgaaagtt |
| | | ggaacctctt acgtgccgat caacgtctca ttttcgccaa aagttggccc |
| | | agggcttccc ggtatcaaca gggacaccag gatttattta ttctgcgaag |
| | | tgatcttccg tcacaggtat ttattcggcg caaagtgcgt cgggtgatgc |
| | | tgccaactta ctgatttagt gtatgatggt gtttttgagg tgctccagtg |
| | | gcttctgttt ctatcagctg tccctcctgt tcagctactg acggggtggt |
| | | gcgtaacggc aaaagcaccg ccggacatca gcgctagcgg agtgtatact |
| | | ggcttactat gttggcactg atgagggtgt cagtgaagtg cttcatgtgg |
| | | caggagaaaa aaggctgcac cggtgcgtca gcagaatatg tgatacagga |
| | | tatattccgc ttcctcgctc actgactcgc tacgctcggt cgttcgactg |
| | | cggcgagcgg aaatggctta cgaacggggc ggagatttcc tggaagatgc |
| | | caggaagata cttaacaggg aagtgagagg gccgcggcaa agccgttttt |
| | | ccataggctc cgcccccctg acaagcatca cgaaatctga cgctcaaatc |
| | | agtggtggcg aaacccgaca ggactataaa gataccaggc gtttccccct |
| | | ggcggctccc tcgtgcgctc tcctgttcct gcctttcggt ttaccggtgt |
| | | cattccgctg ttatggccgc gtttgtctca ttccacgcct gacactcagt |
| | | tccgggtagg cagttcgctc caagctggac tgtatgcacg aaccccccgt |
| | | tcagtccgac cgctgcgcct tatccggtaa ctatcgtctt gagtccaacc |
| | | cggaaagaca tgcaaaagca ccactggcag cagccactgg taattgattt |
| | | agaggagtta gtcttgaagt catgcgccgg ttaaggctaa actgaaagga |
| | | caagttttgg tgactgcgct cctccaagcc agttacctcg gttcaaagag |
| | | ttggtagctc agagaacctt cgaaaaaccg ccctgcaagg cggttttttc |
| | | gttttcagag caagagatta cgcgcagacc aaaacgatct caagaagatc |
| | | atcttattaa tcagataaaa tatttctaga tttcagtgca atttatctct |
| | | tcaaatgtag cacctgaagt cagccccata cgatataagt tgtaattctc |
| | | atgtttgaca gcttatcatc gataagcttt aatgcggtag tttatcacag |
| | | ttaaattgct aacgcagtca ggcaccgtgt atgaaatcta acaatgcgct |
| | | catcgtcatc ctcggcaccg tcaccctgga tgctgtaggc ataggcttgg |
| | | ttatgccggt actgccgggc ctcttgcggg atatcGGTTT CTTAGACGTC |
| | | AGGTGGCACT TTtcggggaa atgtgcgcgg aacccctatt tgtttatttt |
| | | tctaaataca ttcaaatatg tatccgctca tgagacaata accctgataa |
| | | atgcttcaat aatattgaaa aaggaagagt atgagtattc aacatttccg |
| | | tgtcgccctt attccctttt ttgcggcatt ttgccttcct gtttttgctc |
| | | acccagaaac gctggtgaaa gtaaaagatg ctgaagatca gttgggtgca |
| | | cgagtgggtt acatcgaact ggatctcaac agcggtaaga tccttgagag |
| | | ttttcgcccc gaagaacgtt ttccaatgat gagcactttt aaagttctgc |
| | | tatgtggcgc ggtattatcc cgtgttgacg ccgggcaaga gcaactcggt |
| | | cgccgcatac actattctca gaatgacttg gttgagtact caccagtcac |
| | | agaaaagcat cttacggatg gcatgacagt aagagaatta tgcagtgctg |
| | | ccataaccat gagtgataac actgcggcca acttacttct gacaacgatc |
| | | ggaggaccga aggagctaac cgcttttttg cacaacatgg gggatcatgt |
| | | aactcgcctt gatcgttggg aaccggagct gaatgaagcc ataccaaacg |
| | | acgagcgtga caccacgatg cctTAGgcaa tggcaacaac gttgcgcaaa |
| | | ctattaactg gcgaactact tactctagct tcccggcaac aattaataga |
| | | ctggatggag gcggataaag ttgcaggacc acttctgcgc tcggcccttc |
| | | cggctggctg gtttattgct gataaatctg gagccggtga gcgtgggtct |
| | | cgcggtatca ttgcagcact ggggccagat ggtaagccct cccgtatcgt |
| | | agttatctac acgacgggga gtcaggcaac tatggatgaa cgaaatagac |
| | | agatcgctga gataggtgcc tcactgatta agcattggca ccaccaccac |
| | | caccactaaC CCGGGACCAA GTTTACTCAT ATATACttta gattgattta |

TABLE 3-continued

SEQUENCES

| SEQ ID: | Label | SEQUENCE |
|---|---|---|
| | | aaacttcatt tttaatttaa aaggatctag gtgaagatcc tttttgataa |
| | | tCTCATGACC AAAATCCCTT AACGgcatgc accattcctt gcggcggcgg |
| | | tgctcaacgg cctcaaccta ctactGGGCT GCTTCCTAAT GCAGGAGTCG |
| | | CATAAGGGAG AGCGTCTGGC GAAAGGGGGA TGTGCTGCAA GGCGATTAAG |
| | | TTGGGTAACG CCAGGGTTTT CCCAGTCACG ACGTTGTAAA ACGACGGCCA |
| | | GTGCCAAGCT TAAAAAaaat ccttagcttt cgctaaggat CTGCAGTTAT |
| | | AATCTCTTTC TAATTGGCTC TAAAATCTTT ATAAGTTCTT CAGCTACAGC |
| | | ATTTTTTAAA TCCATTGGAT GCAATTCCTT ATTTTTAAAT AAACTCTCTA |
| | | ACTCCTCATA GCTATTAACT GTCAAATCTC CACCAAATTT TTCTGGCCTT |
| | | TTTATGGTTA AAGGATATTC AAGGAAGTAT TTAGCTATCT CCATTATTGG |
| | | ATTTCCTTCA ACAACTCCAG CTGGGCAGTA TGCTTTCTTT ATCTTAGCCC |
| | | TAATCTCTTC TGGAGAGTCA TCAACAGCTA TAAAATTCCC TTTTGAAGAA |
| | | CTCATCTTTC CTTCTCCATC CAAACCCGTT AAGACAGGGT TGTGAATACA |
| | | AACAACCTTT TTTGGTAAAA GCTCCCTTGC TAACATGTGT ATTTTTCTCT |
| | | GCTCCATCCC TCCAACTGCA ACATCAACGC CTAAATAATG AATATCATTA |
| | | ACCTGCATTA TTGGATAGAT AACTTCAGCA ACCTTTGGAT TTTCATCCTC |
| | | TCTTGCTATA AGTTCCATAC TCCTTCTTGC TCTTTTTAAG GTAGTTTTTA |
| | | AAGCCAATCT ATAGACATTC AGTGTATAAT CCTTATCAAG CTGGAATTCa |
| | | gcgttacaag tattacacaa agttttttat gttgagaata ttttttttgat |
| | | ggggcgccac ttatttttga tcgttcgctc aaagAAGCGG CGCCAGGGNT |
| | | GTTTTTCTTT TCACCAGTNA GACGGGCAAC AGAACGCCAT Gagcggcctc |
| | | atttcttatt ctgagttaca acagtccgca ccgctgtccg gtagctcctt |
| | | ccggtgggcg cggggcatga ctatcgtcgc cgcacttatg actgtcttct |
| | | ttatcatgca actcgtagga caggtgccgg cagcgcccaa cagtcccccg |
| | | gccacggggc ctgccaccat acccacgccg aaacaagcgc cctgcaccat |
| | | tatgttccgg atctgcatcg caggatgctg ctggctaccc tgtggaacac |
| | | ctacatctgt attaacgaag cgctaaccgt ttttatcagg ctctgggagg |
| | | cagaataaat gatcatatcg tcaattatta cctccacggg gagagcctga |
| | | gcaaactggc ctcaggcatt tgagaagcac acggtcacac tgcttccggt |
| | | agtcaataaa ccggtaaacc agcaatagac ataagcggct atttaacgac |
| | | cctgccctga accgacgacc gggtcgaatt tgctttcgaa tttctgccat |
| | | tcatccgctt attatcactt attcaggcgt agcaccaggc gtttaagggc |
| | | accaataact gccttaaaaa aattacgccc cgccctgcca ctcatcgcag |
| | | tactgttgta attcattaag cattctgccg acatggaagc catcacagac |
| | | ggcatgatga acctgaatcg ccagcggcat cagcaccttg tcgccttgcg |
| | | tataatattt gcccatggtg aaaacggggg cgaagaagtt gtccatattg |
| | | gccacgttta aatcaaaact ggtgaaactc acccagggat tggctgagac |
| | | gaaaaacata ttctcaataa accctttagg gaaataggcc aggttttcac |
| | | cgtaacacgc cacatcttgc gaatatatgt gtagaaactg ccggaaatcg |
| | | tcgtggtatt cactccagag cgatgaaaac gtttcagttt gctcatggaa |
| | | aacggtgtaa caagggtgaa cactatccca tatcaccagc tcaccgtctt |
| | | tcattgccat acg |
| SEQ ID: 81 | pACKO-Bla | gaactccgga tgagcattca tcaggcgggc aagaatgtga ataaaggccg |
| | | gataaaactt gtgcttattt ttctttacgg tctttaaaaa ggccgtaata |
| | | tccagctgaa cggtctggtt ataggtacat tgagcaactg actgaaatgc |
| | | ctcaaaatgt tctttacgat gccattggga tatatcaacg gtggtatatc |
| | | cagtgatttt tttctccatt ttagcttcct tagctcctga aaatctcgat |
| | | aactcaaaaa atacgcccgg tagtgatctt atttcattat ggtgaaagtt |
| | | ggaacctctt acgtgccgat caacgtctca ttttcgccaa aagttggccc |
| | | agggcttccc ggtatcaaca gggacaccag gatttattta ttctgcgaag |
| | | tgatcttccg tcacaggtat ttattcggcg caaagtgcgt cgggtgatgc |
| | | tgccaactta ctgatttagt gtatgatggt gtttttgagg tgctccagtg |
| | | gcttctgttt ctatcagctg tccctcctgt tcagctactg acggggtggt |
| | | gcgtaacggc aaaagcaccg ccggacatca gcgctagcgg agtgtatact |
| | | ggcttactat gttggcactg atgagggtgt cagtgaagtg cttcatgtgg |
| | | caggagaaaa aaggctgcac cggtgcgtca gcagaatatg tgatacagga |
| | | tatattccgc ttcctcgctc actgactcgc tacgctcggt cgttcgactg |
| | | cggcgagcgg aaatggctta cgaacggggc ggagatttcc tggaagatgc |
| | | caggaagata cttaacaggg aagtgagagg gccgcggcaa agccgttttt |
| | | ccataggctc cgccccccctg acaagcatca cgaaatctga cgctcaaatc |
| | | agtggtggcg aaacccgaca ggactataaa gataccaggc gtttccccct |
| | | ggcggctccc tcgtgcgctc tcctgttcct gcctttcggt ttaccggtgt |
| | | cattccgctg ttatggccgc gtttgtctca ttccacgcct gacactcagt |
| | | tccgggtagg cagttcgctc caagctggac tgtatgcacg aaccccccgt |
| | | tcagtccgac cgctgcgcct tatccggtaa ctatcgtctt gagtccaacc |
| | | cggaaagaca tgcaaaagca ccactggcag cagccactgg taattgattt |
| | | agaggagtta gtcttgaagt catgcgccgg ttaaggctaa actgaaagga |
| | | caagttttgg tgactgcgct cctccaagcc agttacctcg gttcaaagag |
| | | ttggtagctc agagaacctt cgaaaaaccg ccctgcaagg cggttttttc |
| | | gttttcagag caagagatta cgcgcagacc aaaacgatct caagaagatc |
| | | atcttattaa tcagataaaa tatttctaga tttcagtgca atttatctct |
| | | tcaaatgtag cacctgaagt cagccccata cgatataagt tgtaattctc |
| | | atgtttgaca gcttatcatc gataagcttt aatgcggtag tttatcacag |
| | | ttaaattgct aacgcagtca ggcaccgtgt atgaaatcta acaatgcgct |

TABLE 3-continued

SEQUENCES

| SEQ ID: | Label | SEQUENCE |
|---|---|---|
| | | catcgtcatc ctcggcaccg tcaccctgga tgctgtaggc ataggcttgg ttatgccggt actgccgggc ctcttgcggg atatcGGTTT CTTAGACGTC AGGTGGCact tttcggggaa atgtgcgcgg aacccctatt tgtttatttt tctaaataca ttcaaatatg tatccgctca tgagacaata accctgataa atgcttcaat aatattgaaa aaggaagagt atgagtattc aacatttccg tgtcgccctt attccctttt ttgcggcatt ttgccttCCT GTTTTTGCTC ACCCAGAAAC ACTAGtgcag caatggcaac aacgttgcgc aaactattaa ctggcgaact acttactcta gcttcccggc aacaattaat agactggatg gaggcggata aagttgcagg accacttctg cgctcggccc ttccggctgg ctggtttatt gctgataaat ctggagccgg tgagcgtggg tctcgcggta tcattgcagc actggggcca gatggtaagc cctcccgtat cgtagttatc tacacgacgg ggagtcaggc aactatggat gaacgaaata gacagatcgc tgagataggt gcctCACTGA TTAAGCATTG GTAACCCGGG ACCAAGTTTA CTCATATATA Ctttagattg atttaaaact tcatttttaa tttaaaagga tctaggtgaa gatccttttt gataatCTCA TGACCAAAAT CCCTTAACGg catgcaccat tccttgcggc ggcggtgctc aacggcctca acctactact GGGCTGCTTC CTAATGCAGG AGTCGCATAA GGGAGAGCGT CTGGCGAAAG GGGGATGTGC TGCAAGGCGA TTAAGTTGGG TAACGCCAGG GTTTTCCCAG TCACGACGTT GTAAAACGAC GGCCAGTGCC AAGCTTAAAA Aaaatcctta gctttcgcta aggatCTGCA GTTATAATCT CTTTCTAATT GGCTCTAAAA TCTTTATAAG TTCTTCAGCT ACAGCATTTT TTAAATCCAT TGGATGCAAT TCCTTATTTT TAAATAAACT CTCTAACTCC TCATAGCTAT TAACTGTCAA ATCTCCACCA AATTTTTCTG GCCTTTTTAT GGTTAAAGGA TATTCAAGGA AGTATTTAGC TATCTCCATT ATTGGATTTC CTTCAACAAC TCCAGCTGGG CAGTATGCTT TCTTTATCTT AGCCCTAATC TCTTCTGGAG AGTCATCAAC AGCTATAAAA TTCCCTTTTG AAGAACTCAT CTTTCCTTCT CCATCCAAAC CCGTTAAGAC AGGGTTGTGA ATACAAACAA CCTTTTTTGG TAAAAGCTCC CTTGCTAACA TGTGTATTTT TCTCTGCTCC ATCCCTCCAA CTGCAACATC AACGCCTAAA TAATGAATAT CATTAACCTG CATTATTGGA TAGATAACTT CAGCAACCTT TGGATTTTCA TCCTCTCTTG CTATAAGTTC CATACTCCTT CTTGCTCTTT TTAAGGTAGT TTTTAAAGCC AATCTATAGA CATTCAGTGT ATAATCCTTA TCAAGCTGGA ATTCagcgtt acaagtatta cacaaagttt tttatgttga gaatattttt ttgatggggc gccacttatt tttgatcgtt cgctcaaagA AGCGGCGCCA GGGNTGTTTT TCTTTTCACC AGTNAGACGG GCAACAGAAC GCCATGAgcg gcctcatttc ttattctgag ttacaacagt ccgcaccgct gtccggtagc tccttccggt gggcgcgggg catgactatc gtcgccgcac ttatgactgt cttctttatc atgcaactcg taggacaggt gccggcagcg cccaacagtc cccggccac ggggcctgcc accataccca cgccgaaaca agcgccctgc accattatgt tccggatctg catcgcagga tgctgctggc taccctgtgg aacacctaca tctgtattaa cgaagcgcta accgttttta tcaggctctg ggaggcagaa taaatgatca tatcgtcaat tattacctcc acggggagag cctgagcaaa ctggcctcag gcatttgaga agcacacggt cacactgctt ccggtagtca ataaaccggt aaaccagcaa tagacataag cggctattta acgaccctgc cctgaaccga cgaccgggtc gaatttgctt tcgaatttct gccattcatc cgcttattat cacttattca ggcgtagcac caggcgttta agggcaccaa taactgcctt aaaaaaatta cgccccgccc tgccactcat cgcagtactg ttgtaattca ttaagcattc tgccgacatg gaagccatca cagacggcat gatgaacctg aatcgccagc ggcatcagca ccttgtcgcc ttgcgtataa tatttgccca tggtgaaaac gggggcgaag aagttgtcca tattggccac gtttaaatca aaactggtga aactcaccca gggattggct gagacgaaaa acatattctc aataaaccct ttagggaaat aggccaggtt ttcaccgtaa cacgccacat cttgcgaata tatgtgtaga aactgccgga aatcgtcgtg gtattcactc cagagcgatg aaaacgtttc agtttgctca tggaaaacgg tgtaacaagg gtgaacacta tcccatatca ccagctcacc gtctttcatt gccatacg |
| SEQ ID: 82 | pKQ | ATGGATCCGA GCTCGAGATC TGCAGCTGGT ACCATATGGG AATTCGAAGC TTGGGCCCGA ACAAAAACTC ATCTCAGAAG AGGATCTGAA TAGCGCCGTC GACCATCATC ATCATCATCA TTGAGTTTAA ACGGTCTCCA GCTTGGCTGT TTTGGCGGAT GAGACAAGAT TTTCAGCCTG ATACAGATTA AATCAGAACG CAGAAGCGGT CTGATAAAAc AGAATTTGCC TGGCGGCAGT AGCGCGGTGG TCCCACCTGA CCCCATGCCG AACTCAGAAG TGAAACGCCG TAGCGCCGAT GGTAGTGTGG GGTCTCCCCA TGCGAGAGTA GGGAACTGCC AGGCATCAAA TAAAACGAAA GGCTCAGTCG AAAGACTGGG CCTTTCGTTT TATCTGTTGT TTGTCGGTGA ACGATATCTG CTTTTCTTCG CGAATtaatt ccgcttcgca ACATGTgagc aaaaggccag caaaaggcca ggaaccgtaa aaaggccgcg ttgctggcgt ttttccatag gctccgcccc cctgacgagc atcacaaaaa tcgacgctca agtcagaggt ggcgaaaccc gacaggacta taaagatacc aggcgtttcc ccctggaagc tccctcgtgc gctctcctgt tccgaccctg ccgcttaccg gatacctgtc cgcctttctc ccttcgggaa gcgtggcgct ttctcatagc tcacgctgta ggtatctcag ttcggtgtag gtcgttcgct ccaagctggg ctgtgtgcac gaaccccccg ttcagcccga ccgctgcgcc ttatccggta actatcgtct tgagtccaac ccggtaagac acgacttatc gccactggca gcagccactg gtaacaggat tagcagagcg aggtatgtag gcggtgctac agagttcttg aagtggtggc ctaactacgg ctacactaga |

TABLE 3-continued

| SEQ ID: | Label | SEQUENCE |
|---|---|---|
| | | aggacagtat ttggtatctg cgctctgctg aagccagtta ccttcggaaa aagagttggt agctcttgat ccggcaaaca aaccaccgct ggtagcggtg gtttttttgt ttgcaagcag cagattacgc gcagaaaaaa aggatctcaa gaagatcctt tgatcttttc tacggggtct gacgctcagt ggaacgaaaa ctcacgttaa gggattttgg TCATGAgttg tgtctcaaaa tctctgatgt tacattgcac aagataaaaa tatatcatca tgaacaataa aactgtctgc ttacataaac agtaatacaa ggggtgttat gagccatatt caacgggaaa cgtcttgctc gaggccgcga ttaaattcca acatggatgc tgatttatat gggtataaat gggctcgcga taatgtcggg caatcaggtg cgacaatcta tcgattgtat gggaagcccg atgcgccaga gttgtttctg aaacatggca aaggtagcgt tgccaatgat gttacagatg agatggtcag actaaactgg ctgacggaat ttatgcctct tccgaccatc aagcatttta tccgtactcc tgatgatgca tggttactca ccactgcgat ccccgggaaa acagcattcc aggtattaga agaatatcct gattcaggtg aaaatattgt tgatgcgctg gcagtgttcc tgcgccggtt gcattcgatt cctgtttgta attgtccttt taacagcgat cgcgtatttc gtctcgctca ggcgcaatca cgaatgaata acggtttggt tgatgcgagt gattttgatg acgagcgtaa tggctggcct gttgaacaag tctggaaaga aatgcataag cttttgccat tctcaccgga ttcagtcgtc actcatggtg atttctcact tgataacctt atttttgacg aggggaaatt aataggttgt attgatgttg gacgagtcgg aatcgcagac cgataccagg atcttgccat cctatggaac tgcctcggtg agttttctcc ttcattacag aaacggcttt ttcaaaaata tggtattgat aatcctgata tgaataaatt gcagtttcat ttgatgctcg atgagttttt ctaatcagaa ttggttaatt ggttgtaaca ctggcagagc attacgctga cttgacggga cggcggcttt gttgaataaa tcgaactttt gctgagttga aggatcCTCG GGagttgtca gcctgtcccg cttataagat catacgccgt tataCGTTGT TTACGCTTTG AGGAATTAAC C |

What is claimed is:

1. A composition comprising an orthogonal glutamyl-tRNA (glutamyl O-tRNA), wherein the glutamyl O-tRNA comprises the polynucleotide sequence of SEQ ID NO.: 67 or is transcribed from a complementary polynucleotide sequence thereof;

and wherein the glutamyl O-tRNA suppresses in the presence of tRNA synthetase (RS) selected from the group consisting of: an *Archaeoglobus fulgidus* synthetase, a *Methanosarcina mazei* synthetase, a *Methanobacterium thermoautotrophicum* synthetase, and a *Pyrococcus horikoshii* synthetase.

2. The composition of claim 1, further comprising a polynucleotide comprising a selector codon that is an amber codon.

3. The composition of claim 1, wherein the -tRNA synthetase preferentially aminoacylates the glutamyl O-tRNA with a selected amino acid.

4. The composition of claim 3, wherein a suppression efficiency of the tRNA synthetase and the glutamyl O-tRNA together is 4 to 5-fold greater than a suppression efficiency of the glutamyl O-tRNA in the absence of the glutamyl-tRNA synthetase.

5. The composition of claim 3, wherein the tRNA synthetase comprises an amino acid sequence comprising any one of SEQ ID NO.: 69 (AfRS), SEQ ID NO.: 73 (MmRS), SEQ ID NO.: 75 (MtRS), or SEQ ID NO.: 77 (PhRS).

6. The composition of claim 1, comprising a cell.

7. The composition of claim 6, wherein the cell is an *E. coli* cell.

8. The composition of claim 1, comprising a translation system.

9. A cell comprising a translation system, wherein the translation system comprises:

an orthogonal glutamyl-tRNA (glutamyl O-tRNA) comprising the polynucleotide sequence of SEQ ID NO.: 67 or is transcribed from a complementary polynucleotide sequence thereof;

a glutamyl-tRNA synthetase derived from a tRNA synthetase (RS) selected from the group consisting of: SEQ ID NO.: 69 (AfRS), SEQ ID NO.: 73 (MmRS), SEQ ID NO.: 75 (MtRS) and SEQ ID NO.: 77 (PhRS); and, a first selected amino acid;

wherein the glutamyl O-tRNA recognizes a first selector codon, and the tRNA synthetase preferentially aminoacylates the glutamyl O-tRNA with the first selected amino acid.

10. The cell of claim 9, wherein the cell further comprises an additional different O-tRNA/tRNA synthetase pair and a second selected amino acid, wherein the additional O-tRNA recognizes a second selector codon and the additional tRNA synthetase preferentially aminoacylates the additional O-tRNA with the second selected amino acid.

11. The cell of claim 9, wherein the cell is a non-eukaryotic cell.

12. The cell of claim 11, wherein the non-eukaryotic cell is an *E. coli* cell.

13. The cell of claim 9, further comprising a nucleic acid that comprises a polynucleotide that translates into a polypeptide of interest, wherein the polynucleotide comprises a selector codon that is recognized by the glutamyl O-tRNA.

14. An *E. coli* cell, comprising:

an orthogonal glutamyl tRNA (glutamyl O-tRNA), wherein the glutamyl O-tRNA comprises the polynucleotide sequence of SEQ ID NO.: 67 or is transcribed from a complementary polynucleotide sequence thereof;

a glutamyl-tRNA synthetase, wherein the glutamyl-tRNA synthetase preferentially aminoacylates the glutamyl O-tRNA with a selected amino acid;

the selected amino acid; and, a nucleic acid that comprises a polynucleotide that encodes a polypeptide of interest, wherein the polynucleotide comprises the selector codon that is recognized by the glutamyl O-tRNA, and wherein the glutamyl-tRNA synthetase comprises a glutamyl-RS selected from the group consisting of: an *Archaeoglobus fulgidus* (Af) synthetase, a *Methanosarcina mazei* (Mm) synthetase, a *Methanobacterium thermoautotrophicum* (Mt) synthetase, and a *Pyrococcus horikoshii* (Ph) synthetase.

* * * * *